US005939306A

United States Patent [19]
Alex et al.

[11] Patent Number: 5,939,306
[45] Date of Patent: Aug. 17, 1999

[54] OSMOSENSING HISTIDINE KINASES

[75] Inventors: Lisa A. Alex, Pasadena; Melvin I. Simon, San Marino, both of Calif.; Claude Selitrennikoff, Evergreen; Jacqueline Agnan, Aurora, both of Colo.

[73] Assignees: University Technology Corporation, Colo.; California Institute of Technology, Calif.

[21] Appl. No.: 08/843,530

[22] Filed: Apr. 16, 1997

[51] Int. Cl.$^6$ ........................................................ C12N 1/21
[52] U.S. Cl. ........................ 435/252.3; 435/6; 435/69.1; 435/194; 435/254.1; 435/254.11; 435/254.21; 435/254.22; 435/254.3; 435/254.4; 435/320.1; 536/23.1; 536/23.2; 536/23.7; 536/23.74
[58] Field of Search ................................... 536/23.1, 23.2, 536/23.7, 23.74; 435/6, 69.1, 194, 252.3, 254.1, 254.11, 254.21, 254.22, 254.3, 254.2, 320.1

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |

OTHER PUBLICATIONS

Anaissie, "Opportunistic Mycoses in the Immunocompromised Host: Experience at a Cancer Center and Review," *Clin. Infect. Dis.* 14[Suppl. 1]:S43–S53 [1992].

Zinsser 'Microbiology, Chapter 87, "Opportunistic Mycoses," W.K. Joklik, et al., [eds.], Appleton, Century–Crofts, Norwalk, CT, pp. 1183–1190 [1984].

Walsh and Dixon, "Spectrum of Mycoses," in *Medical Microbiology*, 4th ed, Baron (ed.) University of Texas Medical Branch, Galveston, TX, pp. 919–925 [1996].

Chandler, Mycotic Diseases, 8 Candidiasis, *Color Atlas and Text of Histopathology of Mycotic Diseases*, pp. 42–46 [1980].

Meunier et al., "Fungal Infections in Immunocompromised Hosts: Candidemia in Immunocompromised Patients," *Clin. Infect. Dis.* 14[Suppl. 1]:S120–S125 [1992].

Loose et al., "Distribution of a Corticosteroid–binding Protein in *Candida* and Other Fungal Genera," *J. Gen. Microbiol.* 129:2379–2385 [1983].

Loose and Feldman, "Characterization of a Unique Corticosterone–binding Protein in *Candida albicans*," *J. Biol. Chem.* 257:4925–4930 [1982].

Cole, "Basic Biology of Fungi," in *Medical Microbiology*, 4th ed., Baron (ed.), University of Texas Medical Branch, Galveston, TX, pp. 903–911 [1996].

McGinnis and Tyring, "Introduction to Mycology," in *Medical Microbiology*, 4th ed., Baron (ed.), University to Texas Medical Branch, Galveston, TX, pp. 893–902 [1996].

Dixon and Walsh, "Antifungal Agents," in *Medical Microbiology*, 4th ed., Baron (ed.), University of Texas Medical Branch, Galveston, TX, pp. 926–932 [1996].

Gooday, "Chitin metabolism: A target for antifungal and antiparasitic drugs," *Molecular Aspects of Chemotherapy*, E. Borowski (ed.), Pergamon Press, pp. 175–185 [1990].

Georgopapadakou and Tkacz, "The fungal cell wall as a drug target," *Trends Microbiol.* 3:98–104 [1995].

Schmatz et al., "Treatment of *Pneumocystis carinii* pneumonia with 1,3–β–glucan synthesis inhibitors," *Proc. Natl. Acad. Sci.* 87:5950–5954 [1990].

Alex and Simon, "Protein histidine kinases and signal transduction in prokaryotes and eukaryotes," *Trends Genet.* 10:133–138 [1994].

Swanson et al., "Histidine and aspartate phosphorylation: two–component systems and the limits of homology," *Trends Biochem. Sci.* 19: 485–490 [1994].

Parkinson et al., "Communication Modules in Bacterial Singaling Proteins," *Ann. Rev. Genet.* 26:71–112 [1992].

Chang et al., "*Arabidopsis* Ethylene–Response Gene ETR1: Similarity of Product to Two–Component Regulators," *Science* 262:539–544 [1993].

Ota and Varshavsky, "A Yeast Protein Similar to Bacterial Two–Component Regulators," *Science* 262:566–569 [1993].

Maeda et al., "A two–component system that regulates an osmosensing MAP kinase cascade in yeast," *Nature* 369:242–245 [1994].

Schuster et al., "The hybrid histidine kinase DokA is part of the osmotic response system of *Dictyostelium*," *EMBO J.* 15:3880–3889 [1996].

Wang et al., "A two–component histidine kinase gene that functions in *Dictyostelium* development," *EMBO J.* 15:3890–3898 [1996].

Kakimoto, "CK11, a Histidine Kinase Homolog Implicated in Cytokinin Signal Transduction," *Science* 274:982–985 [1996].

Alex et al., "Hyphal development in *Neurospora crassa*: Involvement of a two–component histidine kinase," *Proc. Natl. Acad. Sci.* 93:3416–3421 [1996].

(List continued on next page.)

*Primary Examiner*—Robert A. Wax
*Assistant Examiner*—Enrique D. Longton
*Attorney, Agent, or Firm*—Medlen & Carroll, LLP

[57] ABSTRACT

The present invention relates to histidine kinases, including osmosensing fungal histidine kinases. In particular, the present invention provides amino acid and nucleic acid sequences of fungal histidine kinases from organisms such as Candida (e.g., *C. albicans*) and Neurospora (e.g., *N. crassa*). The present invention further provides compositions and methods for the development of antifungal compounds.

15 Claims, 9 Drawing Sheets

OTHER PUBLICATIONS

Morgan et al., "Two–component signal–transduction systems in budding yeast MAP a different pathway?,"*Trends Cell Biol.* 5:453–457 [1995].

Posas et al., "Yeast HOG1 MAP Kinase Cascade Is Regulated by a Multistep Phosphorelay Mechanism in the SLN1–YPD1–SSK1 'Two–Component' Osmosensor," *Cell* 86:865–875 [1996].

Appleby et al., "Signal Transduction via the Multi–Step Phosphorelay: Not Necessarily a Road Less Traveled," *Cell* 86:845–848 [1996].

Burbulys et al., "Initiation of Sporulation in B. subtilis is Controlled by a Multicomponent Phosphorelay," *Cell* 64:545–552 [1991].

Uhl and Miller, "Integration of multiple domains in a two–component sensor protein: the *Bordetella pertussis* BvgAS phosphorelay," *EMBO J.* 15:1028–1036 [1996].

Brown et al., "Yeast Skn7p functions in a eukaryotic two–component regulatory pathway," *EMBO J.* 13:5186–5194 [1994].

Brown et al., "SKN7, a Yeast Multicopy Suppressor of a Mutation Affecting Cell Wall β–Glucan Assembly, Encodes a Product with Domains Homologous to Prokaryotic Two–Component Regulators and to Heat Shock Transcription Factors," *J. Bacteriol.* 175:6908–6915 [1993].

Krems et al., "The response regulator–like protein Pos9/Skn7 of *Saccharomyces cerevisiae* is involved in oxidative stress resistance," *Curr. Genet.* 29:327–334 [1996].

Page et al., "Identification of ASK10 as a Multicopy Activator of Skn7p–dependent Transcription of a HIS3 Reporter Gene," *Yeast* 12:267–272 [1996].

Springer, "Genetic Control of Fungal Differentiation: The Three Sporulation Pathways of *Neurospora crassa*," *BioEssays* 15:365–374 [1993].

Vollmer and Yanofsky, "Efficient cloning of genes of *Neurospora crassa*," *Proc. Natl. Acad. Sci.* 83:4869–4873 [1986].

Dieffenbach and Dveksler, *PCR Primer, a Laboratory Manual*, Cold Spring Harbor Press, Plainview NY [1995].

Mullis et al., "Specific Enzymatic Amplification of DNA In Vitro: The Polymerase Chain Reaction," *Cold Spring Harbor Symposia*, vol. LI, pp. 263–273 [1986].

Selitrennikoff et al., "Formation and Regeneration of Protoplasts Derived from a Temperature–Sensitive *Osmotic Strain of Neurospora crassa*," *Exp. Mycol.* 5:155–161 [1981].

Davis and deSerres, "Genetic and Microbiological Research Techniques for *Neurospora crassa*," *Meth. Enzymol.* 27A:79–143 [1970].

Grindle and Dolderson, "Notes and Brief Articles: Effects of a Modifier Gene on the Phenotype of a Dicarboximide–Resistant Mutant of *Neurospora Crassa*," *Trans. Brit. Mycol. Soc.* 87:457–487 [1986].

Sambrook et al. (eds.), *Molecular Cloning: A Laboratory Manual*, Cold Spring Harbor Laboratory Press, Cold Spring Harbor, NY, [1989].

Vollmer and Yanofsky, *Proc. Natl. Acad. Sci.* 83:4869–4873 [1986].

Orbach et al., "Cloning and Characterization of the Gene for β–Tubulin from a Benomyl–Resistant Mutant of *Neurospora crassa* and Its Use as a Dominant Selectable Marker," *Mol. Cell. Biol.* 6:2452–2461 [1986].

Selitrennikoff and Sachs, "Lipofectin increases the efficiency of DNA–mediated transformation of *Neurospora crassa*," *Fungal Genet. Newsl.* 38:90–91 [1991].

White and Woodward, "A simple method for making disposable race tubes," *Fungal Genet. Newsl.* 42:79 [1995].

Altschul et al., "Basic Locl Alignment Search Tool," *J. Mol. Biol.* 215:403–410 [1990].

Bairoch, "Teh PROSITE dictionary of sites and patterns in proteins, its current status," *Nucl. Acids Res.* 21:3097–3103 [1993].

Bruchez et al., "Regulatory sequences in the transcription of *Neurospora crassa* genes: CAAT box, TATA box, Introns, Poly(A) tail formation sequences," *Fungal Genet. Newsl.* 40:89–96 [1993].

Nagasawa et al., "A novel sensor–regulator protein that belongs to the homologous family of signal–transduction proteins involved in adaptive responses in *Escherichia coli*," *Mol. Microbiol.* 6:799–807 [1992].

Liao et al., "Molecular Characterization of Two Gene Loci Required for Production of the Key Pathogenicity Factor Pectate Lyase in *Pseudomonas viridiflava*," *Mol. Plant–Microbe Interact.* 7:391–400 [1994].

Corbell and Loper, "A Global Regulator of Secondary Metabolite Production in *Pseudomonas fluorescens* Pf–5," *J. Bacteriol.* 177:6230–6236 [1995].

Perego and Hoch, "Protein aspartate phosphatases control the output of two–component signal transduction systems," *Trends Genet.*12:97–101 [1996].

Stock et al., "Signal transduction in bacteria," *Nature* 344:395–400 [1990].

Perkins et al., "Chromosomal Loci of *Neurospora crassa* ," *Microbiol. Rev.* 46:426–570 [1982].

Gierasch, "Signal Sequences," *Biochem.* 28:923–930 [1989].

von Heijne, "A new method for predicting signal sequence cleavage sites," *Nucleic Acids Res.* 14: 4683–4690 [1986].

Larsson et al.,"A gene encoding sn–glycerol 3–phosphate dehydrogenase (NAD+) complements an osmosensitive mutant of *Saccharomyces cerevisiae*," *Mol. Microbiol.* 10:1101–1111 [1993].

Aatsinki et al., "A Coupled One–Step Reverse Transcription PCR Procedure for Generation of Full–Length Open Reading Frames," *BioTechn.* 16:282–288 [1994].

Dale et al., "A Rapid Single–Stranded Cloning Strategy for Producing a Sequential Series of Overlapping Clones for Use in DNA Sequencing: Application to Sequencing the Corn Mitochondrial 18 S rDNA," *Plasmid* 13:31–40 [1985].

Orbach et al., "The *Neurospora crassa arg–2* Locus," *J. Biol. Chem.* 265:10981–10987 [1990].

Okamoto et al., "Nit–3, the structural gene of nitrate reductase in *Neurospora crassa*: nucleotide sequence and regulation of mRNA synthesis and turnover," *Mol. Gen. Genet.* 227:213–223 [1991].

Bruchez et al., "Regulatory sequences involved in the translation of *Neurospora crassa* mRNA: Kozak sequences and stop codons," *Fungal Genet. Newsl.* 40:85–88 [1993].

Lupas et al., "Predicting Colied Coils from Protein Sequences," *Science* 252:1162–1164 [1992].

Yao and Spudich, "Primary structure of an archaebacterial transducer, a methyl–accepting protein associated with sensory rhodopsin I," *Proc. Natl. Acad. Sci.* 89:11915–11919 [1992].

Reinert et al., "Genetic Regulation of the qa Gene Cluster of *Neurospora crassa*: Induction of qa Messenger Ribonucleic Acid and Dependency on qa–1 Function," *Mol. Cell. Biol.* 1:829–835 [1981].

Case et al., "Efficient transformation of *Neurospora crassa* by utlizing hybrid plasmid DNA," *Proc. Natl. Acad. Sci.* 76:5259–5263 [1979].

Metzenberg, "An alternate way of collecting, storing and dissecting *Neurospora*," *Fungal Genet. Newsl.* 35:28 [1988].

Selker, "Premeiotic Instability of Repeated Sequences in *Neurospora Crassa*," *Ann. Rev. Genet.* 24:579–613 [1990].

Manning and Mitchell, "Strain Variation and Morphogenesis of Yeast–and Mycelial–Phase *Candida Albicans* in Low–Sulfate, Synthetic Medium," *J. Bacteriol.* 142:714–719 [1980].

Scherer and Stevens, "A *Candida albicans* dispersed, repeated gene family and its epidemiologic applications," *Proc. Natl. Acad. Sci.* 85:1452–1456 [1988].

Moreno et al., "Molecular Genetic Analysis of Fission Yeast *Schizosaccharomyces pombe*," *Meth. Enzymol.* 194:795–823 [1991].

Vieira and Messing, "New pUC–derived cloning vectors with different selectable markers and DNA replication origins," *Gene* 100:189–194 [1991].

Hughes, "Histidine kinases hog the limelight," *Nature* 369:187–188 (1994), reports on the conclusions drawn from the analysis of Maeda et al. Maeda et al., *Nature* 369:242–245 [1994].

Wingrove and Gober, "Identification of an Asymmetrically Localized Sensor Histidine Kinase Responsible for Temporally and Spatially Regulated Transcription," *Science* 274:597–601 (1996).

Huang et al., "Purification of a Protein Histidine Kinase from the Yeast *Saccharomyces cerevisiae*," *The American Society for Biochemistry and Molecular Biology* 266(14):9023–9031 (1991).

Orth et al., "A Serine (Threonine) Protein Kinase Confers Fungicide Resistance in the Phytopathogenic Fungus *Ustilago maydis*," *Appl.Environ. Microbiol.* 61(6):2341–2345 (1995).

Livingston, "Locus–specific Changes in Cell Wall Composition Characteristic of Osmotic Mutants of *Neurospora crassa*," *J. Bacteriol.* 99(1):85–90 (1969).

Brewster et al., "An Osmosensing Signal Transduction Pathway in Yeast," *Science* 259:1760–1763 (1993).

Koshland, "The Two–Component Pathway Comes to Eukaryotes," *Science* 262:532 (1993).

Tentler et al., "Inhibition of *Neurospora crassa* Growth by a Glucan Synthase–1 Antisense Construct," *Curr. Microbiol.* 34:1–6 (1997).

Simons et al., "Cell wall 1,6–β–glucan synthesis in *Saccharomyces cerevisiae* depends on ER glucosidases I and II, and the molecular chaperone BiP/Kar2p," *EMBO J.* 17:396–405 (1988).

Linden et al., "Blue Light Regulation in *Neurospora crassa*," *Fungal Gen. Biol.* 22:141–150 (1997).

Scott, "Biochemical Genetics of Morphogenesis in *Neurospora*," *Ann. Rev. Microbiol.* 30:85–104 (1976).

Reynaga–Peña and Bartnicki–Garcia, "Apical Branching in a Temperature Sensitive Mutant of *Aspergillus niger*," *Fungal Gen. Biol.* 22:153–167 (1997).

Kobayashi, "Fungi," *Microbiology*, Fourth Edition, J.B. Lippincott Company, Philadelphia, pp. 737–765 (1990).

Berry, "Candidiasis," *Diagnostic Atlas of the Major Systemic Fungal Infections*, Pfizer Inc., pp. 41–46 (1994).

Bennett, "Antimicrobial Agents (Continued): Antifungal Agents," *Goodman & Gilman's The Pharmacological Basis of Therapeutics*, Ninth Edition, (eds. Hardman et al.); McGraw–Hill, New York, pp. 1175–1190 (1996).

Nagahashi et al., "Isolation of CaSLN1 and CaNIK1, the genes for osmosensing histidine kinase homologues, from the pathogenic fungus *Candida albican*," *Microbiology* 144:425–432 (1998).

Schumacher et al., "The Osmotic–1 Locus of *Neurospora crassa* Encodes a Putative Histidine Kinase Similar to Osmosensors of Bacteria and Yeast," *Current Microbiology* 34:340–347 (1997).

Schumacher et al. (Jun. 5, 1996) GenBank Database, Accession No. U53189.

Alex et al. (Apr. 12, 1996) GenBank Database, Accession No. U50263.

Alex et al. (Apr. 12, 1996) GenBank Database, Accession No. U50264.

Ball et al. (Aug. 20, 1995) EMBL Database, Accession No. X88804.

```
              •••••••••∇∇∇∇∇
Oslp    MTDGPTLAAIAALVKSLAVDPATTQTSGLRPSTHVRLPGPYTREKGD
BarA    MTNYSLRAR----------------MMILILAPTVLIGLLLSIFFV
RepA    NRRTDTGCWRKSV----LNKLGIKGRVLLLTILPASLMAAVLGGYF-
ApdA    M---------------LKKLGIKGRVLLLTLLPTSLMALVLGGYF-
Slnlp   MRFGLPSKLELTPPFRIGIRTQLTALVSIVALGSLIILAVTTGVYFT Oslp    VVRIEQLETAAIAASPPAMPDTPNAPTDALFSNGTLSPSSETPDARY
BarA    ----------------------------------------------
RepA    ----------------------------------------------
ApdA    ----------------------------------------------
Slnlp   DRLYIAAQLKSSQIDQTLNYLYYQAYYLASRDALQSSLTSYVAGNKS Oslp    FIDEALEGLREHVDDQSKLLDSQRQELAGVNAQLIEQKQLQEKALAI
BarA    ----------------------------------------------
RepA    ----------------------------------------------
ApdA    ----------------------------------------------
Slnlp   SVIQKFLSSSNLFYVAKVYDSSFNAVLNATNNGTGDLIPEDVLDSLF Oslp    LERELWKHQKANEAFQKALREIGEIVTAVARGDLSKKVRMNSVEMDP
BarA    ----------------------------------------------
RepA    ----------------------------------------------
ApdA    ----------------------------------------------
Slnlp   PSSLETIGILTDPVLNSTDYLMSMSLPIFANPSIILTDSRVYGYITI Oslp    INTMMDQLQVFSSEVSRVAREVGTEGILGGQAQIEGVDGTWKELTDN
BarA    ----------------------------------------------
RepA    ----------------------------------------------
ApdA    ----------------------------------------------
Slnlp   SVFNDTTALEHSTIAIISAVYNSQGKASGYHFVFPPYGSRSDLPQKV Oslp    TDQVREIASVTTAVAHGDLTKKIERPAKGEILQLQQTINTMVDQLRT
BarA    ----------------------------------------------
RepA    ----------------------------------------------
ApdA    ----------------------------------------------
Slnlp   ISSAFRNGKGGSLKQTNILSTRNTALGYSPCSFNLVNWVAIVSQPES Oslp    ARDVGTEGILGGQADVEGVQGMWNELTVNVNAMANNLTTQVRDIIKV
BarA    ----------------------------------------------
RepA    ----------------------------------------------
ApdA    ----------------------------------------------
Slnlp   LAKIITGTVIAIGVFVILLTLPLAHWAVQPIVRLQKATELITEGRGL
```

FIG. 3

```
Oslp   LTQKVQAECRGEIFELKKTINSMVDQLQQFAREVTKIAREVGTEGRL
BarA   -----------------------------------------------
RepA   -----------------------------------------------
ApdA   -----------------------------------------------
Slnlp  SRASSFKRGFSSGFAVPSSLLQFNTAEAGSTTSVSGHGGSGHGSGAA Oslp   VQGTWRDLTENVNGMAMNLTTQVREIAKVTTAVAKGDLTKKIGVEVQ
BarA   YNDLQRQLEDAGASIIEPLAVSTEYGMSLQNRESIGQLI-SVLHRRH Oslp   IEARRMVIEEIPYTLRGTVFNALKTLAVKANEKFLDL-TYRVDHSV-
BarA   LEAGKLILESIPFPLRSTLDEVVTLLAHSSHDKGLEL-TLNIKSDV-
RepA   IEAGKLVLDNIPFNLRDLLQDTLTILAPAAHAKQLEL-VSLVYRDT-
ApdA   IEAGKLVLDSIPFNLRDLLQDTLTILAPAAHAKQLEL-VSLVYRDT-
Slnlp  NVLQRTKLEKRDFCITDVALQIKSIFGKVAKDQRVRLSISLFPNLIR Oslp   FRLRQIILNLVGNAIKFTEHGEVSLTIQKASSVQCSTEEY-------
BarA   LRLQQIITNLVGNAIKFTENGNIDILVEKRALSNTKV----------
RepA   LRLRQILTNLVSNAIKFTRQGTIVARAMLEDETEEHA----------
ApdA   LRLKQILTNLVSNAIKFTREGTIVARAMLEEEHEDSV----------
Slnlp  NRIIQIVMNLVSNALKFTPVDGTVDVRMKLLGEYDKELSEKKQYKEV Oslp   -----------------------------------------------
BarA   -----------------------------------------------
RepA   -----------------------------------------------
ApdA   -----------------------------------------------
Slnlp  TENLETTDKYDLPTLSNHRKSVDLESSATSLGSNRDTSTIQEEITKR Oslp   -----------------------------------------------
BarA   -----------------------------------------------
RepA   -----------------------------------------------
APDA   -----------------------------------------------
Slnlp  YKKVNDREKASNDDVSSIVSTTTSSYDNAIFNSQFNKAPGSDDEEGG

*****                         ***
Oslp   ----AIEFVVSDTGIGIPADKLDLIFDTFQQADGSMTRKFGGTGLGL
BarA   ----QIEVQIRDTGIGIPERDQSRLFQAFRQADASISRRHGGTGLGL
RepA   ----QLRISVQDTGIGLSSQDVRALFQAFSQADNSISRQPGGTGLGL
ApdA   ----QLRISIQDTGIGLSNQDVRALFQAFSQADNSLSRQPGGTGLGL
Slnlp  PKTWVISIEVEDTGPGIDPSLQESVFHPFVQGDQTLSRQYGGTGLGL
```

FIG. 3 (cont.)

```
Os1p   LMGGDVWVKSEYGKGSKFFFTCVVRLANDDISLIAKQLNPYKSHQVL
BarA   EMGGDISFHSQPNRGSTFWFHINLDL-NPNIIIEGPSTQCLAGKRLA
RepA   QMGGEIGVDSTPGEGSEFWISLNLPKAREDREETANQALEGLRAAVL
ApdA   QMGGEIGVDSTPGEGSEFWISLNLPKTRDDAEDLPGPPLLGRRVAVL
Slnlp  MMHGTMKLESKVGVGSKFTFTLPLNQTKEISFADMEFPFEDEFNPES Os1p   HGPEIAKMLHGLGLVPIVVDSERNPALEKARAAGQAPYD-VIIVDSI
BarA   AQCTL-DILSETPL--EVVYSPTFSALPPAHYDMMLLGIAVTFREPL
RepA   ALEHQLEDCGLQTVVFTNLENLLNGVTAAHETPQAIDLVVLGVTALE
ApdA   ALQHQLEDCGLEVTPFNTLEALTNGITGVHQSEQAIDLAVLGITTND
Slnlp  SVAKSIKSRQSTSSVATPATNRSSLTNDVLPEVRSKGKHETKDVGNP Os1p   S-VDDFKYLPIVLLAPVVHVSLKSCLDLGITSYMTTPCQLIDLGNGM
BarA   KAVSMTDFLMLALPCHAQVNAEKLKQDGIGACLLKPLTPTRLLPALT
RepA   HIWDLENLNCKVMVLCPTTEHALFQMSVHDVYTQLQAKPACNRKLQK
ApdA   HIWDLEHLGCKVLVLCPTTEQTLFHLSVPNPHSQLQAKPACTRKLRR
Slnlp  DNGGLEQLQEKNIKPSICLTGAEVNEQNSLSSKHRSRHEGLGSVNLD Os1p   TPSLA-DNTKSFEILLAE----DNTVNQRLAVKILEKYHHVVTVVGN
BarA   TLLPVTDESKLAMTVMAV---DDNPANLKLIGALLEDMVQHVELCDS
RepA   RAVRTDVALPLSSRAPRVLCVDDNPANLLLVQTLLEDMGAEVVAVDG
ApdA   RRARSEPEETLSSRAPRVLCVDDNPANLLLIQTLLEDMGAKVLAVDN
```

FIG. 3 (cont.)

```
Cos1    1   ------------------------------------------------------------DLL
OS-1    1   MTDGPTLAAIAALVKSLAVDPATTQTSGLRPSTHVRLPGPYTREKGDLERELSALVVRIE
BAR-A   1   ------------------------------------------------------------
SLN1    1   -------------------------------------MRFGLPSKLELTPPFRIG

Cos1    4   CWSCVVAIYKAPPYINKKFFLSVVYLEFLPLSPMNPTKKPRLSPMQPSVFEILNDP--EL
OS-1    61  QLETAAIAASPPAMPDTPNAPTDALFSNGTLSPSSETPDARYPAPLPRNGFIDEAL--EG
BAR-A   1   ------------------------------------------------------------
SLN1    19  IRTQLTALVSIVALGSLIILAVTTGVYFTSNYKNLRS-DRLYIAAQLKSSQIDQTLNYLY

Cos1    62  YSQHCHSLRETLLDHFN--------------------HQATLIDTYEHELEKSKNANK
OS-1    119 LREHVDDQSKLLDSQRQELAGVNAQLIEQKQLQEKALAIIEQERVATLERELWKHQKANE
BAR-A   1   ------------------------------------------------------------
SLN1    78  YQAYYLASRDALQSSLTSYVAGN----K-----------SADNWVDSLSVIQKFLSSSNL

Cos1    100 AFQQALS--EIGTVVISVAM--GDLSKKVEIHTVE---NDPEILKVKITINTMMDQLQTF
OS-1    179 AFQKALR--EIGEIVTAVAR--GDLSKKVRMNSVE---MDPEITTFKRTINTMMDQLQVF
BAR-A   1   -------------MTNYSLR--ARMMILILAPTVL---IG-LLLSIFFVVHRYNDLQRQL
SLN1    123 FYVAKVYDSSFNAVLNATNNGTGDLIPEDVLDSLFPLSTDTPLPSSLETIGILTDPVLNS
                         .          .         . .        .         .       *

Cos1    153 ANEVTKVATEVANG--ELGGQAKNDGSVGIWRSLTDNVNIMALNLTNQVREIADVTRAV-
OS-1    232 SSEVSRVAREVGTEG-ILGGQAQIEGVDGTWKELTDNVNVMAQNLTDQVREIASVTTAV-
BAR-A   42  EDAGASIIEPLAVST-EYGMSLQN------RESIGQLISVLHRRHSDIVRAISVYD----
SLN1    183 TDYLMSMSLPIFANPSIILTDSRVYGYITIIMSAEGLKSVFNDTTALEHSTIAIISAVYN
                                                                       *.

Cos1    210 -AKGDLSRKINVHAQGEILQLQRTINTMVDQLRTFAFEVSKVARDVGVLGILGGQALIEN
OS-1    290 -AHGDLTKKIERPAKGEILQLQQTINTMVDQLRTFASEVTRVARDVGTEGILGGQADVEG
BAR-A   91  -ENNRLFVTSNFHLDPSSMQLGSNV--------PFPRQLT-VTRD--------GDIMILR
SLN1    243 SQGKASGYHFVFPPYGSRSDLPQKVFSIKN--DTFISSAFRNGKG-GS----LKQTNILS
                       *           *                 .

Cos1    269 VEGIWEELTDNVNAMALNLTTQVRNI-ANVTTAVAKGDLSKKVTADCKGEILDLKLTINQ
OS-1    349 VQGMWNELTVNVNAMANNLTTQVRDI-IKVTTAVAKGDLTQKVQAECRGEIFELKKTINS
BAR-A   133 TPIISESYSP-----DESPSSDAKNS-QNMLGYIALELDLKSVRLQQYKEIF--------
SLN1    296 TRNTALGYSP----CSFNLVNWVAIVSQPESVFLSPATKLAKIITGTVIAIGVFVILLTL
                              . .                                 *
```

FIG. 6

```
Cos1  328  MVDRLQNFALAVTTLSREVGTLGILGGQAN---VQDVEGAWKQVTENVNLMATNLTNQVR
OS-1  408  MVDQLQQFAREVTKIAREVGTEGRLGGQAT---VHDVQGTWRDLTENVNGMAMNLTTQVR
BAR-A 179  -IS---------SVMMLFCIGIALIFG--------------WR---LMR-----DVTGPIR
SLN1  352  PLAHWAVQPIVRLQKATELITEGRGLRPSTPRTISRASSFKRGFSSGFAVPSSLLQFNTA
                .                .                    .         .

Cos1  385  SIATVTTAVAHGDLSQKIDVHAQGEILQLKNTINKMVDSLQLFASEVSKVAQDVGINGKL
OS-1  465  EIAKVTTAVAKGDLTKKIGVEVQGEILDLKNTINTMVDRLGTFAFEVSKVAREVGTDGTL
BAR-A 208  NMVNTVDRIRRGQLDSRVEGFMLGELDMLKNGINSMAMSLAAYH---------------
SLN1  412  EAGSTTSVSGHG-GSGHGSGAAFSANSSMKSAINLGNEKMSPPEEE-NKIPNN-HTDAKI
                .*       .                .*   **      .

Cos1  445  GIQAQVSDVDGLWKEITSNVNTMASNLTSQVR----------------
OS-1  525  GGQAQVDNVEGKWKDLTENVNTMASNLTSQVRGISTVTQAIANGDMSRKIEVEAKGEILI
BAR-A 252  -------------EEMQHNIDQATSDLRETLE----------------------------
SLN1  469  SMDGSLNHDLLGPHSLRHNDTDRSSNRSHILT-----------------------------
                .  *   .*       .

Cos1  477  ------------------------------------------------------------
OS-1  585  LKETINMMVDRLSIFCNEVQRVAKDVGVDGIMGGQADVAGLKGRWKEITTDVNTMANNLT
BAR-A 271  ------------------------------------------------------------
SLN1  501  ------------------------------------------------------------

Cos1  477  ----AFAQITAAATDGDFTRFITVEALGEMDALKTK---INQMVFNLRESLQRNT----A
OS-1  645  AQVRAFGDITNAATDGDFTKLVEVEASGEMDELKKK---INQMVYNLRDSIQRNT----Q
BAR-A 271  ----Q-MEIQNVELD---------------------------------------------L
SLN1  501  ----TSANLTEARLP-DYRRLFSDELSDLTETFNTMTDALDQHYALLEERVRARTKQLEA
                .

Cos1  526  AREAAELANSAKSEFLANMSHEIRTPLNGIIGMTQLSLDTELTQYQREMLSIVHNLANSL
OS-1  698  AREAAELANKTKSEFLANMSHEIRTPMNGIIGMTQLTLDTDLTQYQREMLNIVNSLANSL
BAR-A 282  AKKRAQEAARIKSEFLANMSHELRTPLNGVIGFTRLTLKTELTPTQRDHLNTIERSANNL
SLN1  556  AKIEAEAANEAKTVFIANISHELRTPLNGILGMTAISMEETDVNKIRNSLKLIFRSGELL
           *.   *. *         *. *.**.***.***.**..* *  ...      *  *  .  *

Cos1  586  LTIIDDILDISKIEANRMTVEQIDFSLRGTVFGALKTLAVKAIEKNLDLTYQCDSSFPDN
OS-1  758  LTIIDDILDLSKIEARRMVIEEIPYTLRGTVFNALKTLAVKANEKFLDLTYRVDHSVPDH
BAR-A 342  LAIINDVLDFSKLEAGKLILESIPFPLRSTLDEVVTLLAHSSHDKGLELTLNIKSDVPDN
SLN1  616  LHILTELLTFSKNVLQRTKLEKRDPCITDVALQIKSIFGKVAKDQRVRLSISLFPNLIRT
           * *.  ..* **    .  *      . *     ..        .... *.
```

FIG. 6 (cont.)

```
Cos1   646   LI--GDSFRLRQVILNLAGNAIKFTK-EGKVSVSVKKSD-K-MVLDSKLLLEVCVSDTGI
OS-1   818   VV--GDSFRLRQIILNLVGNAIKFTE-HGEVSLTIQKASSV-QCSTEEYAIEFVVSDTGI
BAR-A  402   VI--GDPLRLQQIITNLVGNAIKFTE-NGNIDILVEKRA----LSNTKVQIEVQIRDTGI
SLN1   676   MVLWGDSNRIIQIVMNLVSNALKFTPVDGTVDVRMKLLGEYDKELSEKKQYKEVYIKKGT
                ..  **  *.  *..  **  **.***    *....                    *

Cos1   701   GIEK-----DKLGL--IFDTFCQADGSTTRKFGGTGLGLSISKQLIHLMGGEIWVTSEYG
OS-1   874   GIPA-----DKLDL--IFDTFQQADGSMTRKFGGTGLGLSISKRLVNLMGGDVWVKSEYG
BAR-A  455   GIPE-----RDQSR--LFQAFRQADASISRRHGGTGLGLVITQKLVNEMGGDISPHSQPN
SLN1   736   EVTENLETTDKYDLPTLSNHRKSVDLESSATSLGSNRDTSTIQEEITKRN-TVANESIYK
                .         .        *   .   *..    .         .        *

Cos1   754   SGSNFYFTVCVSPS-NIRYTRQTEQLLPFSSHYVLFVSTEHTQEELDVLRDGIIELGLIP
OS-1   927   KGSKFFFTCVVRLA-NDDISLIAKQLNPYKSHQVLFIDKGRTGHGPEIAK-MLHGLGLVP
BAR-A  508   RGSTFWFHINLDLNPNIIIEGPSTQCLAGKRLAYVEPNSAAAQCTLDILSETPLEVVYSP
SLN1   795   KVNDREKASNDDVS-SIVSTTTSSYDNAIFNSQFNKAPGSDDEEGGNLGRPIENPKTWVI
                                                                       .

Cos1   813   IIVRN------IEDATLTEPVKYDIIMID-SIEIAKKLRLLSEVKYIPLVLVHHSIPQLNM
OS-1   985   IVVDSERNPALEKARAAGQAPYDVIIVD-SIEDARRLRSVDDFKYLPIVLLAP-VVHVSL
BAR-A  568   TFSALPP---AHYDMMLLGIAVTFREPL-TMQHERLAKAVSMTDFLMLALPCH--AQVNA
SLN1   854   SIEVEDTGP-GIDPSLQESVFHPFVQGDQTLSRQYGGTGLGLSICRQLANMMH--GIMKL
                        ..      .      .                        .

Cos1   867   RVCIDLGISSYANTPCSIT---DLASAIIPAL-----ESRSISQN---SDES-VRYKILL
OS-1   1043  KSCLDLGITSYMTTPCQLI---DLGNGMVPAL-----ENRATPSL---ADVT-KSFEILL
BAR-A  622   EKLKQDGIGACLLKPLTPT---RLLPALTEFC-----HHKQNTLLPV-TDESKLAMTVMA
SLN1   911   ESKVGVGSKFTFTLPLNQTKEISFADMEFPFEDEFNPESRKNRRVKFSVAKSIKSRQSTS
                *       *                                         .

Cos1   915   AEDNLVNQR--LAVAILEKQG----HLVEVVEN---G-LE-----AYEAIKRNKYDVVLM
OS-1   1091  AEDNTVNQR--LAVKILEKYH----HVVTVVGN---G-EE-----AVEAVKRKKFDVILM
BAR-A  673   VDDNPANLK--LIGALLEDMV----QHVELCDS---G-HQ-----AVERAKQMPFDLILM
SLN1   971   SVATPATNRSSLTNDVLPEVRSKGKHETKDVGNPNMGREEKNDNGGLEQLQEKNIKPSIC
                ...  *  .*      .           *  .     *  .

Cos1   960   DVQMPVMGGFEATEKIRQWEKKSNPIDSLTFRTPIIALTAHAMLGDREKSLAKGMDDYVS
OS-1   1136  DVQMPIMGGFEATAKIREYERSLG----SQ--RTPIIALTAHAMMGDREKCIQAQMDEYLS
BAR-A  718   DIQMPDMDGIRLACELIHQLPHQO-------QTPVIAVTAHAMAGQKEKLLGAGMSDYLA
SLN1   1031  LTGAEVNEQNSLSSKHRSRHEGLG---SVNLDRPFLQSTGTATSSRNIPTVKDDDKNETS
                                                  *. **    .
```

FIG. 6 (cont.)

```
Cos1   1020   KPLKP----KLLMQT-------------------INKCIHNINQLKELSRN---SRGSDF
OS-1   1191   KPLQQ----NHLIQT-------------------ILKCATLGGQLLEKNRERELTRAADA
BAR-A   770   KPIEEERLHNLLLRYKPGSGISSRVVTPEVNEIVVNPNATLDWQLALRQAAGKTDLARDM
SLN1   1088   VKILVVED-NHVNQEVIKRMLN--------LEGIENIELACDGQEAFDKVKELTSKGENY
                   .       . .                                  *

Cos1   1054   AKKMTRN-TPGSTTRQGSDEGS---------VEDMIGDTPRQGS---VEGGGTSSRPVQR
OS-1   1228   VTGGRRD-NGMYSASQAAQHAA---------LRPPLATRGLTAA---DSLVSGLESPSIV
BAR-A   830   LQMLLDF-LPEVRNKVEEQLVGENPEGLVDLIHKLHGSCGYSGVPRMKNLCQLIEQQLRS
SLN1   1139   NMIFMDVQMPKVDGLLSTKMIRRDLG----YTSPIVALTAFADD---SNIKECLESGMNG

Cos1   1101   RSATEGSITTISEQIDR-------------
OS-1   1275   TADKEDPLSRARASLSEPN--IHKAS----
BAR-A   889   GTKEEDLEPELLELLDEMDNVAREASKILG
SLN1   1192   FLSKPIKRPKLKTILTEFCAAYQGKKNNK-
```

FIG. 6 (cont.)

OSMOSENSING HISTIDINE KINASES

FIELD OF THE INVENTION

The present invention relates to fungal osmosensing histidine kinases. In particular, the present invention is directed to histidine kinases from Candida (e.g, *C. albicans*) and Neurospora (e.g, *N. crassa*).

BACKGROUND

Fungal organisms have become increasingly significant pathogens in immunocompromised patients, especially those who because of cancer, organ transplantation, chemotherapy, pregnancy, age, diabetes, complications following extensive surgery, and various immune system dysfunctions, are at risk of experiencing life-threatening diseases caused by organisms which do not ordinarily pose a threat to normal, immunocompetent people. For example, fungal infections have become one of the leading factors contributing to morbidity and mortality in cancer patients, and fungi account for 4–12% of nosocomial (hospital-acquired) pathogens in leukemia patients (E. Anaissie, Clin. Infect. Dis., 14[Suppl.1]:S43 [1992]). The incidence of nosocomial bloodstream infections with fungi such as Candida ("candidemia") has increased in recent years and now accounts for 5.6% of all primary bloodstream infections (Id.). Yeast infections may also be life-threatening in other settings, such as in the case of intravenous drug abusers who use non-sterile substances (lemon juice is commonly used) to dilute drugs prior to injection.

Of the over 100 Candida species, approximately seven are isolated with great frequency from human specimens (T. Mitchell, in *Zinsser Microbiology*, W. K. Joklik, et al., [eds], Appleton, Century-Crofts, Norwalk, Conn., pp. 1183–1190 [1984]). A brief taxonomic chart of Candida is shown in Table 1. Some Candida species are related to organisms, such as Saccharomyces in the subclass Hemiascomycetidae, class Ascomycetes, subdivision Ascomycotina, division Ascomycota. Also, some mycologists consider *C. stellatoidea* to be a variant of *C. albicans*.

TABLE 1

TAXONOMY OF THE GENUS CANDIDA

| | |
|---|---|
| Kingdom: | Mycetae (Fungi) |
| Division: | Deuteromycota |
| Subdivision: | Deuteromycotina |
| Form Class: | Deuteromyces |
| Form Subclass: | Blastomycetidae |
| Genus: | Candida |
| Species: | *albicans* |
| | *glabrata* |
| | *guilliermondi* |
| | *krusei* |
| | *lipolytica* |
| | *lusitaniae* |
| | *parapsilosis* |
| | *pseudotropicalis* |
| | *rugosa* |
| | *stellatoidea* |
| | *tropicalis* |

The first exposure to fungi experienced by many humans occurs during the birth process, when *C. albicans* present in the mother's vaginal canal colonizes the buccal cavity, and portions of the upper and lower gastrointestinal tract of the newborn. This colonization usually results in the establishment of *C. albicans* as a commensal organism in these areas, for the life of the individual. However, *C. albicans* is also the most common fungal pathogen of humans, worldwide, with other Candida species becoming increasingly important in fungal disease in humans and other animals.

As a commensal, *C. albicans* exists as a unicellular yeast; during invasive disease, the organism has a filamentous morphology. When *C. albicans* is implicated in disease, it may indicate that the patient has a co-existing immune, endocrine or other debilitating disorder that must also be addressed in order to effectively manage the fungal disease. The principal risk factors that predispose individuals to deeply invasive candidiasis include protracted course of broad spectrum antimicrobials, cytotoxic chemotherapy, corticosteroids, and vascular catheters.

Candida Infection and Diagnosis

Because clinical Candida infections and disease may be acute or chronic, superficial or disseminated, the disease syndromes are many and varied. While *C. albicans* is most commonly implicated, various other Candida species can and do invade most organ systems of the body. For example, *C. tropicalis, C. parapsilosis, C. guilliermondi, C. krusei*, and *C. lusitaniae* have emerged as important pathogens in cancer patients (E. Anaissie, supra). Candidiasis due to *C. albicans*, as well as other Candida species, is the most common opportunistic fungal infection observed (See, Walsh and Dixon, "Spectrum of Mycoses," in Baron (ed.), *Medical Microbiology*, 4th ed, University of Texas Medical Branch, Galveston, Tex. [1996], pp. 919–925). Superficial candidiasis may involve the epidermal and mucosal surfaces (e.g., the oral cavity, pharynx, esophagus, intestines, urinary bladder, and vagina). In deep candidiasis, the gastrointestinal tract and intravascular catheters are the two major portals of entry, with the kidneys, liver, spleen, brain, eyes, heart, and other tissues being the major sites involved.

The major difficulties in diagnosis of Candida infections are encountered in cases of systemic disease. Chronic mucocutaneous, pulmonary candidiasis, endocarditis, and fungemia must be diagnosed early and treated promptly with an appropriate antifungal regimen, in order to avoid fatality (W. Chandler, *Color Atlas and Text of Histopathology of Mycotic Diseases*, p. 44 [1980]). The incidence of candidiasis in certain patient populations is striking. Up to 30% of leukemia patients acquire systemic candidiasis. (E. Anaissie, supra.) This is of great significance, as some reports indicate that the fatality rate for disseminated candidiasis in cancer patients is *80%* (F. Meunier, et al., Clin. Infect. Dis., 14[Suppl. 1]:S120 [1992]). Also, fatalities in most organ transplant patients who succumb to infection are most often due to opportunistic organisms, of which Candida is the leading mycotic agent (T. Mitchell, supra).

The probability of postoperative systemic candidiasis is related to the length of operation and may involve contamination with organisms during the surgery or contamination through such diverse postoperative procedures as indwelling catheters or the use of prophylactic antibacterial compounds (Id.). Prosthetic devices, including artificial heart valves or intravenous lines can be colonized and introduce Candida into the patient's bloodstream (Id.).

Significantly, many patients who develop systemic candidiasis were given corticosteroids prior to development of their Candida infection. Corticosteroids are known to depress the immune system and are often used to prevent transplant rejection. Corticosteroids and antibacterials predispose to candidiasis by depressing phagocytic activity and cell-mediated immunity, reducing the bacterial flora and indirectly increasing the Candida population (Id.). Perhaps also importantly, corticosteroids have been hypothesized to directly act on fungi and may contribute to disease progression in patients with systemic candidiasis (See e.g. D. S. Loose et al., J. Gen. Microbiol., 129:2379 [1983]; D. S. Loose and D. Feldman, J. Biol. Chem., 257:4925 [1982]).

Because of the delays necessary in making a definitive diagnosis, physicians usually treat patients empirically. For superficial infections, topical antifungals are often used; the prognosis for most types of these infections is usually quite good. For systemic disease, highly toxic antifungals must often be used. Administration of these compounds requires careful patient monitoring (patients are usually admitted) because of their serious side effects (e.g., the nephrotoxicity, hypokalemia, anemia, fever and other toxic effects associated with the use of amphotericin B).

Fungal Physiology and Treatment of Candida Disease

The development of effective antifungal agents has lagged behind that of antibacterial agents. As bacteria are prokaryotic and offer numerous structural and metabolic targets that differ from humans, we have been more successful in identifying and developing antibacterial agents. In contrast, like humans, fungi are eukaryotic. Thus, most agents toxic to fungi are also toxic to humans. In addition, because fungi generally grow more slowly and in multi-cellular forms in vitro, they are more difficult to quantify than bacteria, complicating experiments designed to evaluate the in vitro and/or in vivo properties of potential antifungals.

Four general groups of antifungals have been developed, including the polyenes (e.g., amphotericin, nystatin, and pimaricin), azoles (e.g., fluconazole, itraconazole, and ketoconazole), allylamines and morpholines (e.g., naftifine and terbinafine), and antimetabolites (e.g., 5-flurocytosine). The site of action for most antifungals is the ergosterol present in the fungal cell membrane, or its biosynthetic pathway. However, other antifungals act at other sites, such as the fungal cell wall.

Fungal Cell Wall

The fungal cell wall is a rigid, stratified structure that consists of chitinous microfibrils encased in a matrix of small polysaccharides, proteins, lipids, inorganic salts, and pigments, that provides support and shape to the cell. The chitin within fungal cell walls is a ($\beta$1–4)-linked polymer of N-acetyl glucosamine, produced in the cytosol by chitin synthetase.

The major polysaccharides of the cell wall matrix consist of non-cellulosic glucans, including glycogen-like compounds, mannans (mannose polymers), chitosan (glucosamine polymers), and galactans (galactose polymers). Fucose, rhamnose, xylose, and uronic acids may also be present in small amounts. The term "glucan" is used in reference to a large group of D-glucose polymers with glycosidic bonds. Of these, the most common glucans present in the fungal cell wall are in the $\beta$-configuration. Polymers with ($\beta$1-3)- and ($\beta$1-6)-linked glucosyl units with various proportions of 1-3 and 1-6 linkages being common. Many fungi, and yeasts in particular, have soluble peptidomannans within a matrix of $\alpha$- and $\beta$-glucans, as part of the outer portion of their cell wall. The fungal cell wall is essential for the viability of the organism, as it prevents osmotic lysis of the cell. Even a small lesion within the cell wall can lead to the extrusion of cytoplasm due to the internal pressure within the cell (See, Cole, "Basic Biology of Fungi, in Baron (ed.), *Medical Microbiology*, 4th ed., University of Texas Medical Branch, Galveston, Tex. [1996], pp. 903–911). Indeed, creation of such lesions is the mechanism of action of many antifungals, including amphotericin B.

As *C. albicans* may be in the form of budding yeast cells, pseudohyphae, germ tubes, true hyphae, and chlamydospores, differences between these forms are of interest in the development of antifungals. In the yeast form, the *C. albicans* cell wall contains approximately 30–60% glucan, 25–50% mannan (mannoprotein), 1–2% chitin, 2–14% lipid, and 5–15% protein (McGinnis and Tyring, "Introduction to Mycology," in Baron (ed.), *Medical Microbiology*, 4th ed., University of Texas Medical Branch, Galveston, Tex. [1996], pp. 893–902). Glucans with ($\beta$1-3) and ($\beta$1-6)-linked groups comprise approximately a high percentage of the yeast cell wall. These glucans may impede the access of amphotericin B to the plasma membrane (See, McGinnis and Tyring, supra, at p. 896).

Fungal Cell Membrane

The fungal plasma (i.e., cell) membrane is similar to mammalian plasma membranes, with the exception being that fungal plasma membranes contain ergosterol, rather than cholesterol as the principal sterol. The plasma membrane is selectively permeable, and apparently regulates the passage of materials into and out of the cell. Sterols present in the membrane provide structure, modulate membrane fluidity, and may control other physiologic events.

Polyene antifungals (e.g., amphotericin B, nystatin, and pimaricin) bind ergosterol, to form complexes that allow the rapid leakage of cellular potassium, other ions, and small molecules out of affected fungal cells. This results in the inhibition of fungal glycolysis and respiration. Other antifungals such as the azoles (e.g., fluconazole, imidazole, ketoconazole, and itraconazole), and allylamines and morpholines interfere with the ergosterol biosynthesis. Inhibition of ergosterol formation may result in permeability changes in the plasma membrane, inhibits growth, and may lead to excessive chitin production and abnormal fungal growth.

Fungal Microtubules

Fungi also possess microtubules composed of tubulin. These structures are involved in the movement of organelles, chromosomes, nuclei, and Golgi vesicles. Microtubules are the principal components of the spindle fibers that aid movement of the chromosomes during mitosis and meiosis. Exposure to some antifungal agents disrupts the movement of the nuclei, mitochondria, vacuoles, and apical vesicles. In addition, destruction of cytoplasmic microtubules interferes with transport of secretory materials, and may inhibit cell wall synthesis. Griseofulvin, a compound commonly used to treat dermatophytic infections binds with microtubule-associated proteins involved in tubulin assembly, and acts by stopping mitosis at metaphase.

Antifungal Compounds

Despite the identification of cell membrane, cell wall, and microtubule targets for antifungal action, antifungal development has been slow. Amphotericin B remains the treatment mainstay for life-threatening and other mycoses. Discovered in 1956, amphotericin B remains the drug of choice for candidiasis, cryptococcosis, aspergillosis, zygomycosis, coccidioidomycosis, histoplasmosis, blastomycosis, and paracoccidioidomycosis. Amphotericin B must be administered intravenously and is associated with numerous, often serious side effects, including phlebitis at the infusion site, fever, chills, hypokalemia, anemia, and nephrotoxicity). Importantly, fungal resistance to amphotericin B has been reported for various opportunistic fungi, including *Pseudallescheria boydii*, Fusarium, Trichosporon, and some *C. lusitaniae* and *C. guilliermondii* isolates (See, Dixon and Walsh, "Antifungal Agents," in Baron (ed.), *Medical Microbiology*, 4th ed., University of Texas Medical Branch, Galveston, Tex. [1996], pp. 926–932).

Nystatin is another broad-spectrum polyene antifungal. However, its toxicity to humans prevents its widespread use. Currently, it is limited to topical applications, where it is effective against yeasts, including *C. albicans*. Pimaricin (natamycin) is a topical polyene active against yeasts and molds; this compound is used to treat superficial mycotic eye infections.

Ketoconazole was the first antifungal developed that was suitable for oral administration, although it may also be used topically. In non-immunocompromised patients, it may be used to treat histoplasmosis and blastomycosis. It is also used against mucosal candidiasis and various cutaneous mycoses (e.g., dermatophyte infections, pityriasis versicolor, and cutaneous candidiasis). However, it is not useful for treatment of aspergillosis or systemic yeast infections. The triazoles (e.g., fluconazole and itraconazole) have found use in systemic mycoses. Fluconazole is now often used to treat candidemia in non-neutropenic patients, and may be used in cryptococcosis and some cases of coccidioidomycosis. Itraconazole is often effective against histoplasmosis, blastomycosis, sporotrichosis, coccidioidomycosis, and some cases of cryptococcosis and aspergillosis.

Side effects are not as common with the azoles as with amphotericin B, although life-threatening hepatic toxicity may result from long-term use. Other side effects include nausea, vomiting, and drug interactions with such compounds as cyclosporin, antihistamines, anticoagulants, antiseizure and oral hypoglycemic medications, as well as other compounds, are of potential concern.

Unlike antibacterials, few antimetabolite compounds are useful as antifungals. The most commonly used antifungal is 5-fluorocytosine, a fluorinated analog of cytosine. However, like other antimetabolites, the emergence of drug resistance has become a problem. Thus, it is seldom used alone. Nonetheless, in combination with amphotericin B, it remains the treatment of choice for cryptococcal meningitis, and is effective against some diseases caused by dematiaceous fungi.

Other antifungals include griseofulvin, an antimicrobial produced by *Penicillium griseofulvin*, that is active against most dermatophytes. Potassium iodide is another compound that is used as an antifungal to enhance transepidermal elimination of fungal organisms in cases of cutaneous and lymphocutaneous sporotrichosis, although it is not effective against *Sporothrix schenckii* in vitro.

Anti-fungal susceptibility testing is generally not standardized, and the results of in vitro tests do not always correspond to the in vivo results. Thus, preliminary antifungal selection is often made on the basis of the specific organism identified as being involved in the patient's disease. While this approach may be useful in avoiding selection of an antifungal to treat fungi known to exhibit primary resistance to an agent, it is less useful in the selection of antifungals to treat fungi known to develop secondary (i.e., drug-induced) resistance.

Primary, as well as secondary, antifungal resistance has become an increasing problem. For example, with most polyenes, the resistance is almost always primary (i.e., the susceptibility profiles for the species are characteristic, inherent, and rarely change in response to drug exposure). Primary and secondary resistance to azoles has been reported for most medically important yeasts. In view of the development of resistance, as well as the relative lack of variety available in the selection of antifungals, there remains a need for the development of compounds useful for treatment of fungal diseases.

SUMMARY OF THE INVENTION

The present invention relates to osmosensing histidine kinases and methods for their use in screening antifungal compounds for their activity against fungal organisms, as well as for the development of antifungal compounds.

In one embodiment, the present invention provides a purified and isolated nucleic acid sequence encoding at least a portion of an osmosensing histidine kinase, wherein the sequence is selected from the group consisting of SEQ ID NO:1, 3, 5, and 17, and their complementary sequences. In one preferred embodiment, the nucleic acid sequence is from Neurospora. In alternative embodiments, the present invention provides compositions comprising the nucleic acid sequences selected from the group consisting of SEQ ID NO:1, 3, 5, and 17, and their complementary sequences.

The present invention also provides polynucleotide sequences that hybridize under stringent conditions to the nucleic acid sequence selected from the group consisting of SEQ ID NOS:3, and 17.

The present invention further provides substantially purified proteins comprising the amino acid sequences selected from the group consisting of SEQ ID NOS:2, 4, 6, 11, 12, and 18.

The present invention also provides expression vectors that contain nucleic acid sequences selected from the group consisting of SEQ ID NO:1, 3, 5, and 17, and their complementary sequences. It is contemplated that these sequences may be encoded by one or more expression vectors. It is also contemplated that the expression vectors of the present invention be present within host cells. In one embodiment, the host cell is prokaryotic, while in preferred embodiments, the host cell is eukaryotic. In particularly preferred embodiments, the host cell is a fungal cell. In alternate preferred embodiments the host cell is selected from the group consisting of Neurospora, Candida, Aspergillus, and Saccharomyces. In yet another particularly preferred embodiment, the host cell comprises *Candida albicans*.

The present invention also provides host cells comprising at least one DNA sequence selected from the group consisting of SEQ ID NOS:1, 3, 5, and 17, or a portion thereof, such that the host cell expresses a fungal histidine kinase or a portion therefore. In one preferred embodiment, the fungal histidine kinase is a *Neurospora crassa* histidine kinase. In another preferred embodiment, the host cell expresses *Candida albicans* histidine kinase. In an alternative preferred embodiment, the host cell expresses Saccharomyces histidine kinase.

The present invention provides compositions and methods related to osmosensing fungal histidine kinases. In particular, the present invention provides amino acid and nucleic acid sequences of fungal histidine kinases from organisms such as Candida (e.g., *C. albicans*) and Neurospora (e.g., *N. crassa*). The present invention further provides compositions and methods for the development of antifungal compounds.

DESCRIPTION OF THE DRAWINGS

FIG. 3 is a sequence alignment of OS1p (SEQ ID NO:28), BarA (SEQ ID NO:29), RepA (SEQ ID NO:30), ApdA (SEQ ID NO:31), and Sln1p (SEQ ID NO:32).

FIG. 6 is a sequence alignment of Cos1p (SEQ ID NO:33), Os1p (SEQ ID NO:34), BarA (SEQ ID NO:35), and Sln1 (SEQ ID NO:36).

DESCRIPTION OF THE INVENTION

Figure 1:
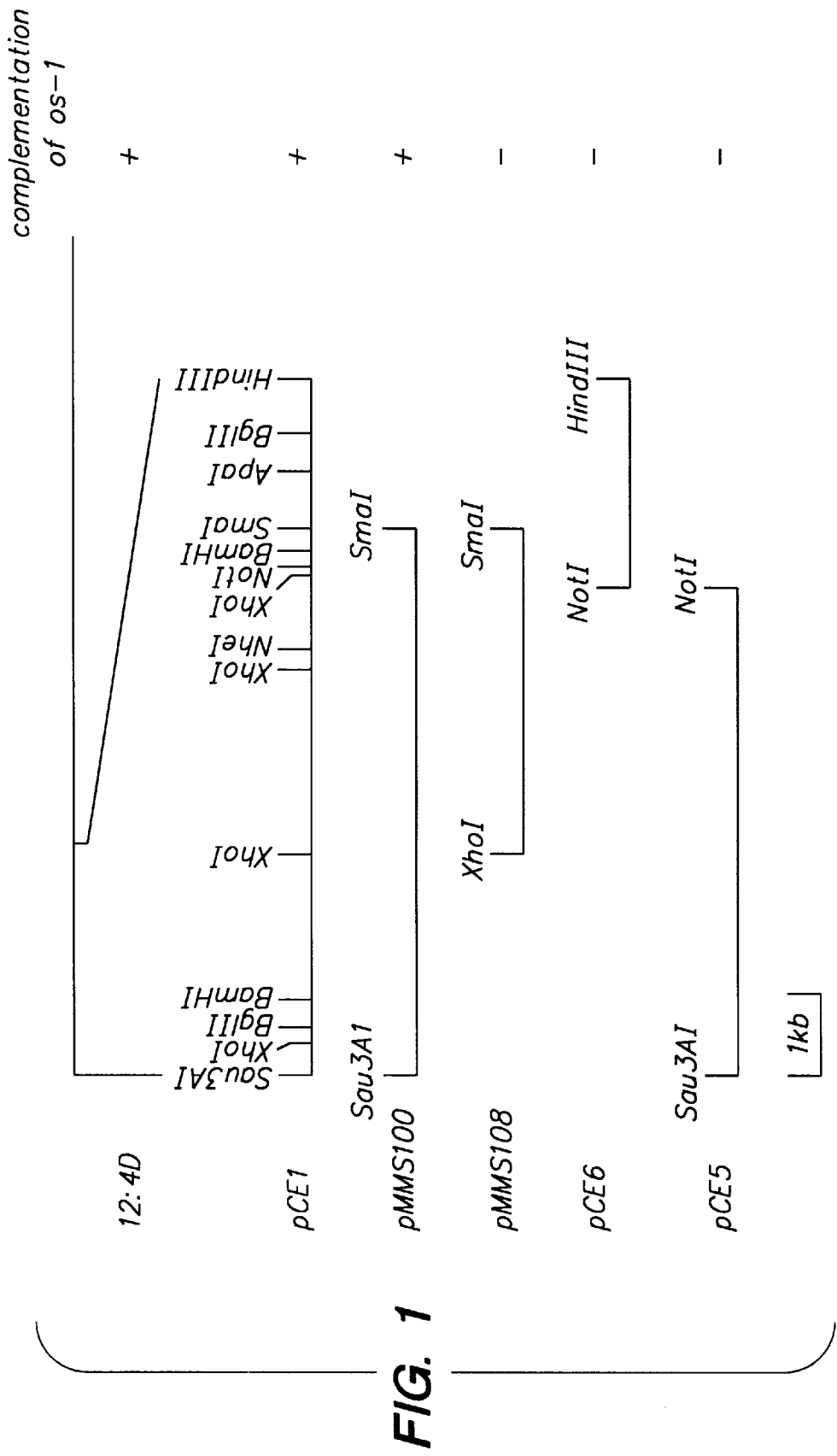
FIG. 1 shows a map of the 12:4D cosmid and its restriction sites, in comparison with pCE1, pMMS100, pMMS108, pCE6, and pCE5.

The present invention relates to osmosensing histidine kinases and methods for their use in screening antifungal compounds for their activity against fungal organisms, as well as for the development of antifungal compounds. In particular, the present invention provides a new target for antifungals, namely novel histidine kinases involved in cell wall assembly. Importantly for development of antifungals with minimal toxicity, the present invention provides a target that is widespread among diverse fungal species, but is absent from humans and other mammals. The lack of chitin, (1-6) β-glucan and (1-3) β-glucan in mammalian cells makes the pathways for their synthesis attractive targets for antifungal compounds. For example, chitin synthase and (1-3) β-glucan synthase have been considered as targets for antifungal development (See e.g., G. W. Gooday, "Chitin metabolism: A target for antifungal and antiparasitic drugs," in E. Borowski (ed.), *Molecular Aspects of Chemotherapy*, Perganon Press [1993] pp. 175–185; N. Georgopapadalou and J. Tkacz, "The fungal cell wall as a drug target," Trends Microbiol., 3:98–104 [1995]). Indeed, *Pneumocystis carinii* pneumonia has been successfully treated with (1-3) β-glucan synthase inhibitors (D. Schmatz et al., Proc. Natl. Acad. Sci., 87:5950–5954 [1982]). However, the present invention provides additional advantages over compounds that target chitin biosynthesis itself, as the critical steps of functional cell wall assembly are targetted by the present invention.

Histidine Kinase Function and Activity

The histidine kinase system is a two-component signal transduction system. These two-component signalling pathways convey a signal generated by an environmental stimulus into the interior of the cell through a series of reversible protein phosphorylation reactions (See e.g., L. A. Alex and M. I. Simon, Trends Genet., 10:133–138 [1994]). Both prokaryotes and eukaryotes have been found to have these two-component systems (See e.g., L. A. Alex and M. I. Simon, supra; R. V. Swanson et al., Trends Biochem. Sci., 19:485–490 [1994]; J. S. Parkinson et al., Ann. Rev. Genet., 26:71–112 [1992]); C. Chang et al., Science 262:539–544 [1993]; J. Hua et al., Science 262:539–544 [1995]; I. M. Ota and A. Varshavsky, Science 262:566–569 [1993]; T. Maeda et al., Nature 369:242–245 [1994]; Schuster et al., EMBO J., 5:3880–3889 [1996]; Wang et al., EMBO J., 5:3890–3898 [1996]; Kakimoto, Science 274:982–985 [1996]; and L. A. Alex et al., Proc. Natl. Acad. Sci., 93:3416–3421 [1996]). However, prior to the development of the present invention, the histidine kinase system of *N. crassa* and the medically important fungus *C. albicans* were not known.

In the most simple form of the histidine kinase system, the first component is an autophosphorylating histidine kinase, the activity of which is modulated in response to a specific stimulus; the second component is a response regulator. This response regulator serves as a substrate for the histidine kinase. An aspartate residue of the regulator becomes phosphorylated after phosphoryl transfer from the histidine residue of the kinase. It is the phosphorylation of the response regulator that controls its function. The kinase domain is comprised of a module of approximately 250 amino acids with five sequence blocks that are conserved (H, F, G1, G2, and N). The H box is the site of histidine autophosphorylation, while the F, G1 and G2 boxes are believed to be involved in nucleotide binding; the function of the N box is unknown. The response regulator domain ("response regulator," "D box," or "receiver domain") may be identified from the number and spacing of a module of conserved aspartate, lysine, and hydrophobic residues in a module of approximately 120 amino acids. These two signaling modules (i.e., the histidine kinase and response regulator) may be found in various contexts within more complex signalling proteins.

Fungal Histidine Kinases

With the exception of plants, in eukaryotes examined to date, the histidine kinase and response regulator activities reside in the same protein. Fungal two-component systems have been identified that are sensitive to extracellular osmolarity fluctuations. Under appropriate conditions, an enzymatic cascade is activated and cell wall biosynthesis is stimulated. This response is critical, as fungal cells that are incapable of adjusting to changes in extracellular osmolarity are nonviable (See, L. Alex and M. Simon, Trends Genet., supra; and B. Morgan et al., J. Cell Biol., 5:453–457 [1995]). Fungal pathogens must be able to quickly respond (i.e., via glycerol synthesis and cell wall biosynthesis) to changes in osmolarity found in various tissues.

In *S. cerevisiae* the Sln1p/Ypd1p/Ssk1p proteins comprise a two-component signal transduction pathway that regulates the Hog1 MAPK cascade (F. Posas et al., Cell 86:865–875 [1996]). The HOG1 pathway is responsible for the control of genes necessary for adaptation to high external osmolarity. The Sln1p/Ypd1/Ssk1 pathway is actually a special form of the two-component system known as a phosphorelay system (See, Appleby et al., Cell 86:845–848 [1996], for review). Examples of these systems are found in bacteria where they mediate sporulation in *Bacillus subtilis* (D. Burbulys et al., Cell, 64:545–552 [1991]) and transcription of virulence factors in *Bordetella pertussis* (M. Uhl and J. Miller, EMBO J., 15:1028–1036 [1996]). The phosphorelay system involves a set of multiple phosphotransfer reactions alternating between histidine and aspartate. For example, autophosphorylation of the histidine kinase occurs (e.g., at the "H1" site) and there is subsequent transfer to an aspartate residue ("D1"). This aspartate can lie in the same protein as the kinase (as in the case of BvgS in *B. pertussis*) or it can be a separate protein (as in the case of SpoOF in *B. subtilis*). There is then transfer from the aspartate (D1) to a second histidine residue ("H2"). The H2 site can be within the same protein as the first site (e.g., BvgS) or in a separate protein (e.g., SpoOB). Finally there is transfer from the histidine at H2 to another aspartate residue ("D2"). Generally, D2 is in a separate response regulator that is the protein that has some function such as DNA binding.

In the *S. cerevisiae* pathway, the Sln1p is an osmosensing transmembrane histidine kinase. Under conditions of low osmolarity, Sln1p first autophosphorylates a histidine residue (H1) and this phosphate is transferred to an internal aspartate residue (D1). Phosphate is then tranferred from the D1 site of Sln1p to a histidine (H2) on a small protein called Ypd1p. Finally, the phosphoryl group is transferred to yet another protein, the response regulator Ssk1p (D2). Phosphorylation of Ssk1p results in a protein that cannot activate the HOG1 pathway (i.e., Sln1p is a negative regulator of the HOG1 pathway). Under conditions of high osmolarity, Sln1p is inhibited, resulting in dephosphorylation of Ssk1p which can now activate the HOG1 cascade to allow activation of multiple osmolarity responses (See, B. Morgan et al., J. Cell. Biol., 5:453–457 [1995]; and F. Posas et al., Cell 86:865–875 [1996]). Mutants with sln1 and hog1 deletions are non-viable under conditions of high osmolarity, while constitutive hog1 mutants are non-viable under conditions of low osmolarity.

The Skn7p is another response regulator found in *S. cerevisiae*. So far, the cognate histidine kinase for Skn7p has not been found. (Although it is known from the completed genome project of *S. cerevisiae*, that Sln1p is the only two-component histidine kinase in this organism.) The skn7 gene was isolated as a suppressor of kre9, a mutant defective in (1-6) β-glucan synthesis (See, J. L. Brown et al., EMBO 13:5186–5194 [1994]; and J. L. Brown et al., J. Bacteriol., 175:6908–6915 [1993]). This gene is also known as "pos9," identified as a gene important for the adaptation of yeast to oxidative stress (See e.g., B. Krems et al, Curr. Genet., 29:327–334 [1996]). It has also been linked to a potential transcription factor Ask10 (See, Page et al., Yeast 12:267–272). The skn7 protein (skn7p) has been shown to share homology to DNA-binding motifs, sln1p, and a putative receiver domain (See, J. Morgan et al, J. Cell. Biol., 5:453–457 [1995]; J. L. Brown et al, EMBO, supra; and J. L. Brown et al., J. Bacteriol., supra).

In addition, skn7p has been shown to be phosphorylated in vivo, an observation that is consistent with the inclusion of a receiver domain. The role of skn7, hog1, and the histidine kinases that activate them make them attractive targets for anti-fungal compounds. However, prior to the development of the present invention, insufficient information was available regarding the distribution of histidine kinases in fungi of medical significance (e.g., *C. albicans*), and mammals such as humans.

An alternative osmosensor of the hog1 pathway has also been identified. The gene sho1 (synthetic high osmolarity sensitive) encodes a protein of 367 amino acids with homology to SH3-containing signal transduction proteins (e.g., GRB2, c-scr, and PLCγ). Sho1p is believed to be localized in the plasma membrane, and activates the MAPKK (MAP kinase kinase) pbs2p, by phosphorylation of pbs2p at $Ser^{514}$ and $Thr^{518}$. However, sho1p appears to have a minor role in the regulation of the hog1 pathways, as sho1p is not able to compensate for sln1p mutations.

*N. crassa* and *C. albicans* Histidine Kinase Systems

In a preferred embodiment, the osmotic-1 (cos-1) gene encoding the histidine kinase of *C. albicans* is provided. In alternative embodiments, the os-1 gene encoding the histidine kinase of *N. crassa* is provided. However, it is contemplated that other osmosensing fungal, as well as other histidine kinases with homology to the *C. albicans* histidine kinase can be identified using the sequence information and methods provided herein.

In preliminary experiments during the development of the present invention, *N. crassa* was used, as it is particularly well-suited to the study of fungal cell wall assembly. This organism has been "domesticated" and methods have been developed to manipulate the organism in the laboratory. *N. crassa* exhibits both an asexual vegetative and a sexual phase in its life cycle (See e.g, M. L. Springer, BioEssays 15:365–374 [1993]). During vegetative growth, *N. crassa* forms a branched multicellular network of hyphae (i.e., a mycelium). Hyphae extend from the apical tip and form branches at regular intervals, often fusing with other hyphae. Upon conditions of nutrient deprivation and desiccation, the mycelium sends up aerial hyphae, which then differentiate into conidiophores that, in turn, ultimately produce conidia, which can also function as male gametes during the sexual cycle. *N. crassa* forms microconidia, as well as macroconidia. The microconidia are uninucleate and may be crossed in such a manner that only monokaryons are involved. The macroconidia are multinucleate, with an average of three nuclei per macroconidium. When placed in a suitable environment, populations of macroconidia proceed synchronously through germination, including the de novo synthesis of cell wall material.

In order to address the suitability of using the fungal histidine kinase pathway as a target for development of antifungals, experiments were conducted to analyze the osmotic sensitivity and other characteristics of *N. crassa*. Osmotically-sensitive mutants of *N. crassa* are unable to grow in liquid media supplemented with 4% NaCl. Four osmotic genes (os) within *N. crassa* have been identified (designated as os-1, os-2, os-4, and os-5). The os-1 strains have altered cell wall compositions containing decreased amounts of alkali-soluble glucose, are morphologically abnormal, and produce few macroconidia.

In addition, *N. crassa* strains with a temperature-sensitive allele of os-1 form protoplasts (i.e., cells lacking cell walls), when grown in specialized media at non-permissive temperature (e.g., 37° C.). In these cultures, both (1-3)β-glucan and chitin biosynthesis occurred, but the polymers were excreted into the medium, rather than being assembled into a cell wall. Thus, os-1 mutants are not defective in (1-3)β-glucan or chitin synthases. When the growth temperature is shifted to 25° C. (i.e., a permissive temperature for os-1 function), the cell wall-less (i.e., protoplast) populations regenerate cell walls, and grow in the form of hyphae. Each of the identified os mutant was tested; it was determined that only os-1 strains can form protoplasts that grow and divide. These results indicated that os-1 has a fundamental and essential role in fungal cell wall assembly.

Next, the os-1 gene was localized to a member of the ordered Vollmer-Yanofsky cosmid library (S. Vollmer and C. Yanofsky, Proc. Natl. Acad. Sci., 83:4861 [1986]). The original cosmid clone containing the os-1 gene was then isolated, cloned and sequenced. A single open reading frame (ORF) of approximately 4.3 kb interrupted by four introns was identified. The ORF was found to encode a predicted protein of 1298 amino acids (Alex et al., Proc. Natl. Acad. Sci., 93:3416–3421 [1996]). Gene replacement experiments were used to confirm that the ORF encodes the os-1 protein. In subsequent experiments, the predicted os-1 protein was shown to have significant homology to bacterial and yeast signal transduction two-component histidine kinases (See, FIG. 6). The sequence analysis identified three areas of significant homology corresponding to the H box, ATP-binding site, and D box.

The os-1 cognate of *C. albicans* (cos-1) was of particular interest. This protein shows 60% identity and 70% similarity with os-1. Indeed, the H box sequence is identical for these proteins.

Experiments were also conducted to determine whether cognates of skn7 are present in pathogenic fungi. In these experiments, PCR was conducted using primers capable of amplifying skn7-specific DNA. DNA from various sources was used as template (e.g., *C. albicans, A. fumigatus,* and human). The results indicated that cognates of *S. cerevisiae* are present in *C albicans* and *A. fumigatus,* but not in humans.

Utility of Fungal Histidine Kinase Systems

The results obtained during the development of the present invention indicated that the skn7 and os-1 (or cos-1) systems are suitable targets for antifungals. In addition, it was determined that a portion of the skn7p (residues 420–434; based upon the numbering system of J. L. Brown et al, J. Bacteriol., 175:6908–6915 [1993]) was homologous to certain D-box domains of os1p (residues 1129–1143), sln1p (residues 1137–1151), and BarA (residues 711–725). Thus, it is contemplated that compounds based on the skn7p D-box domain have utility in the development of antifungals.

Additional potential targets for development of antifungals include the receiver domains of proteins that receive the phosphoryl group transferred from the phosphorylated aspartate residue of the histidine kinase domain. For example, it is contemplated that peptides that mimic portions of the D-box or receiver domain of ssk1p (See e.g., T. Maeda et al., Nature 369:242–245 [1994]) will find use in methods using the present invention.

It is contemplated that compositions of the present invention can be used in assays to detect compounds of potential use as antifungals. In one embodiment, the assays incorporate target substrates that mimic regions of the H-box and/or D-box domains of the histidine kinase of interest, or the receiver domain (i.e., D-box) of the receiver protein. In particular, the present invention contemplates assays for os1p, its cognates, and other histidine kinases with homologous D-box or H-box domains. Thus, it is not intended that the assay systems be limited to any particular system or fungal species.

It is further contemplated that various assay systems can be used to screen for antifungal compounds, including, but not limited to immunoassays (i.e., radioimmunoassay [RIA], immunofluorescence [IFA], enzyme-linked immunosorbent assay [ELISA or EIA]), as well as chemiluminescent, immunohistochemical, and other methods, including precipitation, agglutination, complement fixation, and any other assay system suitable for such use.

It is also contemplated that assays based on molecular biology can be utilized with the present invention. For example, it is intended that assays using reagents such as anti-sense constructs will be used in the development of antifungals (i.e., therapeutics). Thus, it is contemplated that antisense oligonucleotides directed against one or more portion of the histidine kinase domain are useful as antifungals. Such antisense oligonucleotides may be transformed into fungal cells (e.g., *C. albicans*) to produce cultures that are incapable of growing due to defects in cell wall biosynthesis.

From the previous discussion it is apparent that the present invention solves a need in the art for compositions and methods for development of therapeutics as well as screening methods for identification of useful therapeutics against organisms such as *C. albicans,* as well as other pathogenic and opportunistic fungi and bacteria.

DEFINITIONS

To facilitate understanding of the invention, a number of terms are defined below.

The term "sample" as used herein refers to any type of material obtained from humans or other animals (e.g., any bodily fluid or tissue), cell or tissue cultures, cell lines, or a culture of microorganisms. "Sample" also encompasses food and feed (whether solid or liquid), media (whether solid or liquid) for the growth and maintenance of microorganisms and cell cultures, equipment and its components (e.g., dialysis, intravenous, and nasogastric tubing), disposable, as well as reusable patient care items (including catheters), environmental surfaces, soil, water and other fluids, and reagents (e.g., buffers).

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g, humans).

As used herein, the term "antimicrobial" is used in reference to any compound which inhibits the growth of, or kills microorganisms, including eukaryotes such as fungi (i.e., it includes antifungals). It is intended that the term be used in its broadest sense, and includes, but is not limited to compounds such as antibiotics which are produced naturally or synthetically. It is also intended that the term includes compounds and elements that are useful for inhibiting the growth of, or killing microorganisms.

As used herein, the term "antimetabolite" refers to any substance with a close structural resemblance to another, essential substance (i.e., metabolite) that is required for normal physiologic function. Typically, antimetabolites exert their effects by interfering with the utilization of the essential metabolite.

As used herein, the term "polyploid" refers to cells or organisms which contain more than two sets of chromosomes.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, "amino acid sequence" as used herein refers to peptide or protein sequence. "Peptide nucleic acid" as used herein refers to an oligomeric molecule in which nucleosides are joined by peptide, rather than phosphodiester, linkages. These small molecules, also designated anti-gene agents, stop transcript elongation by binding to their complementary (template) strand of nucleic acid (Nielsen et al., Anticancer Drug Des., 8:53–63 [1993]).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, naturally occurring sequences.

A "substitution" results from the replacement of one or more nucleotides or amino acids by different nucleotides or amino acids, respectively.

As used herein, the term "purified" or "to purify" refers to the removal of contaminants from a sample. As used herein, the term "substantially purified" refers to molecules, either nucleic or amino acid sequences, that are removed from their natural environment, "isolated" or "separated," and are at least 60% free, preferably 75% free, and most preferably 90% free from other components with which they are naturally associated. An "isolated polynucleotide" is therefore a substantially purified polynucleotide.

As used herein, the term "probe" refers to an oligonucleotide (i.e., a sequence of nucleotides), whether occurring naturally as in a purified restriction digest or produced synthetically, which is capable of hybridizing to another oligonucleotide or polynucleotide of interest. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is further contemplated that the oligonucleotide of interest (i.e., to be detected) will be labelled with a reporter molecule. It is also contemplated that both the probe and oligonucleotide of interest will be labelled. It is not intended that the present invention be limited to any particular detection system or label.

As used herein, the term "target" refers to the region of nucleic acid bounded by the primers used for polymerase chain reaction. Thus, the "target" is sought to be sorted out from other nucleic acid sequences. A "segment" is defined as a region of nucleic acid within the target sequence.

"Amplification" is defined as the production of additional copies of a nucleic acid sequence and is generally carried out using polymerase chain reaction (PCR) or other technologies well known in the art (e.g., Dieffenbach and Dveksler, *PCR Primer, a Laboratory Manual,* Cold Spring Harbor Press, Plainview N.Y. [1995]). As used herein, the term "polymerase chain reaction" ("PCR") refers to the method of K. B. Mullis (U.S. Pat. Nos. 4,683,195 and 4,683,202, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "polymerase" refers to any polymerase suitable for use in the amplification of nucleic acids of interest. It is intended that the term encompass such DNA polymerases as Taq DNA polymerase obtained from *Thermus aquaticus,* although other polymerases, both thermostable and thermolabile are also encompassed by this definition.

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for insertion into recombinant vectors.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "nested primers" refers to primers that anneal to the target sequence in an area that is inside the annealing boundaries used to start PCR. (See, K. B. Mullis, et al., Cold Spring Harbor Symposia, Vol. LI, pp. 263–273 [1986]). Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers. As used herein, the term "amplification reagents" refers to those reagents (deoxyribonucleoside triphosphates, buffer, etc.), needed for amplification except for primers, nucleic acid template and the amplification enzyme.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding, the probe will not hybridize to the second non-complementary target.

The art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions. The term "hybridization" as used herein includes "any process by which a strand of nucleic acid joins with a complementary strand through base pairing" (Coombs, *Dictionary of Biotechnology*, Stockton Press, New York N.Y. [1994].

"Stringency" typically occurs in a range from about $T_m-5°$ C. (i.e., 5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridisation, in *Nucleic Acid Hybridisation* [1985]). Other references include more sophisticated computations which take structural as well as sequence characteristics into account for the calculation of $T_m$.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH [fluorescent in situ hybridization]).

As used herein, the term "antisense" is used in reference to nucleic acid sequences which are complementary to a specific nucleic acid sequence (e.g., mRNA that is complementary to another RNA sequence). Antisense DNA or RNA may be produced by any method, including synthesis by splicing the gene(s) of interest in a reverse orientation to a viral promoter which permits the synthesis of a coding strand. Once an antisense RNA is introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein the term "portion" when in reference to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:18," encompasses the full-length Candida histidine kinase protein and fragments thereof.

the term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A", the presence of a protein containing epitope A (or free, unlabelled A) in a reaction containing labelled "A" and the antibody will reduce the amount of labelled A bound to the antibody.

The term "sample" as used herein is used in its broadest sense. A biological sample suspected of containing nucleic acid encoding histidine kinase may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

"Alternations in the polynucleotide" as used herein comprise any alteration in the sequence of polynucleotides encoding histidine kinase, including deletions, insertions, and point mutations that may be detected using hybridization assays. Included within this definition is the detection of alterations to the genomic DNA sequence which encodes histidine kinase (e.g., by alterations in the pattern of restriction enzyme fragments capable of hybridizing to any sequence such as SEQ ID NOS:1, 3, 5, 7–10, or 14–17 [e.g., RFLP analysis], the inability of a selected fragment of any sequence to hybridize to a sample of genomic DNA [e.g., using allele-specific oligonucleotide probes], improper or unexpected hybridization, such as hybridization to a locus other than the normal chromosomal locus for the histidine kinase gene (e.g., using FISH with metaphase chromosomes spreads, etc.]).

A "variant" in regard to amino acid sequences is used to indicate an amino acid sequence that differs by one or more amino acids from another, usually related amino acid. The variant may have "conservative" changes, wherein a substituted amino acid has similar structural or chemical properties (e.g., replacement of leucine with isoleucine). More rarely, a variant may have "non-conservative" changes, (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software. Thus, it is contemplated that this definition will encompass variants of histidine kinase. Such variants can be tested in functional assays, such as growth inhibition assays.

The term "derivative" as used herein refers to the chemical modification of a nucleic acid encoding histidine kinase structures. Illustrative of such modifications would be replacement of hydrogen by an alkyl, acyl, or amino group. A nucleic acid derivative would encode a polypeptide which retains essential biological characteristics of naturally-occurring histidine kinase.

As used herein, the term "host cell" refers to any cell capable of expressing a functional gene and/or gene product introduced from another cell or organism. This definition includes the *S. cerevisiae* expression vector used to express *C. albicans* histidine kinase.

As used herein, the term "antifungal chemotherapeutic" refers to any substance or agent used in the treatment of fungal disease, infection or colonization. It includes fungicidal as well as fungistatic compounds which act on fungi in vitro, as well as in vivo.

As used herein, the term "osmosensing histidine kinase" refers to an enzyme that acts as a signal transduction histidine kinase. In particular, the term refers to histidine kinases that are components in two-component signal transduction systems. It is contemplated that the term encompass histidine kinases that are involved in various cell functions, including but not limited to small and/or large porin synthesis, osmolarity responses, cell wall assembly, etc.

EXPERIMENTAL

The following examples are provided in order to demonstrate and further illustrate certain preferred embodiments and aspects of the present invention and are not to be construed as limiting the scope thereof.

In the following disclosure, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); °MW (molecular weight); °C. (degrees Centigrade); OD (optical density); EDTA (ethylenediamine-tetracetic acid); EGTA (ethyleneglycol-bis-(β-aminoethyl ether)); SDS (sodium dodecyl sulfate); PAGE (polyacrylamide gel electrophoresis); UV (ultraviolet); bp (base pair); kb and kbp (kilobase pairs); YPD (yeast extract, Bacto-peptone and dextrose medium); PTC (40% polyethelene glycol 3300 [Sigma], 50 mM Tris-HCl pH8.0, and 50 mM $CaCl_2$); 0.05 M Pipes, pH 6.5 (0.05 sodium phosphate, 0.001 M EDTA, 0.1 M NaCl, 5% NaCl; IETGN buffer (20 mM imidazole-HCl pH 6.8, 1 mM EDTA, 1 mM EGTA, 12 mM monothioglycerol, 20% glycerol, 100 mM sodium chloride); KTED (0.3 M KCl, 0.01 M Tris-HCl, pH 7.4, 0.001 M EDTA, 0.001 M dithiothreitol); μg/ml (microgram per milliliter); mm (millimeter);×g (times gravity); HPLC (high pressure liquid chromatography)1; DDT (dithiothreitol); PMSF (phenylmethylsulfonyl fluoride); KGlu (potassium glutamate); SSC (salt and sodium citrate buffer); SDS (sodium dodecyl sulfate); PAGE (polyacrylamide gel electrophoresis); Waters (Waters Corp., Milford, Mass.); Promega (Promega Corp., Madison, Wis.); BioRad (Bio-Rad Laboratories, Hercules, Calif.); NEB (New England Biolabs, Beverly, Mass.); USB (United States Biochemical, Cleveland, Ohio); Quiagen (Quiagen, Inc., Chatsworth, Calif.); Applied Biosystems (Perkin Elmer/Applied Biosystems, Foster City, Calif.); DIFCO or Difco (Difco Laboratories, Detroit, Mich.); GENSET (San Diego, Calif.); Wisconsin Genetics Computer Group (GCG) package; BRL (GIBCO BRL, Gaithersburg, Md.); Kodak (Eastman Kodak, Rochester, N.Y.); FGSC (Fungal Genetics Stock Center, Kansas City, Kans.); Dupont (Dupont, Wilmington, Del.); Fisher (Fisher Scientific, Pittsburg, Pa.); Cornell (Cornell University, Ithaca, N.Y.); Intelligenetics (Intelligenetics, Campbell, Calif.); GCG (Wisconsin Genetics Computer Group, University of Liverpool, U.K.); and Gene Codes (Gene Codes, Ann Arbor, Mich.).

The restriction enzymes used in these experiments are available from various sources, including NEB. Fungal media, such as Sabouraud's dextrose broth and agar are available from suppliers such as Difco.

EXAMPLE 1

In this Example, *Neurospora crassa* was grown and used as a source of DNA for identification of the histidine kinase gene. The *E. coli* strains and the plasmids used in subsequent experiments are also described.

A. Fungal and Bacterial Strains

Various *N. crassa* strains were obtained from FGSC, including wild-type (74-OR8-1a), os-1 (B135), os-1 (P3282), os-1 (UCLA-80), os-4 (NM2010), os-5 (NM2160), and cut (LLMI). In addition, an os-1 (NM233t) nic-1 strain was constructed by crossing a temperature-sensitive osmotic mutant os-1 (NM233t) with nic-1 (S1413a) (See, Selitrennikoff et al., Exp. Mycol., 5:155–161 [1981]). In order to isolate an os-1$^+$-containing fragment smaller than 9.3 kb, several DNA fragments were subcloned and assayed for complementation of os-1 (NM233t) nic-1.

The stock strains were grown at 25° C., on solidified Vogel's medium N (See e.g., Davis and deSerres, Meth. Enzymol., 27A:79–143 [1970]), containing sucrose (1.5% w/v) ("VMS" medium). Strains that required nicotinamide were grown on media supplemented with nicotinamide (10 μg/ml)("VMSN mediums). Benomyl (Dupont) was added to cooled (i.e., 45° C.) VMSN medium to a final concentration of 1 μg/ml. Osmotic mutants of *N. crassa* grown on slants of agar-solidified VMS had altered morphologies, appearing as dense, cropped mycelia, as compared with wild-type. The altered morphology was particularly apparent with the cut mutant. In addition, bright orange spots appearing as pockets of "liquid exudate" (i.e., as described by Grindle and Dolderson, Trans. Brit. Mycol. Soc., 87:457–487 [1986]) were observed with osmotic mutants.

In liquid VMSN, hyphae from each of the os mutants was similar to wild-type. However, when grown in VMSN medium supplemented with 4% (w/v) NaCl, the osmotic mutants had irregularly shaped hyphae compared to wild-type, and some hyphae resembled pseudoconidia. These observations indicated that the osmotic genes are important in the maintenance of normal cell morphology of N. crassa grown in media with high osmolarity levels.

E. coli strains XL-1 Blue and TB-1 (Stratagene) were maintained on LB medium (See e.g., Sambrook et al.,(eds.) Molecular Cloning: A Laboratory Manual, Cold Spring Harbor Laboratory Press, Cold Spring Harbor, N.Y., [1989]).

B. Plasmids

Plasmid (pMO63), containing an allele of tub-2 that confers benomyl resistance as a 3.1 kb HindIII DNA fragment in pUC118 was used. pCE1 was constructed by self-ligation of a 13 kb HindIII DNA fragment of cosmid 12:4 D (Vollmer-Yanofsky genomic library; See, Vollmer and Yanofsky, Proc. Natl. Acad. Sci., 83:4869–4873 [1989]). The 12:4D cosmid contained approximately 35 kb of DNA that functionally complemented an os-1 mutant, as shown in FIG. 1. This cosmid was digested with a variety of restriction enzymes and the digests were used to transform competent os-1 (NM233t) nic-1 cells.

Figure 4:
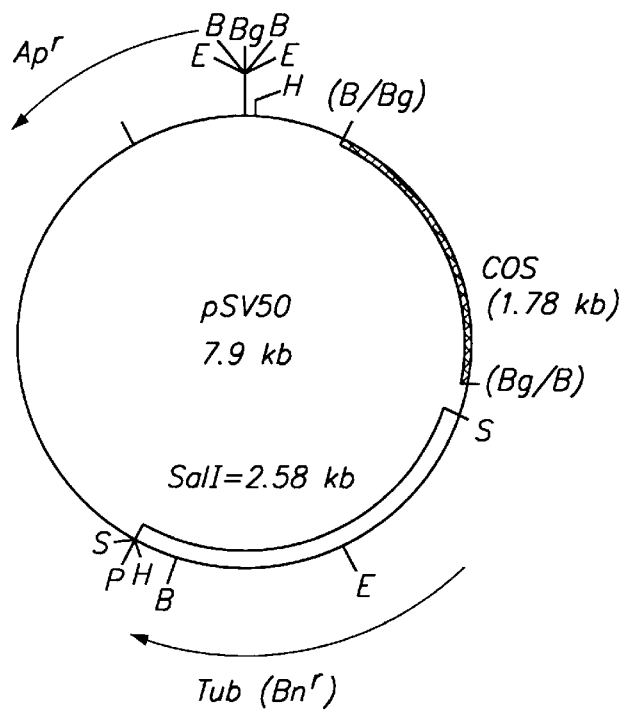
FIG. 4 is a map of pSV50.

A cosmid vector, pSV50 that confers benomyl resistance was used to construct the N. crassa genomic DNA library (See, FIG. 4; Orbach et al., Mol. Cell. Biol., 6:2452–2461 [1986]; and Vollmer and Yanofsky, supra). pCE1 contained an ampicillin resistance gene, the origin of replication from pSV50 (originally derived from pBR322), and 9.3 kb of genomic N. crassa DNA sequence. A NotI/HindIII deletion of pCE1 ("pCE5") containing a 6.5 kb EcoR1/NotI (the EcoR1 site is in the polylinker of pCE1 adjacent to a Sau3AI site) DNA fragment of pCE1 inserted into a pBluescript SK⁻ (Stratagene), was created, as well as the plasmid "pCE6." The pCE6 plasmid contained a 2.8 kb NotI/HindIII DNA fragment subcloned from pCE1. Two additional plasmids, were also created. The plasmid "pMMS100" contained a 7.0 kb EcoR1/SmaI DNA fragment subcloned from pCE1 into pBluescriptSK⁻, while the plasmid "pMMS108" is a partial XhoI deletion of pMMS100 that contained a 4.6 kb XhoI/SmaI DNA insert in Bluescript SK⁻.

EXAMPLE 2

In this Example, competent N. crassa spheroplasts were created from the strains and DNA described in Example 1. First, the os-1 gene was isolated from the Vollmer-Yanofsky N. crassa genomic library by a chromosome walk. (Vollmer and Yanofsky, supra). Cosmid "12:4D" containing approximately 35 kb of DNA functionally complementing an os-1 mutant was identified. Cosmid 12:4D DNA was digested with various restriction enzymes, and these digests were used to produce competent os-1(NM233t) nic-1 cells.

DNA-mediated transformations were accomplished using the method of Selitrennikoff and Sachs (Selitrennikoff and Sachs, Fungal Genet. Newsl., 38:92 [1991]). In this experiment, competent os-1 (NM233t), nic-1, and os-1 (B135) cells were transformed with the cosmid 12:4D, or co-transformed with subclones of 12:4D and pSV50 or pM063 at a molar ratio of approximately 5:1, respectively.

As direct selection of transformants was not possible on 4% (w/v) NaCl medium (VMSN containing 1.5% sucrose) transformant colonies were initially selected for benomyl resistance.

Briefly, the DNA was premixed with heparin (25 μl of a 125 μg solution), to which 0.1 ml of a spheroplast (approximately 5×10⁷ cells) preparation were added and, the mixtures were incubated on ice for 30 minutes. Lipofectin (3.5 μg/ml) was added, and incubation continued for 15 minutes at room temperature. Then, 1 ml of PTC was added, gently mixed, and the suspensions were incubated 20 minutes at room temperature. The suspensions were added to VMSN media containing benomyl, incubated for 2–3 days, and then transferred to solid VMSN slants containing 4% (w/v) NaCl, and grown for 2–3 days. Control VMSN slants that did not contain NaCl were also inoculated and incubated. Complementation of the os-1 mutant salt-sensitive phenotype was then scored. Transformants of the temperature-sensitive os-1 mutants were grown at 37° C., while transformants of the non-temperature sensitive os-1 mutant were grown at 26° C.

Introduction of a HindIII digest of 12:4D DNA into os-1 (NM233t) nic cells resulted in the production of several transformants that grew in a manner similar to wild-type on NaCl-supplemented media at 37° C., suggesting that HindIII did not cut within the functional os-1⁺ gene. Subsequently, a HindIII fragment of 12:4D was subcloned as "pCE1" (described in Example 1). pCE1 contained a 9.3 kb genomic DNA fragment that complemented the os-1 mutant (See, FIG. 1). FIG. 1 illustrates the subcloning of os-1⁺ by functional complementation. In this Figure, subclones are indicated as an expanded region of the cosmid 12:4D. FIG. 1 also shows that pCE1 was not able to complement os-1. In addition, a NotI/HindIII DNA deletion of pCE1 (pCE5) was not able to complement os-1. Furthermore, the pCE6 clone (i.e., a cloned NotI/HindIII DNA fragment) did not complement the os-1 mutant, suggesting that the NotI site is within a functional part of the os-1⁺ gene. However, a SmaI/HindIII deletion of pCE1 (i.e., "pMMS100") complemented os-1 NM233t) nic-1, whereas a partial XhoI deletion of pMMS100 ("pMMS108") did not complement, suggesting that the os-1⁺ gene is contained within the 7.0 kb Sau3A/SmaI genomic DNA fragment of pMMS100. In addition, transformation of a non-temperature sensitive mutant os-1 (B135) with pMMS100 resulted in complementation of the salt-sensitive phenotype.

The results of these experiments indicated that a functional os-1⁺ gene was encoded on the genomic fragment contained in pMMS100. In order to provide additional data to support this conclusion, the growth (i.e., the linear growth rate) of pMMS100 transformants, os-1 mutants, and wild-type were quantitated on agar-solidified medium with and without 4% (w/v) NaCl in race tubes (See, Davis and deSerres, Meth. Enzymol., 27A:79–143 [1970]), containing agar-solidified VMSN medium supplemented with 4% (w/v) NaCl as needed. The race tubes were constructed from 25 ml disposable pipets (e.g., Fisher) according to the method of White and Woodward (White and Woodward, Fungal Genet. Newsl., 42:79 [1995]). Growth distances were measured relative to the origin of inoculation after 16, 24, 40, 48, and 64.5 hours of incubation at 37° C. Plots of the linear growth distance showed that the growth rates of wild-type, os-1 mutants, and pMMS100-transformed os-1 mutants were essentially identical on media without NaCl. However, on media supplemented with 4% (w/v) NaCl, pMMS100-transformed os-1 mutants showed a restored osmotolerant phenotype, as evidenced by 18- to 26-fold differences between the growth rates of the recipient strains, os-1 (NM233t) nic-1 and os-1 (B135), and the pMMS100-transformed strains (MMS100t-16 and MMS100b-2). These results indicated that a functional os-1+ gene was located on the 7 kb genomic fragment of pMMS100.

EXAMPLE 3

Figure 2:
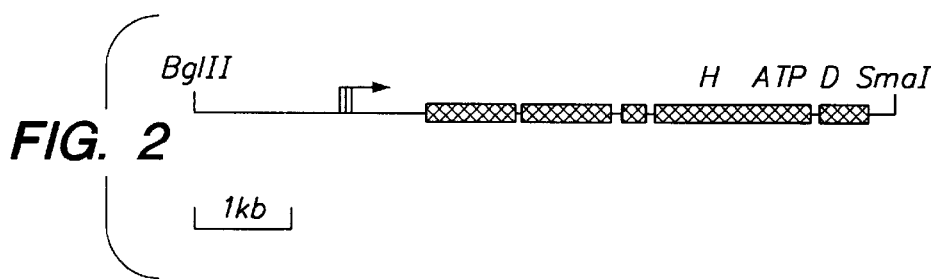
FIG. 2 is a schematic of the *N. crassa* os-1 open reading frame.

In this Example, the DNA sequence of the *N. crassa* os-1 was determined. Approximately 6.5 kb of the 7.0 kb DNA fragment of pMMS100 was sequenced on both strands from restriction sites BglII to SmaI, as shown in FIG. 2. DNA sequencing and primer syntheses were done by DNA Services (Cornell). Sequence analyses were performed using MacVector™ (Kodak), the basic local alignment search tools, BLAST (S. F. Altschul et al., J. Mol. Biol., 215:403–410 [1990]; PROSITE (A. Bairoch, Nucl. Acids Res., 21:3097–3103 [1993]); and P/C Gene (Intelligenetics). The os-1+ DNA nucleotide and deduced Os1p amino acid sequences have been deposited with GenBank (accession number: U53189)(SEQ ID NOS:1 and 2, respectively).

Nucleotide sequence analysis indicated a predicted open reading frame (ORF) of approximately 4.1 kb, interrupted by four introns as shown in FIG. 2. The os-1 start of translation was identified by sequence similarity to an *N. crassa*-specific start of translation consensus sequence (i.e., Kozak sequence). Similarly, introns were identified by searching for *N. crassa*-specific intron consensus sequences (See e.g., J. J. P. Bruchez et al., Fungal Genet. Newsl., 40:89–96 [1993]). The introns ranged in size from 53–66 base pairs. Three sets of sequences that were similar to the *N. crassa*-specific start of transcription consensus sequence were identified 714–881 base pairs upstream of the predicted start of translation, as indicated by the arrow in FIG. 2. Also in FIG. 2, predicted exons are indicated as large rectangles, while introns are indicated as gaps between the rectangles, the H-box, D-box, and ATP-binding motif are also indicated.

Translation of the ORF predicted a 1298 amino acid protein (Os1p), with a molecular weight of approximately 142 kDa, and a calculated pI of 5.3. A BLAST comparison of Os1p with protein sequences in several databases indicated similarity with sensor histidine kinases of bacteria and yeast (described in Example 4, below).

FIG. 3 shows an amino acid sequence alignment of Os1p with BarA (bacterial adaptive response) of *E. coli* (See, Nagasawa et al., Mol. Microbiol., 6:799–807 [1992]), RepA (required from production of extracellular enzymes) of *Pseudomonas viridflava* (C.-H. Liao et al., Mol. Plant-Microbe Interact., 7:391–400 [1994]), ApdA (antibiotic production) of *Pseudomonas fluorescens* (N. Corbell and J. E. Loper, J. Bacteriol., 177:6230–6236 [1995]), and Sln1p of *Saccharomyces cerevisiae* (I. M. Ota and A. Varshavsky, Science 262:566–569 [1993]). In this Figure, the sequence alignments are shown based on data obtained with BLAST, MacVector, and PC/Gene analysis tools. Shaded areas indicate sequence identities; while diamonds (♦) at Os1p His$^{718}$ and Asp$^{1136}$ indicate the presence of putative phosphoryl group acceptors; underlined sequences indicate hydrophobic regions in Os1p, BarA, ApdA, and Sln1p, filled circles (●) and open triangles(Δ) indicate Os1p h- and c-regions, respectively, of a potential signal sequence. The arrow indicates a potential signal peptidase cleavage site.

As shown, sequence similarity was noted between Os1p and BarA. The overall sequence identity of Os1p with BarA, RepA, and ApdA was found to be approximately 11%, whereas Sln1p shares approximately 7% identity. The following Table provides a comparison of the D-box receiver domains of skn1p, os1p, sln1p, and BarA.

TABLE 2

Comparison of D-Box Receiver Domains

| D-Box Receiver Domain | Sequence | SEQ ID NO: |
|---|---|---|
| skn7p | RYDLVLMDIVMPNLD | SEQ ID NO: 24 |
| os1p | KFDVILMDVQMPIMG | SEQ ID NO: 25 |
| sln1p | NYNMFIMDVQMPKVD | SEQ ID NO: 26 |
| BarA | PFDLILMDIQMPDMD | SEQ ID NO: 27 |

Table 3 shows the regions of homology between the amino acid sequences of Os1p, BarA, RepA, ApdA, and Sln1p.

TABLE 3

Regions of Protein Sequence Homology

| Protein | H-Box | D-Box | ATP-Binding Domain |
|---|---|---|---|
| Os1p | 698–843 | 1093–1203 | 870–931 |
| BarA | 282–427 | 674–782 | 451–512 |
| RepA | 253–398 | 652–763 | 422–483 |
| ApdA | 274–419 | 673–784 | 443–504 |
| Sln1p | 556–703 | 1081–1207 | 859–920 |

For the Os1p regions 698–843, 870–931, and 1093–1203, shared amino acid sequence identity with BarA, RepA, and ApdA was found to be 40%, 45%, and 34%, respectively. The Sln1p sequence identity with Os1p in these regions were 27%, 40%, and 22%, respectively. These three domains are characteristic of histidine kinases and aspartate response regulator modules of signal-transduction proteins that couple environmental signals to adaptive responses (See e.g., B. Morgan et al., Trends Cell. Biol., 5:453–457 [1995]; M. Perego and J. Hoch, Trends Genet., 12:97–101 [1996]; and J. B. Stock et al., Nature 344:395–400 [1990]).

Os1p contains amino acid residues that are conserved among histidine kinases, including the presumed phosphoryl group acceptors His$^{718}$ and Asp$^{1136}$ (See, FIG. 3). As indicated in Table 3, the Os1p region 698 to 843 comprises the H-box domain and the 1093 to 1203 region comprises the D-box domain. Os1p also has a conserved ATP-binding motif that is identical to the motif defined for bacterial and yeast response regulator modules (See, Ota and Varshavsky, supra; Parkinson et al., Ann. Rev. Genet., 26:71–112 [1992]; and Perkins et al., Microbiol. Rev., 46:426–570 [1982]). As described in Examples 6–9 below, the cos-1 gene of *C. albicans* has a high degree of similarity with os-1.

Sln1p, BarA, RepA, and ApdA each have two hydrophobic regions located near the amino terminus that are potential membrane-spanning domains (See, N. Corbell and J. E. Loper, J. Bacteriol., 177:6230–623 [1995]; C.-H. Liao et al., Mol. Plant-Microbe Interact. 7:391–400 [1994]; S. Nagasawa et al., Mol. Microbiol., 6:799–807 [1992]; and I. M. Ota and A. Varshavsky, Science 262:566–569 [1993]). Os1p differs from these regions by having a hydrophobic region at the amino terminus (See, FIG. 3) characteristic of a signal sequence for selective intracellular distribution to the endoplasmic reticulum or the mitochondrial inner membrane (R. H. Davis and F. J. DeSerres, Meth. Enzymol., 27A:79–143 [1970]; and L. M. Gierasch, Biochem., 28:92 [1989]). In addition, Os1p amino acid residues 4–19 contain the hallmarks of a signal sequence (See, L. M. Gierasch, supra), including a central hydrophobic region ("h-region")

and a more polar c-terminal region ("c-region"). Furthermore, between Os1p amino acid residues $A^{18}$ and $V^{19}$, there is a potential signal peptidase cleavage site (See, FIG. 3), that conforms to the −3,−1 rule (See, Davis and DeSerres, supra; G. von Heijne, Nucleic Acids Res., 14: 4683–4690 [1986]; and K. Larsson et al., Mol. Microbiol. 10:1101–1111 [1993]). These observations suggest that the Os1p amino terminal domain (i.e., residues 4–19) is a signal sequence that may initiate intracellular distribution of Os1p.

Additional protein sequence analysis indicated the potential presence of eight potential N-glycosylation sites, one potential tyrosine kinase phosphorylation site ($Tyr^{1028}$), one potential amidation site ($Gly^{1230}$), and one potential cell attachment sequence ($Arg^{196}$-$Gly^{197}$-$Asp^{198}$). Other sites identified include 18 potential protein kinase C phosphorylation sites, 20 potential casein kinase II phosphorylation sites, and 17 potential myristylation sites.

EXAMPLE 4

In this Example, an alternative method for identification of the N. crassa histidine kinase gene was developed.

In these experiments, the N. crassa strain 74-OR23-1VA (mating type A. 74A; no. 2489) obtained from the FGSC was used as the source for purification of genomic DNA and mRNA unless otherwise noted. Genomic DNA for PCR was prepared from isolated N. crassa nuclei. The N. crassa strain used for electroporation is known as "Stadler" (mating type a; characterized as pdx-1his-2Δmtr) obtained from D. Stadler (University of Washington). Handling techniques and growth media for N. crassa are described by Davis and deSerres (R. H. Davis and F. J. deSerres, Meth. Enzymol., 17:79–143 [1970]).

In these experiments, all common molecular biological manipulations were carried out according to standard methods (See e.g., F. M. Ausubel, Current Protocols in Molecular Biology, Wiley, N.Y. [1994]). Reverse transcriptase coupled (RT)PCR was performed as described by J. T. Aatsinki et al., (J. T. Aatsinki et al. BioTechn., 16:282–288 [1994]), except that the primer concentrations were increased to 1.5 μM. Sequencing of DNA templates was done with Sequenase (USB), or by Taq cycle sequencing using dye primer or dye terminator chemistry on an automated sequencer (Applied Biosystems model 373) according to the manufacturer's specifications.

Alignment of histidine kinase members was accomplished using the PILEUP program from the Wisconsin Genetics Computer Group (GCG) package. The following primer to the H box (H1A) was made CA(T/C)GAI(A/T/C)TI(C/A)GIACICICC (SEQ ID NO:7), and served as the forward PCR primer. The reverse primers were synthesized to code for the N box: N1A, GT(A/G)AA(T/C)TTIAIIGC(A/G)TT (SEQ ID NO:8): N2A, GC(A/G)TTIC(T/C)IACIA(G/A)(G/A)TT (SEQ ID NO:9). In these sequences, "I" is deoxyinosine). All primers were purified by electrophoresis through an acrylamide gel (20%/7 M urea) followed by purification over a Sep-Pak $C_{18}$ column. PCR mixtures contained 2.5 μM each primer, 1.4 μg of genomic DNA, 2.5 mM each dATP, dGTP, dCTP, and dTTP in 10 mM Tris-HCl pH 8.3/50 mM KCl/0.001% gelatin/0.5 unit of AmpliTaq (Perkin-Elmer/Cetus) in a total volume of 100 μl. Primers, buffer, and DNA templates were mixed and heated (95° C. for 10 min) in a Perkin-Elmer/Cetus thermocycler and then cooled to 4° C. Nucleotides and polymerase were added and reactions mixtures were cycled 25–30 times at 94° C. (1 min), 40° C. (1 min), and 72° C. (1 min) followed by a 10-min extension at 70° C. Amplification products were purified by electrophoresis through a 1.5% agarose gel, cloned into a T-vector (Promega), and subsequently sequenced. Sequence analysis was done using Sequencher (version 2.1, Gene Codes) and the GCG package. Homology searches and sequence comparisons were performed using the BLASTX and BESTFIT programs of the GCG package.

Genomic and cDNA Cloning of os-1+

Approximately 150,000 clones from a λJ1 genomic library (FGSC) were screened with a randomly primed os-1+ PCR product (Prime-a-gene, Promega) obtained by amplification of N. crassa genomic DNA with the H1A and N2A primers. Positive clones were isolated, digested with BamH1 and grouped by common hybridization patterns. A 5.5-kb BamHI fragment was cloned into BamHI-digested pUC18 to yield pHK1. This clone contained the kinase domain as verified by sequence analysis. pHK1 served as a template for the genomic sequencing of os-1+, which was accomplished by a combination of primer walking, sequencing small subclones, and sequencing deletion subclones in M13 (R. M. Dale et al., Plasmid 13:31–41 [1985]). The genomic sequence of os-1 is shown in SEQ ID NO:5 and os1p is shown in SEQ ID NO:6, while the cDNA sequence of os-1 is shown in SEQ ID NO:3, and os1p is shown in SEQ ID NO:4.

Approximately 106 clones from the Orbach and Sachs cDNA library (Orbach et al., J. Biol. Chem., 265:10981–10987 [1990]; obtained through FGSC) were screened with the os-1+ kinase domain PCR product. Two sets of clones were obtained and designated "M1" and "M10," which started at nucleotides 3285 and 3760 of the genomic sequence, respectively. Both strands of these clones were entirely sequenced. RT-PCR was used to walk upstream of the 5' end of M1 and subsequently clone the entire cDNA coding for os-1+. All RT-PCR products were cloned into a T-vector and sequenced. Primer extension with the oligonucleotide NK45 (GAGAGCTGGCTGATCTGTTG) (SEQ ID NO:10), revealed the transcription start site 969 bases upstream of the initiator AUG of the Os-1 protein (See e.g., SEQ ID NOS:3 and 4; and GenBank U50263).

Analysis of the alignment of several members of the histidine kinase family showed that there is a subclass of kinases that contain both a kinase domain and a response regulator domain, termed "hybrid kinases" (See e.g., L. A. Alex and M. I. Simon, Trends Genet., 10:133–138; R. V. Swanson et al., Trends Biochem. Sci., 19:485–490 [1994]; and J. S. Parkinson and E. C. Kofoid, Ann. Rev. Genet., 26:71–112 [1992]). Two eukaryotic kinases, "ETR1" and "SLN1," are members of this subclass.

Degenerate primers corresponding to the H box consensus (H(E/D)(M/I/L/F)RTP (SEQ ID NO:11) and N box NLV(S/G)NA(I/V)KFT (SEQ ID NO:12) were designed and used to amplify genomic DNA from N. crassa. Two PCR products (designated "nik-1" and "nik-2") were obtained, which upon sequencing were found to encode domains homologous to two-component histidine kinases. Southern blot analysis of genomic DNA from N. crassa with each PCR product showed that each product corresponded to a unique gene. The gene corresponding to the os-$1^{30}$ PCR product was cloned and its function in N. crassa determined.

The os-1+ PCR product was used as a probe to screen N. crassa genomic and cDNA libraries in order to clone the os-1+ gene (See, FIG. 1). The 5' untranslated region is rich in structure and includes an intron of 100 bp. Also, this region is rich in repetitive nucleotide elements, the first of which is the sequence (AGTC)$_6$ ... (GATC)$_6$ (SEQ ID NO:13), which has the possibility of forming a stem-loop structure. Next, the repeat "TACC" is present in tandem 10 times followed shortly by two more repeats. This repeat has also been noticed in the 5' untranslated region of the nit-3$^+$ gene in *N. crassa*, although its significance remains unknown (See, P. M. Okamoto et al, Mol. Gen. Genet., 227:213–223 [1991]). The TACC repeat is followed by a purine-rich segment. The four introns found in os-1$^+$ have consensus splice sites that agree with those found in other genes from *N. crassa* (J. J. P. Bruchez et al., Fungal Genet. Newsl., 40:89–96 [1993]).

Analysis of the predicted amino acid sequence showed that Os1p is a member of the hybrid class of histidine kinases that contain both a kinase and response regulator domain. The starting AUG is contained within the sequence (GCCCACAATCATGAC) (SEQ ID NO:14) consistent with other genes in *N. crassa* (Bruchez et al., Fungal Genet. Newsl., 40:85–88 [1993]). Os1p is most similar to the kinase and regulator regions (57%) of the BarA protein from *Escherichia coli* (S. Nagasawa et al, Mol. Microbiol., 6:799–807 [1992]). The function of BarA is not known, but it can apparently act as a multicopy suppressor in a strain that lacks the osmosensor EnvZ (See, S. Nagasawa et al., supra).

The Os1p protein is novel in that the N-terminal end of the polypeptide contains a unique 90-amino acid motif, which is repeated 5 times, followed by a short sixth truncated repeat. The N-terminal repeat region has a high probability of forming a coiled-coil structure when analyzed with the algorithm of Lupas and Stock (A. Lupas et al., Science 252:1162–1164 [1992]). A computer search using the BLAST program revealed that the N-terminal end of Os1p shares homology [P(N), 1.2×10$^{-6}$] with bacterial sensory transducers, most notably Htr1 which functions to couple sensory rhodopsin to a soluble histidine kinase, and thus regulate phototaxis in *Halobacterium salinarium* (V. J. Yao and J. L. Spudich, Proc. Natl. Acad. Sci., 89:11915–11919 [1992]). Analysis of the distribution of polar and hydrophobic residues in the amino acid sequence of Os1p suggested that the protein is soluble.

EXAMPLE 5

In this Example, the role of os-1$^+$ in development of *N. crassa* was investigated.

RNA Preparation

Total RNA was prepared from *N. crassa* at various stages of development as described by Reinert et al., (W. R. Reinert, Mol. Cell. Biol., 1:829–835 [1981]). For mycelial RNA, cultures were harvested after 8–16 hours of growth in Vogel's 1× liquid medium at 30° C., as described by Davis and deSerres (Davis and deSerres [1970], supra). For germlings, conidia (10 cells per ml) were grown (3 hours at 30° C.) in Vogel's 1× liquid medium. Protoperithecia were prepared by inoculation with a drop of conidial suspension onto a cellophane paper placed on the surface of a Westergaard's plate (See e.g., Davis and deSerres [1970], supra) and growth was allowed to proceed in the light at 25° C., until protoperithecia were visible (approximately 8 days). Cells were scraped from the cellophane and RNA was prepared as described above. All mRNA fractions were purified using Oligotex resin (Qiagen).

Expression of os-1$^+$ was found to be stage specific as the transcript (5.5 kb by Northern analysis) could be detected by RT-PCR of mRNA only during the vegetative phase of *N. crassa* life cycle and not after differentiation into the sexual phase.

Figure 5:
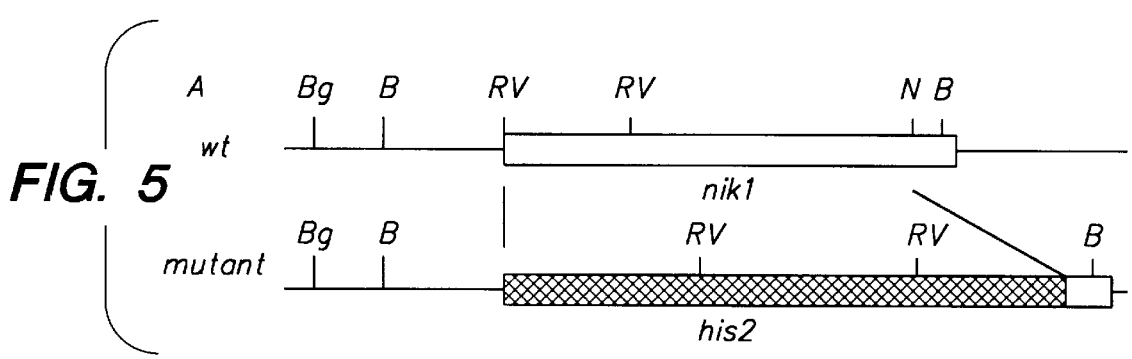
FIG. 5 is a schematic showing construction of the Δos-1 mutant by gene replacement by his-2+.

To determine whether Nik-1 is important for fungal development, a deletion mutant was created by replacing os-1$^+$ with the his-2$^+$ gene as illustrated in FIG. 5. FIG. 5 is a schematic representation of the genomic DNA structure of wild-type and Δos-1$^-$ strains. In this Figure, the restriction sites are indicated as follows: Bg, BglII; B, BamHI; RV, EcoRV; and N, NheI.

In this experiment, the plasmid pKB49 was used. pKB49 contains the his-2$^+$ gene on a 5-kb HindIII fragment subcloned from a cosmid provided by Dorsey Stuart (University of Hawaii). The his-2$^+$ marker was isolated as a 5-kb HindIII fragment from pKB49 and the ends were made blunt with Klenow fragment. The fragment of pHK1 from the EcoRV site upstream of the os-1 translational start site to the NheI site was removed and the NheI ends were made blunt with Klenow fragment. The blunt-ended his-2$^+$ fragment was ligated into the modified pHK1 to yield "pHK1Δnik-1::his-2$^+$". The BamHI fragment of pHK1Δos-1::his-2$^+$ containing the his-2$^+$ insertion was used to electroporate (15) conidia from the Stadler strain (pdx-1his-2Δmtr) of *N. crassa* obtained from David Stadler (University of Washington). Transformants were selected for histidine auxotrophy on minimal sorbose plates with regeneration agar (See e.g., Case et al., Proc. Natl. Acad. Sci., 76:5259–5263 [1979]) containing pyridoxine hydrochloride (pdx) (10 μg/ml). Approximately 50 transformants were picked from plates onto 1× Vogel's minimal medium slants containing pdx ("VMpdx").

Genomic DNA was isolated from each of these 50 strains (See, R. L. Metzenberg and J. N. Stevens, Neurospora Newsl., 35:28 [1982]), digested with BglII and EcoRV, and transferred onto nylon. Blots were probed with a PCR product to the upstream region of os-1$^+$ (i.e., nucleotides 325–615). Clones containing the desired bands were then subjected to three or four rounds of plating to isolate homokaryons, which were identified by Southern blot analysis (not shown) as well as PCR of genomic DNA with nik-1$^+$-specific primers NK7 (GTCCTCCAAGTACCCTG) (SEQ ID NO:15) and NK16 (GATCAGCTACGGACTTTC) (SEQ ID NO:16).

The plasmid pKB49 was electroporated into Stadler and clones were subsequently purified in the same manner to yield clone "49-9-5," which served as the wild-type control. DNA from the mutant and wild-type strains were probed with the his-2$^+$ gene to ensure that multiple copies of the gene were not integrated in the genome.

It was apparent that there were morphological phenotypes associated with the mutant during the vegetative phase. The hyphal structures of Δos-1 mutant and wild-type cultures were observed microscopically. In the mutant, many of the aerial hyphae became swollen and misshapen and appeared to lyse. Macroscopically, aerial hyphae of the mutant had the appearance of cotton candy, growing as a mass that filled the culture tube, with large areas of lysis visible. Conidia could be formed by the mutant, but they were adherent and not readily disposed in comparison to wild-type conidia. Finally, upon exposure to light, the mutant turned a deep orange or flame color when grown on small agar slants, whereas the wild type was normally peach colored. Therefore, loss of os-1$^+$ function apparently impaired normal vegetative development in *N. crassa*.

The sexual phase of the growth cycle was examined by placing the mutant on Westergaard's medium in slants. Protoperithecia became visible and these could differentiate into perithecia upon fertilization with conidia from a wild-type strain, 74A. Spores could be obtained from this cross but at reduced numbers, which may be due to inactivation of the his-2 marker by the process of repeat induced point mutation in *N. crassa* (E. U. Selker, Ann. Rev. Genet., 24:579–613 [1990]). The ability of Δos-1 mutants to be fertilized is consistent with the expression pattern of the gene during development.

EXAMPLE 6

In this Example, the osmosensitivity of os-1 mutants was investigated.

The characteristics of the Δos-1 mutant resembled those of osmosensitive *N. crassa* mutants whose morphologies are drastically affected by humidity (See e.g., D. D. Perkins et al, Microbiol. Rev., 46:426–570 [1982]). The morphology of the Δos-1 mutant appeared to be more similar to that of wild type when cultures were grown in large flasks or slants as opposed to small slants. Thus, the tolerance of the Δos-1 mutant to different osmolytes was tested. Growth of the mutant and wild type cultures were the same on Vogel's minimal medium plates. However, growth on 1 M sorbitol/0.7 M NaCl, (or 1 M KCl) resulted in restricted colonial growth. In addition, the hyphae were excessively branched and bumpy, and aerial hyphae were nonexistent, resulting in a subsequent abrogation of conidia formation. Therefore, it was apparent that the os-1$^+$ deletion manifested itself dramatically under conditions of high osmostress.

The growth response of the mutant in shaking liquid culture was also monitored. Normally, *N. crassa* can grow as a mycelium in submerged shaking liquid culture although it does not conidiate (M. L. Springer, supra). While wild type cultures grow as a mycelium with the addition of 1 M sorbitol, NaCl, or KCl to the medium, the growth of the mutant was significantly impaired; it tended to form small clumps of irregular-shaped hyphae that were hyper-branched and swollen. These results indicated that the mutant is unable to form a well-defined mycelium under conditions of high osmotic stress

EXAMPLE 7

In this Example, *C. albicans* was grown and used as the source for genomic DNA in subsequent experiments.

*Candida albicans* strain 366 (ATCC 56884) was obtained from the ATCC, and grown in PYG. An aliquot of actively growing culture was added to Manning and Mitchell's basic salts medium (0.5% w/v (NH$_4$)$_2$SO4, 0.02% w/v MgSO$_4$ o 7H$_2$O, 1.4% K$_2$HPO$_4$, 0.6% w/v KH$_2$PO$_4$, 0.5% w/v NaCl, 1.25% w/v glucose, and 1×10$^{-4}$% w/v biotin), mixed, and incubated with shaking (180 rpm), at 37° C. for approximately 30 hours to mid-log phase, as described by Manning et al. (Manning and Mitchell, J. Bacteriol., 142:714–719 [1980]).

*C. albicans* DNA was prepared using the method of Scherer and Stevens (Scherer and Stevens, Proc. Natl. Acad. Sci., 85:1452–1456 [1988]). Briefly, exponentially growing cells were washed with 1 M sorbitol. Protoplasts were prepared by resuspending the cells 10-fold concentrated in 1 M sorbitol/50 mM potassium phsophate, pH 7.4, 14 mM 2-mercaptoethanol, and 100 μg zymolyase 100T (Miles) per ml, and incubated for 30 minutes at 30° C. The protoplasts were pelleted and resuspended in 50 mM Na$_3$, 0.2% SDS (NaDodSO$_4$) with 100 μg of proteinase K per ml. This was incubated for 3 hours, at 50° C. The DNA was then extracted three times with phenol:chloroform (1:1), and precipitated with 2 volumes of ethanol. The DNA was resusupended in 10 mM Tris HCl, pH 7.5, 1 mM Na$_3$EDTA (TE buffer) with 10 μg RNase A per ml. After overnight (i.e., approximately 18–24 hours), at 4° C., the DNA was precipitated with 2 volumes of 2-propanol, and resuspended in TE buffer.

EXAMPLE 8

In this Example, the *C. albicans* cos-1 gene was amplified by PCR, and then sequenced compared with other histidine kinase genes in subsequent Examples. *C. albicans* (ATCC #36801) was grown as described below. Briefly, cells were grown overnight at 30° C. with shaking in YPD (1% yeast extract, 2% peptone, 2% glucose). The culture was harvested and resuspended in 5 ml lysis buffer (50 mM citrate/phosphate, pH 5.6, 40 mM EDTA and 1.2 M sorbitol). Zymolyase was added (15 mg) and the suspension incubated at 37° C. for 60 minutes. After centrifugation (3000 rpm for 5 minutes) the pellet was resuspended in 5× TE 15 ml. To the resuspended pellet, 1.5 ml of SDS (10%) was added and incubation continued for 5 minutes at 65° C. Then, the mixture was incubated on ice (30 min) following the addition of 5 ml potassium acetate (5 M). The mixture was then centrifuged (5000 rpm for 15 min) and the supernatant filtered through cheesecloth. The clarified supernatant was then preciptated with isopropanol, resuspended in 5× TE, and incubated with RNase. Then, the DNA was phenol extracted, EtOH precipitated, and resuspended in water, as described by Moreno et al., Meth. Enzymol., 194:795–823 [1991]).

PCR was then conducted on the DNA samples. The following primer to the H box was made with the sequence CA(T/C)GAI(A/T/C)TI(C/A)GIACICICC (SEQ ID NO:7) and served as the forward PCR primer. The reverse primers were synthesized to code for the N box: for N1A, the sequence was GT(A/G)AA(T/C)TTIAIIGC(A/G)TT (SEQ ID NO:8); while for N2A, the sequence was GC(A/G)TTIC(T/C)IACIA(G/A)TT(I)(SEQ ID NO:9). All primers were purified by electrophoresis through an acrylamide gel (20%/7 M urea) followed by purification over a Sep-Pak C18 column (Waters).

PCR mixtures contained 2.5 mM of each primer, 1.4 μg of genomic *C. albicans* DNA, 2.5 mM each dATP, dGTP, dCTP and dTTP, 10 mM Tris HCl pH 8.3, 50 mM KCl, 0.001% gelatin, and 0.5 unit of AmpliTaq (Perkin-Elmer/Cetus) in a total volume of 100 μl. Primers, buffer, and DNA templates were mixed and heated (95° C. for 10 min) in a thermocycler (Perkin-Elmer/Cetus), and then cooled to 4° C. Nucleotides and polymerase were added and reactions mixtures were cycled 25–30 times at 94° C. (1 min), 40° C. (1 min) and 72° C. (1 min), followed by a 10 minute incubation at 70° C. The samples were then electrophoresed in a 1.5% agarose gel, cloned into a T-vector (Promega) and subsequently sequenced.

Alignment of histidine kinase members was accomplished using the PILEUP program from the Wisconsin Genetics Computer Group (GCG).

EXAMPLE 9

In this Example, a genomic DNA library of *C. albicans* was constructed by digesting total genomic *C. albicans* DNA with HindIII (NEB). The DNA was size-fractionated on a 0.8% (w/v) agarose gel, fragments between 8 and 10 kb were eluted and ligated with a HindIII-digested calf intestinal alkaline phosphatase-treated pUC21 (GenBank accession #M74307; See, Vierra and Messing, Gene 100:189–194 [1991]; SEQ ID NO:23) for 20 h at 12° C. The ligation mixture was used to transform competent *E. coli* DH5α cells (BRL), and 9,000 transformants were screened with the PCR product pC1-3 (the DNA sequence of pC1-3 is shown in SEQ ID NO:21, and the amino acid sequence is shown in SEQ ID NO:22)

One positive clone designated as "pMC1" was identified and its 9.0 kb HindIII insert was sequenced using methods known in the art. Briefly, the 9.0 kb HindIII fragment was sequenced by the DNA services at the University of Colorado Health Sciences Center and the California Institute of Technology by primer walking. Primers were synthesized by GENSET, and the California Institute of Technology. The DNA sequences were analyzed using MacVector™ (Eastman Kodak, Rochester, N.Y.), the basic local alignment search tool (BLAST) and PC/Gene analysis tools. The cos-1 DNA nucleotide and deduced amino acid sequences were deposited with Genbank (Accession number: U67785)(SEQ ID NOS:17 and 18). In SEQ ID NO:17, the coding region begins at nucleotide 433 (i.e., the first residue in the ATG start codon), corresponding to the methionine at position 145 in the complete amino acid sequence. The coding region of SEQ ID NO:17 ends at nucleotide 3776 (i.e., the first residue in the stop region). SEQ ID NO:18 provides the amino acid sequence of the coding region.

EXAMPLE 10

In this Example, PCR was used to determine whether cognates of skn7 are present in humans and medically important fungi. In these experiments, primers capable of amplifying skn7-specific DNA were prepared and used in PCR with template DNAs from various sources (e.g., human, *C. albicans*, and *A. fumigatus*). The forward primer was 5-CCACCATAAATAGCAACGTC-3' (SEQ ID NO:19), and the reverse primer was 5'-GGACTCTAAATTCTGGATGC-3' (SEQ ID NO:20). The PCR mixtures contained 2.5 μM of each primer, 50 ng of genomic DNA, 10 mM dNTP, and polymerase buffer (total volume of 50 μl). Primers, buffers, and nucleotides were mixed and heated at 94° C. for 5 minutes in a thermocycler and then cooled to 40° C. for 5 minutes. Taq polymerase (0.5 units) was added to the mixtures, and the reactions were cycled 30 times at 94° C. (1 minute), 40° C (1 minute) and 72° C. (2 minutes), followed by a 7 minute extension at 72° C. The reaction products were separated by agarose gel electrophoresis and stained with ethidium bromide. A duplicate gel was also prepared, and blotted and probed with radiolabelled skn7 DNA.

PCR products were observed for *C. albicans* and *A. fumigatus* (as well as the positive control, *S. cerevisiae*). However, no PCR products were observed in reactions with human DNA as template. These results indicated that cognates of skn7 are present in *C. albicans* and *A. fumigatus*, as well as *S. cerevisiae*. Thus, it is contemplated that skn7 and its cognates will be developed as targets for development of antifungals (i.e., as a screen for inhibitors of these pathways).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A purified and isolated nucleic acid sequence encoding an osmosensing histidine kinase, wherein said sequence is selected from the group consisting of SEQ ID NO:1 and its fully complementary sequence.

2. The purified and isolated nucleic acid sequence of claim 1, wherein said nucleic acid sequence is from Neurospora.

3. A composition comprising the nucleic acid sequence of claim 1.

4. An expression vector containing the nucleic acid sequence of claim 1.

5. A host cell containing the vector of claim 4.

6. The host cell of claim 5, wherein said host cell is prokaryotic.

7. The host cell of claim 5, wherein said host cell is eukaryotic.

8. The host cell of claim 9, wherein said host cell is a fungal cell.

9. The host cell of claim 8, wherein said host cell is selected from the group consisting of Neurospora, Candida, Aspergillus, and Saccharomyces.

10. The host cell of claim 9, wherein said host cell comprises *Candida albicans*.

11. The host cell of claim 8, wherein said host cell comprises SEQ ID NO:1, such that said host cell expresses a fungal histidine kinase.

12. The host cell of claim 11, wherein said fungal histidine kinase is a *Neurospora crassa* histidine kinase.

13. The host cell of claim 11, wherein said fungal histidine kinase is a *Candida albicans* histidine kinase.

14. The host cell of claim 11, wherein said fungal histidine kinase is a Saccharomyces histidine kinase.

15. A purified and isolated nucleic acid sequence comprising SEQ ID NO:17, wherein said nucleic acid sequence encodes an osmosensing histidine kinase.

* * * * *

UNITED STATES PATENT AND TRADEMARK OFFICE
CERTIFICATE OF CORRECTION

PATENT NO. : 5,939,306
DATED : 08/17/99
INVENTOR(S) : Lisa A. Alex et al.

It is certified that error appears in the above-identified patent and that said Letters Patent is hereby corrected as shown below:

In column 1, line 6, please delete "(e.g," and insert -- (e.g., --.
In column 1, line 7, please delete "(eg," and insert -- (e.g., --.
In column 9, line 23, please delete "et al." and insert -- et al., --.
In column 9, line 28, please delete "et al." and insert -- et al., --.
In column 9, line 29, please delete "et al." and insert -- et al., --.
In column 11, line 13, please delete "et al." and insert -- et al., --.
In column 15, line 59, please delete "bounds" and insert -- bonds --.
In column 16, line 31, please delete "the" and insert -- The --.
In column 16, line 43, please delete " or specifically" and insert -- or "specifically --.
In column 16, line 65, please delete "Alternations" and insert -- Alterations --.
In column 18, line 65, please delete "("VMSN mediums)." and insert -- ("VMSN" mediums). --.
In column 22, line 55, please delete "177:6230-623" and insert -- 177:6230-6236 --.

UNITED STATES PATENT AND TRADEMARK OFFICE
CERTIFICATE OF CORRECTION

PATENT NO. : 5,939,306
DATED : 08/17/99
INVENTOR(S) : Lisa A. Alex et al.

It is certified that error appears in the above-identified patent and that said Letters Patent is hereby corrected as shown below:

In column 24, line 26, please delete "106" and insert -- $10^6$ --.

In column 24, line 61, please delete "os-1³⁰" and insert -- os-1⁺ --.

In column 25, line 16, please delete "GCCCACAATCATGAC" and insert -- GCCCACAATC<u>A</u>TGAC --.

In column 26, line 57, please delete "disposed" and insert -- dispersed, --.

In column 195, claim number 8, please delete "claim 9" and insert -- claim 5 --.

Signed and Sealed this

Twenty-ninth Day of February, 2000

Attest:

Attesting Officer

Q. TODD DICKINSON

Commissioner of Patents and Trademarks

UNITED STATES PATENT AND TRADEMARK OFFICE
CERTIFICATE OF CORRECTION

PATENT NO. : 5,939,306
DATED : August 17, 1999
INVENTOR(S) : Lisa A. Alex et al.

Page 1 of 2

It is certified that error appears in the above-identified patent and that said Letters Patent is hereby corrected as shown below:

Column 1, line 2:

Please insert --This invention was made during the course of work supported by the United States Government, under the National Institutes of Health, Grant Numbers AI 19296 and AI 33354-03. As such, the United States Government may have certain rights to this invention.--.

In column 7, line 32, please delete "Perganon" and insert --Pergamon--.

In column 18, line 34, please delete "Pittsburg" and insert --Pittsburgh--.

In column 19, line 60, please delete "produce" and insert --transform--.

In column 20, lines 5 and 6, please delete "heparin (25 µl of a 125 µg solution)" and insert --25 µl of a 5 mg/ml heparin solution--.

In column 20, line 33, please delete "not".

In column 28, line 22, please delete "preciptated" and

UNITED STATES PATENT AND TRADEMARK OFFICE
CERTIFICATE OF CORRECTION

PATENT NO. : 5,939,306
DATED : August 17, 1999
INVENTOR(S) : Lisa A. Alex et al.

It is certified that error appears in the above-identified patent and that said Letters Patent is hereby corrected as shown below:

In column 29, line 16, please delete "residue" and insert "nucleotide".

In column 29, lines 17 and 18, please delete ", corresponding to the methionine at position 145 in the complete amino acid sequence".

In column 29, line 20, please delete "residue" and insert "nucleotide".

Signed and Sealed this

Twenty-third Day of January, 2001

Attest:

Q. TODD DICKINSON

*Attesting Officer*  *Commissioner of Patents and Trademarks*

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 6545 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
AGATCTTGGT CATGAACGTG GACGGCTCGA TGTGAGAAGT GAAACCCAAG AT
ATAATGCT       60

CAAAGGGTTC CATACATACG CAGTACTGCG TAGTGTACAT CAAGTCATAC GC
GCAGAGCA      120

CAGACCACCC ATACAATATC AACCCTCAGG TCCCAAGGGG CCAAGCACGG CA
GCACCACA      180

AGCAAGAGGA AGCAACCAAG AAGCCCGAGT TCAGTTCATT GCCTGCCTTG CC
GTGCAGGA      240

AGCGCAGCCA GCGCTGATCC CTCCCTTACT CGGCGCACTC GGCCGGCAAA CA
ACCCCACC      300
```

```
AGCCCACCCC CATCCCGTTT CTGCGGCCTC TCGTCTCTCT TCCTGCGCGG CT
GTGAAGCA    360

TGGAAATCAA CTGGAGAGCC AAAGGGGAAG ACCTGAAGAC GGGAGATTAC CT
TAGCAAGC    420

ACTGGAGAGG CTTCGTTCTT CTCTGACTTC CTTTGACCCT GCCTGGTGTT TG
ACCTCGCC    480

CAGTAACAAC AACAACAACA ACAACAACAA CAACAGACCA CTCCGGGCAA CA
AGTCTCAG    540

ACCTTGGATC CGCCCTCCAC CCTCGTCGTC CGCGCGCCGC CATTATCCTT GT
TGGCCATC    600

GTCGGCCCTG TCCCTTTCTC ATCCCATCCG TTTTCCCTTT CAGAATTTCC CC
ATCCACGT    660

GCCATCCATC TTCTCGACGA AGCCCTTTTC CGCACTTGAT TTACCTGAAC GC
TCCGTCCA    720

CAGTACACTG TACAAGAGTT CCCCCGTCAA CCTCAACCTC CCTAGGTAGC AA
CTTGGAAA    780

AGAGGATGAA GAGAGAGTCG ACTGATGGGA TAGGCAAAAC AGTTGGGAGC GA
AAAAGAAA    840

AGAAACAAAA ACCAAAGCGA CGCTAGGAAG AATCGAGTGC AGTGGTCAAC GG
CACCAAAA    900

CCATACCCGA TTCATTCAGC CATTAACGC TCGGCGGGCG CCCCTGTTCC CC
GTCGCACG    960

GCACTAACAG AACTAGCACT GTGCTCCTCC TCCTCCTCCT CCTCCTCCTC TA
GCGCTCCG   1020

ACGGACTCTG CACCTGGAGT TTACAGACTG ACACTGCACG CAGTGCCCTG CT
GCGGCCCG   1080

GAGGGTCTGT CTTTGGTCTC CAGTCCCGTT CCAGTCCCGT CCATCCAGGA GC
CAGTGATC   1140

TGATCCCATC CAACCCAGTC GACCCAGTCC ACGCCCGCTG CCAGCCAGTC GA
GTCCAGGC   1200

ACCGCTCGAT AACTCCTCC TTTCTCCGCC TCACTCTCCC AACCACAGTC CA
CCCCACCGA  1260

CCGGGCCACC ACCACTCACC ACCACCACCA CGGCCCGGAC TTCTTCAACC GC
AGCAGCAG   1320

CGCAAGGAGC CAGGCCCAGC AACAGATCAG CCAGCTCTCA GCAGCAGCAG CA
GCAGCAAC   1380

AGCAGCAGCA GTGCCAGCCC AGTCCAGTCC AGTCCAGTCC GCAGTCCGCC CG
CAGTCGTC   1440

AACGACTGAC TGACTGACTG AACCTGAGGA CGAGACTAGA CTCGCTACCT AC
CTCTACCT   1500

ACCTACCTAC CTACCTACCT ACCTACCCAC CCACCGCTGT CGCTGTCCCC AG
TCAATCCT   1560

ACTACCTGAC CTACCTTAGC CACGGAGAAA AAGGCGACCA AAACAGGCAA AC
AAAATCTC   1620

CTACTGCCTC CTCGCACCGA GGCGCACGTC GAGTCTCCGA GCCTGAAGCC TC
CGTCCAGC   1680

TCCAGCTCCC GCTCTCCTTT CGCGATACAA TCCTTTTTTG AAAAACACAA TT
CCCACCCA   1740

TCGCGGCGGG ATATCTAGTA CAAACAGTGA GCCCACTCCC CACCAGCACT GT
TCTTTCGT   1800

CTGAAACTGT CAATTATACG CACGCGCTTG CTTTCTTCAC ACCTTTGCTG AC
GATCCCCT   1860

GCTTCAAGAC CACCACAAAC CCGACGCTCT GCATTGCAAT TTCGCAACAT AA
CCACATCA   1920
```

-continued

```
AGCTACCCAA CCAGCAACAC AGCCCAGAGA CCAGAGATCG ATTACAACGC CG
CTCCCTAT   1980

TCTCTCGAGT CCATCTCCCA TCTCGATTCA ATTGAAACCA ACTTCTTAGA CC
CGCAAACG   2040

CCCATGAAGT CGCAAGAGTC GATTGTTACC CACTAGCTTC CGCGCCTTGC CC
GACTGCGT   2100

TTCCTGCTCT ATTCCGTCCC CAAGGCTCAC GGCGCCAACG GCCGTAGCCC AC
AATCATGA   2160

CTGACGGACC AACTCTCGCA GCTATTGCTG CTCTCGTCAA ATCCCTGGCT GT
CGACCCGG   2220

CCACTACCCA GACCTCTGGA CTTCGCCCAA GCACCCATGT CAGGCTTCCC GG
TCCGTATA   2280

CCCGTGAGAA GGGTGATCTG GAGCGTGAGC TCTCGGCTCT TGTTGTCCGC AT
AGAGCAGC   2340

TGGAGACTGC CGCCATCGCT GCCTCTCCTC CAGCCATGCC CGATACACCA AA
TGCGCCAA   2400

CCGATGCGCT GTTTTCAAAC GGCACCCTTT CGCCATCCTC GGAAACGCCT GA
TGCCCGCT   2460

ACCCCGCTCC GCTACCGCGG AATGGCTTCA TCGACGAGGC CCTTGAGGGT CT
CCGCGAGC   2520

ATGTCGACGA CCAGTCCAAG CTGCTTGACA GCCAGCGTCA GGAGCTTGCT GG
GGTCAACG   2580

CCCAGCTGAT TGAGCAAAAG CAACTTCAGG AAAAGGCTCT GGCTATTATC GA
ACAGGAAC   2640

GGGTTGCTAC CCTTGAGCGG GAACTCTGGA AGCATCAAAA GGCCAACGAG GC
CTTCCAAA   2700

AGGCTCTCCG AGAAATCGGT GAGATTGTCA CTGCCGTCGC CAGGGGTGAT TT
GTCCAAAA   2760

AGGTCCGGAT GAACTCGGTG GAAATGGACC CGGAAATCAC CACCTTCAAG CG
TACGATAA   2820

ACACAATGAT GGACCAGTTG CAAGTCTTCT CCAGCGAAGT CTCGCGTGTC GC
TCGTGAAG   2880

TCGGAACCGA GGGTATTCTC GGTGGCCAAG CTCAGATCGA AGGCGTTGAC GG
CACCTGGA   2940

AGGAACTCAC AGACAACGGT ATGTTTGATC CCATCTTGAC AGCCGCAGCC GT
AGTGGCCT   3000

ATGTGTACTG ATCATATCAT CTAGTCAACG TCATGGCCCA GAATCTTACC GA
CCAAGTGC   3060

GAGAGATTGC TTCCGTAACG ACTGCTGTCG CTCATGGCGA TCTTACCAAG AA
AATCGAGC   3120

GTCCCGCCAA GGGAGAAATA CTTCAACTTC AACAAACCAT CAACACAATG GT
GGATCAGC   3180

TACGGACTTT CGCCTCTGAA GTTACACGTG TCGCCAGAGA TGTCGGTACC GA
GGGTATCC   3240

TCGGTGGTCA AGCCGACGTT GAAGGAGTCC AGGGCATGTG GAACGAACTT AC
GGTTAATG   3300

TGAACGCCAT GGCCAACAAT CTAACAACCC AAGTCAGAGA TATCATCAAG GT
TACTACCG   3360

CTGTCGCCAA GGGTGACCTT ACTCAAAAAG TACAAGCTGA ATGCCGCGGT GA
GATTTTCG   3420

AACTGAAGAA GACTATCAAC TCTATGGTGG ACCAACTACA ACAATTTGCT CG
GGAAGTCA   3480

CAAAGATCGC CAGGGAAGTC GGAACCGAAG GAAGGCTCGG TGGGCAGGCC AC
```

```
TGTTCACG    3540

ATGTTCAGGG TACTTGGAGG GACCTCACCG AAAACGTCAA CGGCATGGCC AT
GAACTTGA    3600

CCACACAGGT GCGAGAAATC GCAAAGGTTA CTACAGCCGT CGCCAAGGGT GA
TTTGACCA    3660

AGAAGATTGG GGTCGAGGTT CAGGGTGAGA TCCTGGATTT GAAGAACACC AT
CAACACCA    3720

TGGTTGACCG TCTTGGTACT TTCGCTTTCG AGGTCAGCAA GGTCGCCAGG GA
AGTCGGCA    3780

CCGATGGTAC CTTGGGTGGT CAGGCACAGG TTGATAATGT GGAGGGCAAG TG
GAAGGATC    3840

TCACAGAGAA CGTCAACACC ATGGCCAGCA ACCTTACATC TCAGGTAAGC TG
CTCCTAGA    3900

TGATCCTTTG CGGCATGCAC TGTTTGCTAA CTTTTCACAG GTCCGTGGGA TC
TCTACCGT    3960

CACACAAGCC ATTGCCAATG GTGATATGAG CCGCAAGATT GAAGTTGAAG CC
AAGGGAGA    4020

GATACTCATA CTCAAGGAGA CTATCAACAA CATGGTTGAC CGACTCTCCA TT
TTCTGTAA    4080

TGAGGTGCAG AGAGTCGCCA AGGATGTCGG TGTCGATGGT ATCATGGGAG GA
CAAGCCGA    4140

TGTTGCTGGC CTGAAGGGCA GGTGGAAGGA AATTACCACC GATGTCAACA CA
ATGGCGAA    4200

TAACTTGGTA TGTCTCGCCG CCGCCAGCAC CCTTGAACAG CACCCCTTTT TG
CTAATGCC    4260

TTTTACAGAC GGCTCAAGTG AGAGCGTTCG GCGACATCAC AAATGCAGCA AC
AGACGGGG    4320

ACTTTACAAA ACTCGTCGAG GTAGAAGCCT CGGGCGAGAT GGACGAACTC AA
AAAGAAGA    4380

TCAATCAGAT GGTCTACAAT TTGAGGGACA GTATTCAACG TAATACCCAG GC
CAGGGAAG    4440

CCGCCGAACT GGCCAATAAG ACCAAGTCCG AGTTTTTGGC GAACATGTCC CA
CGAAATAC    4500

GCACACCCAT GAACGGCATT ATCGGCATGA CACAACTTAC TCTCGATACT GA
CCTGACAC    4560

AGTATCAGAG AGAAATGCTC AACATTGTCA ACTCCCTGGC CAACAGCTTA CT
GACCATCA    4620

TCGACGACAT TTTGGATCTG TCCAAGATCG AAGCTAGGCG TATGGTCATC GA
AGAGATTC    4680

CTTATACGTT GCGTGGCACC GTCTTCAACG CGCTCAAGAC TCTTGCCGTC AA
GGCAAACG    4740

AGAAGTTTCT GGATCTTACC TATCGTGTCG ACCATTCTGT ACCCGACCAC GT
CGTCGGAG    4800

ACTCCTTCAG GTTGCGCCAG ATTATTCTTA ACCTTGTTGG CAACGCTATC AA
GTTCACCG    4860

AGCATGGTGA AGTCAGTCTT ACCATCCAGA AGGCCTCTTC AGTACAGTGC AG
CACCGAAG    4920

AGTACGCTAT CGAGTTTGTC GTTTCCGACA CTGGTATCGG TATTCCGGCG GA
CAAGCTGG    4980

ATCTCATCTT CGACACTTTC CAGCAGGCCG ATGGTTCAAT GACTCGCAAG TT
TGGCGGTA    5040

CTGGTCTCGG TCTCTCCATT TCCAAGCGTC TTGTCAACCT CATGGGTGGT GA
CGTGTGGG    5100
```

```
TGAAGAGTGA GTATGGTAAG GGTAGCAAGT TCTTCTTCAC CTGCGTGGTC CG
CTTGGCCA    5160

ACGACGATAT TTCGTTGATC GCCAAGCAGC TCAACCCTTA CAAGAGTCAC CA
GGTCCTGT    5220

TCATCGACAA GGGCCGCACC GGACATGGAC CGGAGATCGC CAAGATGCTC CA
CGGCTTGG    5280

GCCTCGTTCC CATCGTCGTC GACTCGGAGA GGAATCCTGC GCTCGAGAAG GC
CAGAGCTG    5340

CCGGCCAGGC GCCCTACGAC GTCATCATTG TGGACTCGAT CGAGGATGCA AG
GCGCTTGC    5400

GGTCTGTTGA CGACTTTAAG TACCTTCCCA TCGTATTGCT AGCACCAGTC GT
TCACGTCT    5460

CGCTAAAGTC TTGCCTTGAC TTGGGTATCA CGTCGTACAT GACGACGCCT TG
TCAACTCA    5520

TTGACCTCGG TAACGGCATG GTCCCTGCTC TCGAAAATAG GGCTACGCCG TC
GCTGGCGG    5580

ACAACACCAA ATCTTTTGAG ATCCTGCTTG CCGAAGACAA CACGGTCAAC CA
GAGGCTCG    5640

CGGTCAAGAT CCTGGAGAAG TATCACCACG TCGTCACCGT TGTTGGAAAC GG
TGAAGAGG    5700

CTGTTGAGGC CGTCAAGAGG AAAAAGTTCG ATGTCATTCT TATGGACGTC CA
GATGCCTA    5760

TTATGGTGAG TCAAAGCTGT TTTTCAAACC AAGAAGCCGA TGCTAACAAT TT
TCATAGGG    5820

CGGTTTCGAA GCTACGGCCA AGATTCGCGA GTACGAGCGC AGCCTCGGCA GC
CAGCGCAC    5880

ACCCATCATC GCCCTCACGG CGCATGCCAT GATGGGTGAC AGGGAAAAGT GT
ATCCAGGC    5940

ACAGATGGAC GAGTATCTCT CCAAGCCGCT GCAGCAGAAC CATCTAATCC AG
ACCATACT    6000

CAAGTGTGCG ACGCTCGGCG GGCAACTACT CGAGAAGAAC CGGGAGCGCG AG
CTGACCCG    6060

TGCTGCCGAT GCCGTCACAG GCGGCCGCCG CGACAACGGC ATGTACTCTG CC
AGCCAAGC    6120

CGCGCAGCAC GCTGCGCTCC GCCCACCCCT CGCCACCAGG GGCCTCACTG CC
GCCGACAG    6180

CCTCGTCTCC GGCTTGGAGA GCCCATCCAT CGTGACGGCG GATAAGGAGG AT
CCTCTGAG    6240

CAGGGCACGT GCAAGCCTCT CCGAACCCAA CATCCATAAA GCAAGCTAAC CG
TGTGGATG    6300

GGTCAATTCT GACTTTTATT GGAGGAATTT AGCTGGTCAT ACGAGCACAT AC
TACTCTTT    6360

GATCAACATC GCGTGCGATA CACCAAGCAA CCAACGGCCA CGCCAACTTA AA
GTGGAAGA    6420

AGTTTTTATG AGATGGGATG GAAGGAAAAA GAAACGAAGA GAGAAAGGGA AG
AAGAAAGG    6480

ATGGAAAGTG GATGGAGTCC GTGTTGTCTT TATCGTGTTG TGTGTTTCTC TG
TCCGGTAC    6540

CCGGG

6545

(2) INFORMATION FOR SEQ ID NO:2:
```

(i) SEQUENCE CHARACTERISTICS:
    (A) LENGTH: 1298 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:2:

Met Thr Asp Gly Pro Thr Leu Ala Ala Ile Ala Ala Leu Val Lys Ser
1               5                   10                  15

Leu Ala Val Asp Pro Ala Thr Thr Gln Thr Ser Gly Leu Arg Pro Ser
            20                  25                  30

Thr His Val Arg Leu Pro Gly Pro Tyr Thr Arg Glu Lys Gly Asp Leu
        35                  40                  45

Glu Arg Glu Leu Ser Ala Leu Val Val Arg Ile Glu Gln Leu Glu Thr
    50                  55                  60

Ala Ala Ile Ala Ala Ser Pro Pro Ala Met Pro Asp Thr Pro Asn Ala
65                  70                  75                  80

Pro Thr Asp Ala Leu Phe Ser Asn Gly Thr Leu Ser Pro Ser Ser Glu
                85                  90                  95

Thr Pro Asp Ala Arg Tyr Pro Ala Pro Leu Pro Arg Asn Gly Phe Ile
            100                 105                 110

Asp Glu Ala Leu Glu Gly Leu Arg Glu His Val Asp Asp Gln Ser Lys
        115                 120                 125

Leu Leu Asp Ser Gln Arg Gln Glu Leu Ala Gly Val Asn Ala Gln Leu
    130                 135                 140

Ile Glu Gln Lys Gln Leu Gln Glu Lys Ala Leu Ala Ile Ile Glu Gln
145                 150                 155                 160

Glu Arg Val Ala Thr Leu Glu Arg Glu Leu Trp Lys His Gln Lys Ala
                165                 170                 175

```
Asn Glu Ala Phe Gln Lys Ala Leu Arg Glu Il
e Gly Glu Ile Val Thr
         180
         185
         190

Ala Val Ala Arg Gly Asp Leu Ser Lys Lys Va
l Arg Met Asn Ser Val
       195
       200
       205

Glu Met Asp Pro Glu Ile Thr Thr Phe Lys Ar
g Thr Ile Asn Thr Met
     210
     215
     220

Met Asp Gln Leu Gln Val Phe Ser Ser Glu Va
l Ser Arg Val Ala Arg
225                    2
 30                    2
 35                    2
 40

Glu Val Gly Thr Glu Gly Ile Leu Gly Gly Gl
n Ala Gln Ile Glu Gly
           245
           250
           255

Val Asp Gly Thr Trp Lys Glu Leu Thr Asp As
n Val Asn Val Met Ala
         260
         265
         270

Gln Asn Leu Thr Asp Gln Val Arg Glu Ile Al
a Ser Val Thr Thr Ala
       275
       280
       285

Val Ala His Gly Asp Leu Thr Lys Lys Ile Gl
u Arg Pro Ala Lys Gly
     290
     295
     300

Glu Ile Leu Gln Leu Gln Gln Thr Ile Asn Th
r Met Val Asp Gln Leu
305                    3
 10                    3
 15                    3
 20

Arg Thr Phe Ala Ser Glu Val Thr Arg Val Al
a Arg Asp Val Gly Thr
             325
             330
             335

Glu Gly Ile Leu Gly Gly Gln Ala Asp Val Gl
u Gly Val Gln Gly Met
           340
           345
           350

Trp Asn Glu Leu Thr Val Asn Val Asn Ala Me
t Ala Asn Asn Leu Thr
         355
         360
         365

Thr Gln Val Arg Asp Ile Ile Lys Val Thr Th
r Ala Val Ala Lys Gly
       370
       375
       380
```

```
Asp Leu Thr Gln Lys Val Gln Ala Glu Cys Ar
g Gly Glu Ile Phe Glu
385                 3
90                  3
95                  4
00

Leu Lys Lys Thr Ile Asn Ser Met Val Asp Gl
n Leu Gln Gln Phe Ala
        405
            410
                415

Arg Glu Val Thr Lys Ile Ala Arg Glu Val Gl
y Thr Glu Gly Arg Leu
        420
            425
                430

Gly Gly Gln Ala Thr Val His Asp Val Gln Gl
y Thr Trp Arg Asp Leu
        435
            440
                445

Thr Glu Asn Val Asn Gly Met Ala Met Asn Le
u Thr Thr Gln Val Arg
        450
            455
                460

Glu Ile Ala Lys Val Thr Thr Ala Val Ala Ly
s Gly Asp Leu Thr Lys
465                 4
70                  4
75                  4
80

Lys Ile Gly Val Glu Val Gln Gly Glu Ile Le
u Asp Leu Lys Asn Thr
        485
            490
                495

Ile Asn Thr Met Val Asp Arg Leu Gly Thr Ph
e Ala Phe Glu Val Ser
        500
            505
                510

Lys Val Ala Arg Glu Val Gly Thr Asp Gly Th
r Leu Gly Gly Gln Ala
        515
            520
                525

Gln Val Asp Asn Val Glu Gly Lys Trp Lys As
p Leu Thr Glu Asn Val
        530
            535
                540

Asn Thr Met Ala Ser Asn Leu Thr Ser Gln Va
l Arg Gly Ile Ser Thr
545                 5
50                  5
55                  5
60

Val Thr Gln Ala Ile Ala Asn Gly Asp Met Se
r Arg Lys Ile Glu Val
            565
                570
                    575

Glu Ala Lys Gly Glu Ile Leu Ile Leu Lys Gl
u Thr Ile Asn Asn Met
            580
                585
                    590
```

-continued

Val Asp Arg Leu Ser Ile Phe Cys Asn Glu Val Gln Arg Val Ala Lys
             595                 600                 605

Asp Val Gly Val Asp Gly Ile Met Gly Gly Gln Ala Asp Val Ala Gly
        610                 615                 620

Leu Lys Gly Arg Trp Lys Glu Ile Thr Thr Asp Val Asn Thr Met Ala
625                 630                 635                 640

Asn Asn Leu Thr Ala Gln Val Arg Ala Phe Gly Asp Ile Thr Asn Ala
                645                 650                 655

Ala Thr Asp Gly Asp Phe Thr Lys Leu Val Glu Val Glu Ala Ser Gly
            660                 665                 670

Glu Met Asp Glu Leu Lys Lys Lys Ile Asn Gln Met Val Tyr Asn Leu
        675                 680                 685

Arg Asp Ser Ile Gln Arg Asn Thr Gln Ala Arg Glu Ala Ala Glu Leu
    690                 695                 700

Ala Asn Lys Thr Lys Ser Glu Phe Leu Ala Asn Met Ser His Glu Ile
705                 710                 715                 720

Arg Thr Pro Met Asn Gly Ile Ile Gly Met Thr Gln Leu Thr Leu Asp
                725                 730                 735

Thr Asp Leu Thr Gln Tyr Gln Arg Glu Met Leu Asn Ile Val Asn Ser
            740                 745                 750

Leu Ala Asn Ser Leu Leu Thr Ile Ile Asp Asp Ile Leu Asp Leu Ser
        755                 760                 765

Lys Ile Glu Ala Arg Arg Met Val Ile Glu Glu Ile Pro Tyr Thr Leu
    770                 775                 780

Arg Gly Thr Val Phe Asn Ala Leu Lys Thr Leu Ala Val Lys Ala Asn
785                 790                 795                 800

-continued

00

Glu Lys Phe Leu Asp Leu Thr Tyr Arg Val Asp His Ser Val Pro Asp
805 810 815

His Val Val Gly Asp Ser Phe Arg Leu Arg Gln Ile Ile Leu Asn Leu
820 825 830

Val Gly Asn Ala Ile Lys Phe Thr Glu His Gly Glu Val Ser Leu Thr
835 840 845

Ile Gln Lys Ala Ser Ser Val Gln Cys Ser Thr Glu Glu Tyr Ala Ile
850 855 860

Glu Phe Val Val Ser Asp Thr Gly Ile Gly Ile Pro Ala Asp Lys Leu
865 870 875 880

Asp Leu Ile Phe Asp Thr Phe Gln Gln Ala Asp Gly Ser Met Thr Arg
885 890 895

Lys Phe Gly Gly Thr Gly Leu Gly Leu Ser Ile Ser Lys Arg Leu Val
900 905 910

Asn Leu Met Gly Gly Asp Val Trp Val Lys Ser Glu Tyr Gly Lys Gly
915 920 925

Ser Lys Phe Phe Phe Thr Cys Val Val Arg Leu Ala Asn Asp Asp Ile
930 935 940

Ser Leu Ile Ala Lys Gln Leu Asn Pro Tyr Lys Ser His Gln Val Leu
945 950 955 960

Phe Ile Asp Lys Gly Arg Thr Gly His Gly Pro Glu Ile Ala Lys Met
965 970 975

Leu His Gly Leu Gly Leu Val Pro Ile Val Val Asp Ser Glu Arg Asn
980 985 990

Pro Ala Leu Glu Lys Ala Arg Ala Ala Gly Gln Ala Pro Tyr Asp Val
995 1000

-continued

```
        1005
Ile Ile Val Asp Ser Ile Glu Asp Ala Arg Ar
g Leu Arg Ser Val Asp
    1010
     1015
      1020
Asp Phe Lys Tyr Leu Pro Ile Val Leu Leu Al
a Pro Val Val His Val
1025            1030
         1035
          1040
Ser Leu Lys Ser Cys Leu Asp Leu Gly Ile Th
r Ser Tyr Met Thr Thr
         1045
          1050
           1055
Pro Cys Gln Leu Ile Asp Leu Gly Asn Gly Me
t Val Pro Ala Leu Glu
         1060
          1065
           1070
Asn Arg Ala Thr Pro Ser Leu Ala Asp Asn Th
r Lys Ser Phe Glu Ile
         1075
          1080
           1085
Leu Leu Ala Glu Asp Asn Thr Val Asn Gln Ar
g Leu Ala Val Lys Ile
     1090
      1095
       1100
Leu Glu Lys Tyr His His Val Val Thr Val Va
l Gly Asn Gly Glu Glu
1105            1110
          1115
           1120
Ala Val Glu Ala Val Lys Arg Lys Lys Phe As
p Val Ile Leu Met Asp
          1125
           1130
            1135
Val Gln Met Pro Ile Met Gly Gly Phe Glu Al
a Thr Ala Lys Ile Arg
           1140
            1145
             1150
Glu Tyr Glu Arg Ser Leu Gly Ser Gln Arg Th
r Pro Ile Ile Ala Leu
         1155
          1160
           1165
Thr Ala His Ala Met Met Gly Asp Arg Glu Ly
s Cys Ile Gln Ala Gln
    1170
     1175
      1180
Met Asp Glu Tyr Leu Ser Lys Pro Leu Gln Gl
n Asn His Leu Ile Gln
1185            1190
         1195
          1200
Thr Ile Leu Lys Cys Ala Thr Leu Gly Gly Gl
n Leu Leu Glu Lys Asn
           1205
            1210
             1215
```

```
Arg Glu Arg Glu Leu Thr Arg Ala Ala Asp Al
a Val Thr Gly Gly Arg
            1220
               1225
                  1230

Arg Asp Asn Gly Met Tyr Ser Ala Ser Gln Al
a Ala Gln His Ala Ala
         1235
            1240
               1245

Leu Arg Pro Pro Leu Ala Thr Arg Gly Leu Th
r Ala Ala Asp Ser Leu
      1250
         1255
            1260

Val Ser Gly Leu Glu Ser Pro Ser Ile Val Th
r Ala Asp Lys Glu Asp
1265            1270
            1275
               1280

Pro Leu Ser Arg Ala Arg Ala Ser Leu Ser Gl
u Pro Asn Ile His Lys
            1285
               1290
                  1295

Ala Ser (2) INFORMATION FOR SEQ ID NO:3:

(i) SEQUENCE CHARACTERISTICS:
        (A) LENGTH: 5175 base
pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

GTCCAGGCAC CGCTCGATAA CTCTCCTCTT TCTCCGCCTC ACTCTCCCAA CC
ACAGTCCA    60

CCCACCGACC GGGCCACCAC CACTCACCAC CACCACCACG GCCCGGACTT CT
TCAACCGC    120

AGCAGCAGCG CAAGGAGCCA GGCCCAGCAA CAGATCAGCC AGCTCTCAGC AG
CAGCAGCA    180

GCAGCAACAG CAGCAGCAGT GCCAGCCCAG TCCAGTCCAG TCCAGTCCGC AG
TCCGCCCG    240

CAGTCGTCAA CGACTGACTG ACTGACTGAA CCTGAGGACG AGACTAGACT CG
CTACCTAC    300

CTCTACCTAC CTACCTACCT ACCTACCTAC CTACCCACCC ACCGGTGGCG GT
GTCCCCAG    360

TACAAATCCT ACTACCTGAC CTACCTTAGC CACGGAGAAA AAGGGGAACA AA
AACGGGCA    420

AAACAAAATC TCCTACTGCC TCCTGCGCAC CGAGGCGCAC GTCGAGTCTC CG
AGCCTGAA    480

GCCTCCGTCC AGCTCCACGT CCCGCTCTCC TTTCGCGATA CAATCCTTTT TT
GAAAAACA    540

CAATTCCCAC CCATCGCGGC GGGATATCTA GTACAAACAA CCACCACAAA CC
CGACGCTC    600

TGCATGTGCA ATTTCGCAAC ATAACCACAT CAAGCTACCC AACCAGCAAC AC
AGCCCAGA    660

GACCAGAGAT CGATTACAAC GCCGCTCCCT ATTCTCTCGA GTCCATCTCC CA
```

-continued

```
TCTCGATT          720

CAATTGAAAC CAACTTCTTA GACCCGCAAA CGCCCATGAA GTCGCAAGAG TC
GATTGTTA          780

CCCACTAGCT TCCGCGCCTT GCCCGACTGC GTTTCCTGCT CTATTCCGTC CC
CAAGGCTC          840

ACGGCGCCAA CGGCCGTAGC CCACAATCAT GACTGACGGA CCAACTCTCG CA
GCTATTGC          900

TGCTCTCGTC AAATCCCTGG CTGTCGACCC GGCCACTACC CAGACCTCTG GA
CTTCGCCC          960

AAGCACCCAT GTCAGGCTTC CCGGTCCGTA TACCCGTGAG AAGGGTGATC TG
GAGCGTGA         1020

GCTCTCGGCT CTTGTTGTCC GCATAGAGCA GCTGGAGACT GCCGCCATCG CT
GCCTCTCC         1080

TCCAGCCATG CCCGATACAC CAAATGCGCC AACCGATGCG CTGTTTTCAA AC
GGCACCCT         1140

TTCGCCATCC TCGGAAACGC CTGATGCCCG CTACCCCGCT CCGCTACCGC GA
AATGGCTT         1200

CATCGACGAG GCCCTTGAGG GTCTCCGCGA GCATGTCGAC GACCAGTCCA AG
CTGCTTGA         1260

CAGCCAGCGT CAGGAGCTTG CTGGGGTCAA CGCCCAGCTG ATTGAGCAAA AG
CAACTTCA         1320

GGAAAAGGCT CTGGCTATTA TCGAACAGGA ACGGGTTGCT ACCCTTGAGC GG
GAACTCTG         1380

GAAGCATCAA AAGGCCAACG AGGCCTTCCA AAAGGCTCTC CGAGAAATCG GT
GAGATTGT         1440

CACTGCCGTC GCCAGGGGTG ATTTGTCCAA AAAGGTCCGG ATGAACTCGG TG
GAAATGGA         1500

CCCGGAAATC ACCACCTTCA AGCGTACGAT AAACACAATG ATGGACCAGT TG
CAAGTCTT         1560

CTCCAGCGAA GTCTCGCGTG TCGCTCGTGA AGTCGGAACC GAGGGTATTC TC
GGTGGCCA         1620

AGCTCAGATC GAAGGCGTTG ACGGCACCTG GAAGGAACTC ACAGACAACG TC
AACGTCAT         1680

GGCCCAGAAT CTTACCGACC AAGTGCGAGA GATTGCTTCC GTAACGACTG CT
GTCGCTCA         1740

TGGCGATCTT ACCAAGAAAA TCGAGCGTCC CGCCAAGGGA GAAATACTTC AA
CTTCAACA         1800

AACCATCAAC ACAATGGTGG ATCAGCTACG GACTTTCGCC TCTGAAGTTA CA
CGTGTCGC         1860

CAGAGATGTC GGTACCGAGG GTATCCTCGG TGGTCAAGCC GACGTTGAAG GA
GTCCAGGG         1920

CATGTGGAAC GAACTTACGG TTAATGTGAA CGCCATGGCC AACAATCTAA CA
ACCCAAGT         1980

CAGAGATATC ATCAAGGTTA CTACCGCTGT CGCCAAGGGT GACCTTACTC AA
AAAGTACA         2040

AGCTGAATGC CGCGGTGAGA TTTTCGAACT GAAGAAGACT ATCAACTCTA TG
GTGGACCA         2100

ACTACAACAA TTTGCTCGGG AAGTCACAAA GATCGCCAGG GAAGTCGGAA CC
GAAGGAAG         2160

GCTCGGTGGG CAGGCCACTG TTCACGATGT TCAGGGTACT TGGAGGGACC TC
ACCGAAAA         2220

CGTCAACGGC ATGGCCATGA ACTTGACCAC ACAGGTGCGA GAAATCGCAA AG
GTTACTAC         2280
```

```
AGCCGTCGCC AAGGGTGATT TGACCAAGAA GATTGGGGTC GAGGTTCAGG GT
GAGATCCT   2340

GGATTTGAAG AACACCATCA ACACCATGGT TGACCGTCTT GGTACTTTCG CT
TTCGAGGT   2400

CAGCAAGGTC GCCAGGGAAG TCGGCACCGA TGGTACCTTG GGTGGTCAGG CA
CAGGTTGA   2460

TAATGTGGAG GGCAAGTGGA AGGATCTCAC AGAGAACGTC AACACCATGG CC
AGCAACCT   2520

TACATCTCAG GTCCGTGGGA TCTCTACCGT CACACAAGCC ATTGCCAATG GT
GATATGAG   2580

CCGCAAGATT GAAGTTGAAG CCAAGGGAGA GATACTCATA CTCAAGGAGA CT
ATCAACAA   2640

CATGGTTGAC CGACTCTCCA TTTTCTGTAA TGAGGTGCAG AGAGTCGCCA AG
GATGTCGG   2700

TGTCGATGGT ATCATGGGAG GACAAGCCGA TGTTGCTGGC CTGAAGGGCA GG
TGGAAGGA   2760

AATTACCACC GATGTCAACA CAATGGCGAA TAACTTGACG GCTCAAGTGA GA
GCGTTCGG   2820

CGACATCACA AATGCAGCAA CAGACGGGGA CTTTACAAAA CTCGTCGAGG TA
GAAGCCTC   2880

GGGCGAGATG GACGAACTCA AAAGAAGAT CAATCAGATG GTCTACAATT TG
AGGGACAG   2940

TATTCAACGT AATACCCAGG CCAGGGAAGC CGCCGAACTG GCCAATAAGA CC
AAGTCCGA   3000

GTTTTTGGCG AACATGTCCC ACGAAATACG CACACCCATG AACGGCATTA TC
GGCATGAC   3060

ACAACTTACT CTCGATACTG ACCTGACACA GTATCAGAGA GAAATGCTCA AC
ATTGTCAA   3120

CTCCCTGGCC AACAGCTTAC TGACCATCAT CGACGACATT TTGGATCTGT CC
AAGATCGA   3180

AGCTAGGCGT ATGGTCATCG AAGAGATTCC TTATACGTTG CGTGGCACCG TC
TTCAACGC   3240

GCTCAAGACT CTTGCCGTCA AGGAAACCGA GAAGTTTCTG GATCTTACCT AT
CGTGTCGA   3300

CCATTCTGTA CCCGACCACG TCGTCGGAGA CTCCTTCAGG TTGCGCCAGA TT
ATTCTTAA   3360

CCTTGTTGGC AACGCTATCA AGTTCACCGA GCATGGTGAA GTCAGTCTTA CC
ATCCAGAA   3420

GGCCTCTTCA GTACAGTGCA GCACCGAAGA GTACGCTATC GAGTTTGTCG TT
TCCGACAC   3480

TGGTATCGGT ATTCCGGCGG ACAAGCTGGA TCTCATCTTC GACACTTTCC AG
CAGGCCGA   3540

TGGTTCAATG ACTCGCAAGT TTGGCGGTAC TGGTCTCGGT CTCTCCATTT CC
AAGCGTCT   3600

TGTCAACCTC ATGGGTGGTG ACGTTTGGGT GAAGAGTGAG TATGGTAAGG GT
AGCAAGTT   3660

CTTCTTCACC TGCGTGGTCC GCTTGGCCAA CGACGATATT TCGTTGATCG CC
AAGCAGCT   3720

CAACCCTTAC AAGAGTCACC AGGTCCTGTT CATCGACAAG GGCCGCACCG GA
CATGGACC   3780

GGAGATCGCC AAGATGCTCC ACGGCTTGGG CCTCGTTCCC ATCGTCGTCG AC
TCGGAGAG   3840

GAATCCTGCG CTCGAGAAGG CCAGAGCTGC CGGCCAGGCG CCCTACGACG TC
ATCATTGT   3900
```

```
GGACTCGATC GAGGATGCAA GGCGCTTGCG GTCGTTGAC GACTTTAAGT AC
CTTCCCAT    3960

CGTATTGCTA GCACCAGTCG TTCACGTCTC GCTAAAGTCT TGCCTTGACT TG
GGTATCAC    4020

GTCGTACATG ACGACGCCTT GTCAACTCAT TGACCTCGGT AACGGCATGG TC
CCTGCTCT    4080

CGAAAATAGG GCTACGCCGT CGCTGGCGGA CAACACCAAA TCTTTTGAGA TC
CTGCTTGC    4140

CGAAGACAAC ACGGTCAACC AGAGGCTCGC GGTCAAGATC CTGGAGAAGT AT
CACCACGT    4200

CGTCACCGTT GTTGGAAACG GTGAAGAGGC TGTTGAGGCC GTCAAGAGGA AA
AAGTTCGA    4260

TGTCATTCTT ATGGACGTCC AGATGCCTAT TATGGGCGGT TTCGAAGCTA CG
GCCAAGAT    4320

TCGCGAGTAC GAGCGCAGCC TCGGCAGCCA GCGCACACCC ATCATCGCCC TC
ACGGCGCA    4380

TGCCATGATG GGTGACAGGG AAAAGTGTAT CCAGGCACAG ATGGACGAGT AT
CTCTCCAA    4440

GCCGCTGCAG CAGAACCATC TAATCCAGAC CATACTCAAG TGTGCGACGC TC
GGCGGGCA    4500

ACTACTCGAG AAGAACCGGG AGCGCGAGCT GACCCGTGCT GCCGATGCCG TT
ACAGGCGG    4560

CCGCCGCGAC AACGGCATGT ACTCTGCCAG CCAAGCCGCG CAGCACGCTG CG
CTCCGCCC    4620

ACCCCTCGCC ACCAGGGGCC TCACTGCCGC CGACAGCCTC GTCTCCGGCT TG
GAGAGCCC    4680

ATCCATCGTG ACGGCGGATA AGGAGGATCC TCTGAGCAGG GCACGTGCAA GC
CTCTCCGA    4740

ACCCAACATC CATAAAGCAA GCTAACCGTG TGGATGGGTC AATTCTGACT TT
TATTGGAG    4800

GAATTTAGCT GGTCATACGA GCACATACTA CTCTTTGATC AACATCGCGT GC
GATACACC    4860

AAGCAACCAA CGGCCACGCC AACTTAAAGT GGAAGAAGGT TTTTATGAGA TG
GGATGGAA    4920

GGAAAAAGAA ACGAGGAGAG AAAGGGAGGA AGAAAGGATG GAAAGTGGAT GG
AGTCCGTG    4980

TTGTCTTTAT CGTGTTGTGT GTTTTCTCTG TCCGGTACCC GGGTTCAAAA TC
AGGTTTTT    5040

AAGGTCCAAA GGCGGTTTCT GTTATCAACA AGGCATTGAA ATTATTACTT GC
GGCTGGTT    5100

TGCTAGTTTT CAATTTTGGA TGTCTTGTTC CTCTGTCTCG TGTCTCTCTC GT
ATTTACTG    5160

GTTCGGACTG TTGGA

5175

(2) INFORMATION FOR SEQ ID NO:4:

(i) SEQUENCE CHARACTERISTICS:
        (A) LENGTH: 1298 amino
acids
        (B) TYPE: amino acid
        (C) STRANDEDNESS: Not R
elevant
        (D) TOPOLOGY: linear
```

(ii) MOLECULE TYPE: peptide (xi) SEQUENCE DESCRIPTION: SEQ ID NO:4:

```
Met Thr Asp Gly Pro Thr Leu Ala Ala Ile Al
a Ala Leu Val Lys Ser
1               5
                        10
                                15

Leu Ala Val Asp Pro Ala Thr Thr Gln Thr Se
r Gly Leu Arg Pro Ser
            20
                    25
                            30

Thr His Val Arg Leu Pro Gly Pro Tyr Thr Ar
g Glu Lys Gly Asp Leu
        35
                40
                        45

Glu Arg Glu Leu Ser Ala Leu Val Val Arg Il
e Glu Gln Leu Glu Thr
    50
        55
            60

Ala Ala Ile Ala Ala Ser Pro Pro Ala Met Pr
o Asp Thr Pro Asn Ala
65
70
75
80

Pro Thr Asp Ala Leu Phe Ser Asn Gly Thr Le
u Ser Pro Ser Ser Glu
                85
                        90
                                95

Thr Pro Asp Ala Arg Tyr Pro Ala Pro Leu Pr
o Arg Asn Gly Phe Ile
            100
                    105
                            110

Asp Glu Ala Leu Glu Gly Leu Arg Glu His Va
l Asp Asp Gln Ser Lys
        115
                120
                        125

Leu Leu Asp Ser Gln Arg Gln Glu Leu Ala Gl
y Val Asn Ala Gln Leu
    130
        135
            140

Ile Glu Gln Lys Gln Leu Gln Glu Lys Ala Le
u Ala Ile Ile Glu Gln
145             1
50              1
55              1
60

Glu Arg Val Ala Thr Leu Glu Arg Glu Leu Tr
p Lys His Gln Lys Ala
            165
                    170
                            175

Asn Glu Ala Phe Gln Lys Ala Leu Arg Glu Il
e Gly Glu Ile Val Thr
        180
                185
                        190

Ala Val Ala Arg Gly Asp Leu Ser Lys Lys Va
l Arg Met Asn Ser Val
```

-continued

```
            195
                200
                    205

Glu Met Asp Pro Glu Ile Thr Thr Phe Lys Ar
g Thr Ile Asn Thr Met
    210
        215
            220

Met Asp Gln Leu Gln Val Phe Ser Ser Glu Va
l Ser Arg Val Ala Arg
225                 2
30                      2
35                          2
40

Glu Val Gly Thr Glu Gly Ile Leu Gly Gly Gl
n Ala Gln Ile Glu Gly
            245
                250
                    255

Val Asp Gly Thr Trp Lys Glu Leu Thr Asp As
n Val Asn Val Met Ala
        260
            265
                270

Gln Asn Leu Thr Asp Gln Val Arg Glu Ile Al
a Ser Val Thr Thr Ala
    275
        280
            285

Val Ala His Gly Asp Leu Thr Lys Lys Ile Gl
u Arg Pro Ala Lys Gly
    290
        295
            300

Glu Ile Leu Gln Leu Gln Gln Thr Ile Asn Th
r Met Val Asp Gln Leu
305                 3
10                      3
15                          3
20

Arg Thr Phe Ala Ser Glu Val Thr Arg Val Al
a Arg Asp Val Gly Thr
                325
                    330
                        335

Glu Gly Ile Leu Gly Gly Gln Ala Asp Val Gl
u Gly Val Gln Gly Met
            340
                345
                    350

Trp Asn Glu Leu Thr Val Asn Val Asn Ala Me
t Ala Asn Asn Leu Thr
        355
            360
                365

Thr Gln Val Arg Asp Ile Ile Lys Val Thr Th
r Ala Val Ala Lys Gly
    370
        375
            380

Asp Leu Thr Gln Lys Val Gln Ala Glu Cys Ar
g Gly Glu Ile Phe Glu
385                 3
90                      3
95                          4
00

Leu Lys Lys Thr Ile Asn Ser Met Val Asp Gl
```

-continued n Leu Gln Gln Phe Ala
        405
            410
                415

Arg Glu Val Thr Lys Ile Ala Arg Glu Val Gl
y Thr Glu Gly Arg Leu
        420
            425
                430

Gly Gly Gln Ala Thr Val His Asp Val Gln Gl
y Thr Trp Arg Asp Leu
        435
            440
                445

Thr Glu Asn Val Asn Gly Met Ala Met Asn Le
u Thr Thr Gln Val Arg
        450
            455
                460

Glu Ile Ala Lys Val Thr Thr Ala Val Ala Ly
s Gly Asp Leu Thr Lys
465                 4
70              4
75          4
80

Lys Ile Gly Val Glu Val Gln Gly Glu Ile Le
u Asp Leu Lys Asn Thr
        485
            490
                495

Ile Asn Thr Met Val Asp Arg Leu Gly Thr Ph
e Ala Phe Glu Val Ser
        500
            505
                510

Lys Val Ala Arg Glu Val Gly Thr Asp Gly Th
r Leu Gly Gly Gln Ala
        515
            520
                525

Gln Val Asp Asn Val Glu Gly Lys Trp Lys As
p Leu Thr Glu Asn Val
        530
            535
                540

Asn Thr Met Ala Ser Asn Leu Thr Ser Gln Va
l Arg Gly Ile Ser Thr
545                 5
50              5
55          5
60

Val Thr Gln Ala Ile Ala Asn Gly Asp Met Se
r Arg Lys Ile Glu Val
        565
            570
                575

Glu Ala Lys Gly Glu Ile Leu Ile Leu Lys Gl
u Thr Ile Asn Asn Met
        580
            585
                590

Val Asp Arg Leu Ser Ile Phe Cys Asn Glu Va
l Gln Arg Val Ala Lys
        595
            600
                605

Asp Val Gly Val Asp Gly Ile Met Gly Gly Gl

```
n Ala Asp Val Ala Gly
    610
    615
    620

Leu Lys Gly Arg Trp Lys Glu Ile Thr Thr As
p Val Asn Thr Met Ala
625             6
30              6
35              6
40

Asn Asn Leu Thr Ala Gln Val Arg Ala Phe Gl
y Asp Ile Thr Asn Ala
            645
            650
            655

Ala Thr Asp Gly Asp Phe Thr Lys Leu Val Gl
u Val Glu Ala Ser Gly
        660
        665
        670

Glu Met Asp Glu Leu Lys Lys Lys Ile Asn Gl
n Met Val Tyr Asn Leu
        675
        680
        685

Arg Asp Ser Ile Gln Arg Asn Thr Gln Ala Ar
g Glu Ala Ala Glu Leu
    690
    695
    700

Ala Asn Lys Thr Lys Ser Glu Phe Leu Ala As
n Met Ser His Glu Ile
705             7
10              7
15              7
20

Arg Thr Pro Met Asn Gly Ile Ile Gly Met Th
r Gln Leu Thr Leu Asp
            725
            730
            735

Thr Asp Leu Thr Gln Tyr Gln Arg Glu Met Le
u Asn Ile Val Asn Ser
        740
        745
        750

Leu Ala Asn Ser Leu Leu Thr Ile Ile Asp As
p Ile Leu Asp Leu Ser
        755
        760
        765

Lys Ile Glu Ala Arg Arg Met Val Ile Glu Gl
u Ile Pro Tyr Thr Leu
    770
    775
    780

Arg Gly Thr Val Phe Asn Ala Leu Lys Thr Le
u Ala Val Lys Glu Thr
785             7
90              7
95              8
00

Glu Lys Phe Leu Asp Leu Thr Tyr Arg Val As
p His Ser Val Pro Asp
            805
            810
            815
```

His Val Val Gly Asp Ser Phe Arg Leu Arg Gl
n Ile Ile Leu Asn Leu
          820
          825
          830

Val Gly Asn Ala Ile Lys Phe Thr Glu His Gl
y Glu Val Ser Leu Thr
        835
        840
        845

Ile Gln Lys Ala Ser Ser Val Gln Cys Ser Th
r Glu Glu Tyr Ala Ile
      850
      855
      860

Glu Phe Val Val Ser Asp Thr Gly Ile Gly Il
e Pro Ala Asp Lys Leu
865                   8
70                    8
75                    8
80

Asp Leu Ile Phe Asp Thr Phe Gln Gln Ala As
p Gly Ser Met Thr Arg
              885
              890
              895

Lys Phe Gly Gly Thr Gly Leu Gly Leu Ser Il
e Ser Lys Arg Leu Val
          900
          905
          910

Asn Leu Met Gly Gly Asp Val Trp Val Lys Se
r Glu Tyr Gly Lys Gly
        915
        920
        925

Ser Lys Phe Phe Phe Thr Cys Val Val Arg Le
u Ala Asn Asp Asp Ile
      930
      935
      940

Ser Leu Ile Ala Lys Gln Leu Asn Pro Tyr Ly
s Ser His Gln Val Leu
945                   9
50                    9
55                    9
60

Phe Ile Asp Lys Gly Arg Thr Gly His Gly Pr
o Glu Ile Ala Lys Met
              965
              970
              975

Leu His Gly Leu Gly Leu Val Pro Ile Val Va
l Asp Ser Glu Arg Asn
          980
          985
          990

Pro Ala Leu Glu Lys Ala Arg Ala Ala Gly Gl
n Ala Pro Tyr Asp Val
        995
        1000
        1005

Ile Ile Val Asp Ser Ile Glu Asp Ala Arg Ar
g Leu Arg Ser Val Asp
      1010
      1015
      1020

-continued

Asp Phe Lys Tyr Leu Pro Ile Val Leu Leu Al
a Pro Val Val His Val
    1025                1030
            1035
                1040

Ser Leu Lys Ser Cys Leu Asp Leu Gly Ile Th
r Ser Tyr Met Thr Thr
            1045
                1050
                    1055

Pro Cys Gln Leu Ile Asp Leu Gly Asn Gly Me
t Val Pro Ala Leu Glu
                1060
                    1065
                        1070

Asn Arg Ala Thr Pro Ser Leu Ala Asp Asn Th
r Lys Ser Phe Glu Ile
            1075
                1080
                    1085

Leu Leu Ala Glu Asp Asn Thr Val Asn Gln Ar
g Leu Ala Val Lys Ile
        1090
            1095
                1100

Leu Glu Lys Tyr His His Val Val Thr Val Va
l Gly Asn Gly Glu Glu
    1105                1110
                1115
                    1120

Ala Val Glu Ala Val Lys Arg Lys Lys Phe As
p Val Ile Leu Met Asp
                1125
                    1130
                        1135

Val Gln Met Pro Ile Met Gly Gly Phe Glu Al
a Thr Ala Lys Ile Arg
                1140
                    1145
                        1150

Glu Tyr Glu Arg Ser Leu Gly Ser Gln Arg Th
r Pro Ile Ile Ala Leu
            1155
                1160
                    1165

Thr Ala His Ala Met Met Gly Asp Arg Glu Ly
s Cys Ile Gln Ala Gln
        1170
            1175
        1180

Met Asp Glu Tyr Leu Ser Lys Pro Leu Gln Gl
n Asn His Leu Ile Gln
    1185                1190
                1195
                    1200

Thr Ile Leu Lys Cys Ala Thr Leu Gly Gly Gl
n Leu Leu Glu Lys Asn
                1205
                    1210
                        1215

Arg Glu Arg Glu Leu Thr Arg Ala Ala Asp Al
a Val Thr Gly Gly Arg
                1220
                    1225
                        1230

Arg Asp Asn Gly Met Tyr Ser Ala Ser Gln Al
a Ala Gln His Ala Ala

```
                     1235
                 1240
             1245

Leu Arg Pro Pro Leu Ala Thr Arg Gly Leu Th
r Ala Ala Asp Ser Leu
     1250
        1255
     1260

Val Ser Gly Leu Glu Ser Pro Ser Ile Val Th
r Ala Asp Lys Glu Asp
1265               1270
             1275
          1280

Pro Leu Ser Arg Ala Arg Ala Ser Leu Ser Gl
u Pro Asn Ile His Lys
                 1285
             1290
          1295

Ala Ser (2) INFORMATION FOR SEQ ID NO:5:

(i) SEQUENCE CHARACTERISTICS:
        (A) LENGTH: 5697 base
pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

GGATCCGCCC TCCACCCTCG TCGTCCGCGC GCCGCCATTA TCCTTGTTGG CC
ATCGTCGG     60

CCCTGTCCCT TTCTCATCCC ATCCGTTTTC CCTTTCAGAA TTTCCCCATC CA
CGTGCCAT    120

CCATCTTCTC GACGAAGCCC TTTTCCGCAC TTGATTTACC TGAACGCTCC GT
CCACAGTA    180

CACTGTACAA GAGTTCCCCC GTCAACCTCA ACCTCCCTAG GTAGCAACTT GG
AAAAGAGG    240

ATGAAGAGAG AGTCGACTGA TGGGATAGGC AAAACAGTTG GGAGCGAAAA AG
AAAAGAAA    300

CAAAAACCAA AGCGACGCTA GGAAGAATCG AGTGCAGTGG TCAACGGCAC CA
AAACCATA    360

CCCGATTCAT TCAGCCATTC AACGCTCGGC GGGCGCCCCT GTTCCCCGTC GC
ACGGCACT    420

AACAGAACTA GCACTGTGCT CCTCCTCCTC CTCCTCCTCC TCCTCTAGCG CT
CCGACGGA    480

CTCTGCACCT GGAGTTTACA GACTGACACT GCACGCAGTG CCCTGCTGCG GC
CCCGACGA    540

GTCTGTCTTT GGTCTCCAGT CCCGTTCCAG TCCCGTCCAT CCAGGAGCCA GT
GATCTGAT    600

CCCATCCAAC CCAGTCGACC CAGTCCACGC CCGCTGCCAG CCAGTCGAGT CC
AGGCACCG    660

CTCGATAACT CTCCTCTTTC TCCGCCTCAC TCTCCCAACC ACAGTCCACC CA
CCGACCGG    720

GCCACCACCA CTCACCACCA CCACCACGGC CCGGACTTCT TCAACCGCAG CA
GCAGCGCA    780

AGGAGCCAGG CCCAGCAACA GATCAGCCAG CTCTCAGCAG CAGCAGCAGC AG
CAACAGCA    840
```

```
GCAGCAGTGC CAGCCCAGTC CAGTCCAGTC CAGTCCGCAG TCCGCCCGCA GT
CGTCAACG    900

ACTGACTGAC TGACTGAACC TGAGGACGAG ACTAGACTCG CTACCTACCT CT
ACCTACCT    960

ACCTACCTAC CTACCTACCT ACCCACCCAC CGGTGGCGGT GTCCCCAGTA CA
AATCCTAC    1020

TACCTGACCT ACCTTAGCCA CGGAGAAAAA GGGGAACAAA AACGGGCAAA AC
AAAATCTC    1080

CTACTGCCTC CTGCGCACCG AGGCGCACGT CGAGTCTCCG AGCCTGAAGC CT
CCGTCCAG    1140

CTCCACGTCC CGCTCTCCTT TCGCGATACA ATCCTTTTTT GAAAACACA AT
TCCCACCC    1200

ATCGCGGCGG GATATCTAGT ACAAACAGTG AGCCCACTCC CCACCAGCAC TG
TTCTTTCG    1260

TCTGAAACTG TCAATTATAC GCACGCGCTT GCTTTCTTCA CACCTTTGCT GA
CGATCCCC    1320

TGCTTCAAGA CCACCACAAA CCCGACGCTC TGCATGTGCA ATTTCGCAAC AT
AACCACAT    1380

CAAGCTACCC AACCAGCAAC ACAGCCCAGA GACCAGAGAT CGATTACAAC GC
CGCTCCCT    1440

ATTCTCTCGA GTCCATCTCC CATCTCGATT CAATTGAAAC CAACTTCTTA GA
CCCGCAAA    1500

CGCCCATGAA GTCGCAAGAG TCGATTGTTA CCCACTAGCT TCCGCGCCTT GC
CCGACTGC    1560

GTTTCCTGCT CTATTCCGTC CCCAAGGCTC ACGGCGCCAA CGGCCGTAGC CC
ACAATCAT    1620

GACTGACGGA CCAACTCTCG CAGCTATTGC TGCTCTCGTC AAATCCCTGG CT
GTCGACCC    1680

GGCCACTACC CAGACCTCTG GACTTCGCCC AAGCACCCAT GTCAGGCTTC CC
GGTCCGTA    1740

TACCCGTGAG AAGGGTGATC TGGAGCGTGA GCTCTCGGCT CTTGTTGTCC GC
ATAGAGCA    1800

GCTGGAGACT GCCGCCATCG CTGCCTCTCC TCCAGCCATG CCCGATACAC CA
AATGCGCC    1860

AACCGATGCG CTGTTTTCAA ACGGCACCCT TTCGCCATCC TCGGAAACGC CT
GATGCCCG    1920

CTACCCCGCT CCGCTACCGC GAAATGGCTT CATCGACGAG GCCCTTGAGG GT
CTCCGCGA    1980

GCATGTCGAC GACCAGTCCA AGCTGCTTGA CAGCCAGCGT CAGGAGCTTG CT
GGGGTCAA    2040

CGCCCAGCTG ATTGAGCAAA AGCAACTTCA GGAAAAGGCT CTGGCTATTA TC
GAACAGGA    2100

ACGGGTTGCT ACCCTTGAGC GGGAACTCTG GAAGCATCAA AAGGCCAACG AG
GCCTTCCA    2160

AAAGGCTCTC CGAGAAATCG GTGAGATTGT CACTGCCGTC GCCAGGGGTG AT
TTGTCCAA    2220

AAAGGTCCGG ATGAACTCGG TGGAAATGGA CCCGGAAATC ACCACCTTCA AG
CGTACGAT    2280

AAACACAATG ATGGACCAGT TGCAAGTCTT CTCCAGCGAA GTCTCGCGTG TC
GCTCGTGA    2340

AGTCGGAACC GAGGGTATTC TCGGTGGCCA AGCTCAGATC GAAGGCGTTG AC
GGCACCTG    2400

GAAGGAACTC ACAGACAACG GTATGTTTGA TCCCATCTTG ACAGCCGCAG GC
CGTAGTGG    2460
```

```
CCTATGTGTA CTGATCATAT CATCTAGTCA ACGTCATGGC CCAGAATCTT AC
CGACCAAG    2520

TGCGAGAGAT TGCTTCCGTA ACGACTGCTG TCGCTCATGG CGATCTTACC AA
GAAAATCG    2580

AGCGTCCCGC CAAGGGAGAA ATACTTCAAC TTCAACAAAC CATCAACACA AT
GGTGGATC    2640

AGCTACGGAC TTTCGCCTCT GAAGTTACAC GTGTCGCCAG AGATGTCGGT AC
CGAGGGTA    2700

TCCTCGGTGG TCAAGCCGAC GTTGAAGGAG TCCAGGGCAT GTGGAACGAA CT
TACGGTTA    2760

ATGTGAACGC CATGGCCAAC AATCTAACAA CCCAAGTCAG AGATATCATC AA
GGTTACTA    2820

CCGCTGTCGC CAAGGGTGAC CTTACTCAAA AGTACAAGC TGAATGCCGC GG
TGAGATTT    2880

TCGAACTGAA GAAGACTATC AACTCTATGG TGGACCAACT ACAACAATTT GC
TCGGGAAG    2940

TCACAAAGAT CGCCAGGGAA GTCGGAACCG AAGGAAGGCT CGGTGGGCAG GC
CACTGTTC    3000

ACGATGTTCA GGGTACTTGG AGGGACCTCA CCGAAAACGT CAACGGCATG GC
CATGAACT    3060

TGACCACACA GGTGCGAGAA ATCGCAAAGG TTACTACAGC CGTCGCCAAG GG
TGATTTGA    3120

CCAAGAAGAT TGGGGTCGAG GTTCAGGGTG AGATCCTGGA TTTGAAGAAC AC
CATCAACA    3180

CCATGGTTGA CCGTCTTGGT ACTTTCGCTT TCGAGGTCAG CAAGGTCGCC AG
GGAAGTCG    3240

GCACCGATGG TACCTTGGGT GGTCAGGCAC AGGTTGATAA TGTGGAGGGC AA
GTGGAAGG    3300

ATCTCACAGA GAACGTCAAC ACCATGGCCA GCAACCTTAC ATCTCAGGTA AG
CTGCTCCT    3360

AGATGATCCT TTGCGGCATG CACTGTTTGC TAACTTTTCA CAGGTCCGTG GG
ATCTCTAC    3420

CGTCACACAA GCCATTGCCA ATGGTGATAT GAGCCGCAAG ATTGAAGTTG AA
GCCAAGGG    3480

AGAGATACTC ATACTCAAGG AGACTATCAA CAACATGGTT GACCGACTCT CC
ATTTTCTG    3540

TAATGAGGTG CAGAGAGTCG CCAAGGATGT CGGTGTCGAT GGTATCATGG GA
GGACAAGC    3600

CGATGTTGCT GGCCTGAAGG GCAGGTGGAA GGAAATTACC ACCGATGTCA AC
ACAATGGC    3660

GAATAACTTG GTATGTCTCG CCGCCGCCAG CACCCTTGAA CAGCACCCCT TT
TTGCTAAT    3720

GCCTTTTACA GACGGCTCAA GTGAGAGCGT TCGGCGACAT CACAAATGCA GC
AACAGACG    3780

GGGACTTTAC AAAACTCGTC GAGGTAGAAG CCTCGGGCGA GATGGACGAA CT
CAAAAAGA    3840

AGATCAATCA GATGGTCTAC AATTTGAGGG ACAGTATTCA ACGTAATACC CA
GGCCAGGG    3900

AAGCCGCCGA ACTGGCCAAT AAGACCAAGT CCGAGTTTTT GGCGAACATG TC
CCACGAAA    3960

TACGCACACC CATGAACGGC ATTATCGGCA TGACACAACT TACTCTCGAT AC
TGACCTGA    4020

CACAGTATCA GAGAGAAATG CTCAACATTG TCAACTCCCT GGCCAACAGC TT
```

```
ACTGACCA    4080

TCATCGACGA CATTTTGGAT CTGTCCAAGA TCGAAGCTAG GCGTATGGTC AT
CGAAGAGA    4140

TTCCTTATAC GTTGCGTGGC ACCGTCTTCA ACGCGCTCAA GACTCTTGCC GT
CAAGGAAA    4200

CCGAGAAGTT TCTGGATCTT ACCTATCGTG TCGACCATTC TGTACCCGAC CA
CGTCGTCG    4260

GAGACTCCTT CAGGTTGCGC CAGATTATTC TTAACCTTGT TGGCAACGCT AT
CAAGTTCA    4320

CCGAGCATGG TGAAGTCAGT CTTACCATCC AGAAGGCCTC TTCAGTACAG TG
CAGCACCG    4380

AAGAGTACGC TATCGAGTTT GTCGTTTCCG ACACTGGTAT CGGTATTCCG GC
GGACAAGC    4440

TGGATCTCAT CTTCGACACT TTCCAGCAGG CCGATGGTTC AATGACTCGC AA
GTTTGGCG    4500

GTACTGGTCT CGGTCTCTCC ATTTCCAAGC GTCTTGTCAA CCTCATGGGT GG
TGACGTTT    4560

GGGTGAAGAG TGAGTATGGT AAGGGTAGCA AGTTCTTCTT CACCTGCGTG GT
CCGCTTGG    4620

CCAACGACGA TATTTCGTTG ATCGCCAAGC AGCTCAACCC TTACAAGAGT CA
CCAGGTCC    4680

TGTTCATCGA CAAGGGCCGC ACCGGACATG GACCGGAGAT CGCCAAGATG CT
CCACGGCT    4740

TGGGCCTCGT TCCCATCGTC GTCGACTCGG AGAGGAATCC TGCGCTCGAG AA
GGCCAGAG    4800

CTGCCGGCCA GGCGCCCTAC GACGTCATCA TTGTGGACTC GATCGAGGAT GC
AAGGCGCT    4860

TGCGGTCTGT TGACGACTTT AAGTACCTTC CCATCGTATT GCTAGCACCA GT
CGTTCACG    4920

TCTCGCTAAA GTCTTGCCTT GACTTGGGTA TCACGTCGTA CATGACGACG CC
TTGTCAAC    4980

TCATTGACCT CGGTAACGGC ATGGTCCCTG CTCTCGAAAA TAGGGCTACG CC
GTCGCTGG    5040

CGGACAACAC CAAATCTTTT GAGATCCTGC TTGCCGAAGA CAACACGGTC AA
CCAGAGGC    5100

TCGCGGTCAA GATCCTGGAG AAGTATCACC ACGTCGTCAC CGTTGTTGGA AA
CGGTGAAG    5160

AGGCTGTTGA GGCCGTCAAG AGGAAAAAGT TCGATGTCAT TCTTATGGAC GT
CCAGATGC    5220

CTATTATGGT GAGTCAAAGC TGTTTTTCAA ACCAAGAAGC CGATGCTAAC AA
TTTTCATA    5280

GGGCGGTTTC GAAGCTACGG CCAAGATTCG CGAGTACGAG CGCAGCCTCG GC
AGCCAGCG    5340

CACACCCATC ATCGCCCTCA CGGCGCATGC CATGATGGGT GACAGGGAAA AG
TGTATCCA    5400

GGCACAGATG GACGAGTATC TCTCCAAGCC GCTGCAGCAG AACCATCTAA TC
CAGACCAT    5460

ACTCAAGTGT GCGACGCTCG GCGGGCAACT ACTCGAGAAG AACCGGGAGC GC
GAGCTGAC    5520

CCGTGCTGCC GATGCCGTTA CAGGCGGCCG CCGCGACAAC GGCATGTACT CT
GCCAGCCA    5580

AGCCGCGCAG CACGCTGCGC TCCGCCCACC CCTCGCCACC AGGGGCCTCA CT
GCCGCCGA    5640
```

```
CAGCCTCGTC TCCGGCTTGG AGAGCCCATC CATCGTGACG GCGGATAAGG AG
GATCC       5697
```

(2) INFORMATION FOR SEQ ID NO:6:

(i) SEQUENCE CHARACTERISTICS:
        (A) LENGTH: 1281 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

```
Met Thr Asp Gly Pro Thr Leu Ala Ala Ile Ala Ala Leu Val Lys Ser
 1               5                  10                  15

Leu Ala Val Asp Pro Ala Thr Thr Gln Thr Ser Gly Leu Arg Pro Ser
                20                  25                  30

Thr His Val Arg Leu Pro Gly Pro Tyr Thr Arg Glu Lys Gly Asp Leu
            35                  40                  45

Glu Arg Glu Leu Ser Ala Leu Val Val Arg Ile Glu Gln Leu Glu Thr
        50                  55                  60

Ala Ala Ile Ala Ala Ser Pro Pro Ala Met Pro Asp Thr Pro Asn Ala
65                  70                  75                  80

Pro Thr Asp Ala Leu Phe Ser Asn Gly Thr Leu Ser Pro Ser Ser Glu
                85                  90                  95

Thr Pro Asp Ala Arg Tyr Pro Ala Pro Leu Pro Arg Asn Gly Phe Ile
               100                 105                 110

Asp Glu Ala Leu Glu Gly Leu Arg Glu His Val Asp Asp Gln Ser Lys
           115                 120                 125

Leu Leu Asp Ser Gln Arg Gln Glu Leu Ala Gly Val Asn Ala Gln Leu
       130                 135                 140

Ile Glu Gln Lys Gln Leu Gln Glu Lys Ala Leu Ala Ile Ile Glu Gln
145                 150                 155                 160
```

Glu Arg Val Ala Thr Leu Glu Arg Glu Leu Trp Lys His Gln Lys Ala
            165                 170                 175

Asn Glu Ala Phe Gln Lys Ala Leu Arg Glu Ile Gly Glu Ile Val Thr
        180                 185                 190

Ala Val Ala Arg Gly Asp Leu Ser Lys Lys Val Arg Met Asn Ser Val
    195                 200                 205

Glu Met Asp Pro Glu Ile Thr Thr Phe Lys Arg Thr Ile Asn Thr Met
210                 215                 220

Met Asp Gln Leu Gln Val Phe Ser Ser Glu Val Ser Arg Val Ala Arg
225                 230                 235                 240

Glu Val Gly Thr Glu Gly Ile Leu Gly Gly Gln Ala Gln Ile Glu Gly
            245                 250                 255

Val Asp Gly Thr Trp Lys Glu Leu Thr Asp Asn Val Asn Val Met Ala
        260                 265                 270

Gln Asn Leu Thr Asp Gln Val Arg Glu Ile Ala Ser Val Thr Thr Ala
    275                 280                 285

Val Ala His Gly Asp Leu Thr Lys Lys Ile Glu Arg Pro Ala Lys Gly
   290                 295                 300

Glu Ile Leu Gln Leu Gln Gln Thr Ile Asn Thr Met Val Asp Gln Leu
305                 310                 315                 320

Arg Thr Phe Ala Ser Glu Val Thr Arg Val Ala Arg Asp Val Gly Thr
            325                 330                 335

Glu Gly Ile Leu Gly Gly Gln Ala Asp Val Glu Gly Val Gln Gly Met
        340                 345                 350

Trp Asn Glu Leu Thr Val Asn Val Asn Ala Met Ala Asn Asn Leu Thr
    355                 360                 365

```
Thr Gln Val Arg Asp Ile Ile Lys Val Thr Th
r Ala Val Ala Lys Gly
    370
      375
        380

Asp Leu Thr Gln Lys Val Gln Ala Glu Cys Ar
g Gly Glu Ile Phe Glu
385                       3
90                          3
95                            4
00

Leu Lys Lys Thr Ile Asn Ser Met Val Asp Gl
n Leu Gln Gln Phe Ala
    405
      410
        415

Arg Glu Val Thr Lys Ile Ala Arg Glu Val Gl
y Thr Glu Gly Arg Leu
    420
      425
        430

Gly Gly Gln Ala Thr Val His Asp Val Gln Gl
y Thr Trp Arg Asp Leu
    435
      440
        445

Thr Glu Asn Val Asn Gly Met Ala Met Asn Le
u Thr Thr Gln Val Arg
    450
      455
        460

Glu Ile Ala Lys Val Thr Thr Ala Val Ala Ly
s Gly Asp Leu Thr Lys
465                       4
70                          4
75                            4
80

Lys Ile Gly Val Glu Val Gln Gly Glu Ile Le
u Asp Leu Lys Asn Thr
          485
            490
              495

Ile Asn Thr Met Val Asp Arg Leu Gly Thr Ph
e Ala Phe Glu Val Ser
        500
          505
            510

Lys Val Ala Arg Glu Val Gly Thr Asp Gly Th
r Leu Gly Gly Gln Ala
      515
        520
          525

Gln Val Asp Asn Val Glu Gly Lys Trp Lys As
p Leu Thr Glu Asn Val
    530
      535
        540

Asn Thr Met Ala Ser Asn Leu Thr Ser Gln Va
l Arg Gly Ile Ser Thr
545                       5
50                          5
55                            5
60

Val Thr Gln Ala Ile Ala Asn Gly Asp Met Se
r Arg Lys Ile Glu Val
          565
            570
              575
```

Glu Ala Lys Gly Glu Ile Leu Ile Leu Lys Gl
u Thr Ile Asn Asn Met
            580
                585
                    590

Val Asp Arg Leu Ser Ile Phe Cys Asn Glu Va
l Gln Arg Val Ala Lys
        595
            600
                605

Asp Val Gly Val Asp Gly Ile Met Gly Gly Gl
n Ala Asp Val Ala Gly
    610
        615
            620

Leu Lys Gly Arg Trp Lys Glu Ile Thr Thr As
p Val Asn Thr Met Ala
625                     6
30                          6
35                              6
40

Asn Asn Leu Thr Ala Gln Val Arg Ala Phe Gl
y Asp Ile Thr Asn Ala
            645
                650
                    655

Ala Thr Asp Gly Asp Phe Thr Lys Leu Val Gl
u Val Glu Ala Ser Gly
            660
                665
                    670

Glu Met Asp Glu Leu Lys Lys Lys Ile Asn Gl
n Met Val Tyr Asn Leu
        675
            680
                685

Arg Asp Ser Ile Gln Arg Asn Thr Gln Ala Ar
g Glu Ala Ala Glu Leu
    690
        695
            700

Ala Asn Lys Thr Lys Ser Glu Phe Leu Ala As
n Met Ser His Glu Ile
705                     7
10                          7
15                              7
20

Arg Thr Pro Met Asn Gly Ile Ile Gly Met Th
r Gln Leu Thr Leu Asp
                725
                    730
                        735

Thr Asp Leu Thr Gln Tyr Gln Arg Glu Met Le
u Asn Ile Val Asn Ser
            740
                745
                    750

Leu Ala Asn Ser Leu Leu Thr Ile Asp As
p Ile Leu Asp Leu Ser
        755
            760
                765

Lys Ile Glu Ala Arg Arg Met Val Ile Gl
u Ile Pro Tyr Thr Leu
    770
        775
            780

Arg Gly Thr Val Phe Asn Ala Leu Lys Thr Leu Ala Val Lys Glu Thr
785                       790                   795                   800

Glu Lys Phe Leu Asp Leu Thr Tyr Arg Val Asp His Ser Val Pro Asp
            805               810               815

His Val Gly Asp Ser Phe Arg Leu Arg Gln Ile Ile Leu Asn Leu
            820               825               830

Val Gly Asn Ala Ile Lys Phe Thr Glu His Gly Glu Val Ser Leu Thr
            835               840               845

Ile Gln Lys Ala Ser Ser Val Gln Cys Ser Thr Glu Glu Tyr Ala Ile
            850               855               860

Glu Phe Val Val Ser Asp Thr Gly Ile Gly Ile Pro Ala Asp Lys Leu
865                       870                   875                   880

Asp Leu Ile Phe Asp Thr Phe Gln Gln Ala Asp Gly Ser Met Thr Arg
            885               890               895

Lys Phe Gly Gly Thr Gly Leu Gly Leu Ser Ile Ser Lys Arg Leu Val
            900               905               910

Asn Leu Met Gly Gly Asp Val Trp Val Lys Ser Glu Tyr Gly Lys Gly
            915               920               925

Ser Lys Phe Phe Phe Thr Cys Val Val Arg Leu Ala Asn Asp Asp Ile
            930               935               940

Ser Leu Ile Ala Lys Gln Leu Asn Pro Tyr Lys Ser His Gln Val Leu
945                       950                   955                   960

Phe Ile Asp Lys Gly Arg Thr Gly His Gly Pro Glu Ile Ala Lys Met
            965               970               975

Leu His Gly Leu Gly Leu Val Pro Ile Val Val Asp Ser Glu Arg Asn
            980               985

```
                        990
Pro Ala Leu Glu Lys Ala Arg Ala Ala Gly Gl
n Ala Pro Tyr Asp Val
        995
         1000
          1005

Ile Ile Val Asp Ser Ile Glu Asp Ala Arg Ar
g Leu Arg Ser Val Asp
     1010
      1015
       1020

Asp Phe Lys Tyr Leu Pro Ile Val Leu Leu Al
a Pro Val Val His Val
1025              1030
         1035
          1040

Ser Leu Lys Ser Cys Leu Asp Leu Gly Ile Th
r Ser Tyr Met Thr Thr
          1045
           1050
            1055

Pro Cys Gln Leu Ile Asp Leu Gly Asn Gly Me
t Val Pro Ala Leu Glu
          1060
           1065
            1070

Asn Arg Ala Thr Pro Ser Leu Ala Asp Asn Th
r Lys Ser Phe Glu Ile
        1075
         1080
          1085

Leu Leu Ala Glu Asp Asn Thr Val Asn Gln Ar
g Leu Ala Val Lys Ile
      1090
       1095
  1100

Leu Glu Lys Tyr His His Val Val Thr Val Va
l Gly Asn Gly Glu Glu
1105              1110
            1115
             1120

Ala Val Glu Ala Val Lys Arg Lys Lys Phe As
p Val Ile Leu Met Asp
          1125
           1130
            1135

Val Gln Met Pro Ile Met Gly Gly Phe Glu Al
a Thr Ala Lys Ile Arg
           1140
            1145
             1150

Glu Tyr Glu Arg Ser Leu Gly Ser Gln Arg Th
r Pro Ile Ile Ala Leu
         1155
          1160
           1165

Thr Ala His Ala Met Met Gly Asp Arg Glu Ly
s Cys Ile Gln Ala Gln
         1170
          1175
           1180

Met Asp Glu Tyr Leu Ser Lys Pro Leu Gln Gl
n Asn His Leu Ile Gln
1185              1190
            1195
             1200
```

```
Thr Ile Leu Lys Cys Ala Thr Leu Gly Gly Gl
n Leu Leu Glu Lys Asn
            1205
            1210
        1215

Arg Glu Arg Glu Leu Thr Arg Ala Ala Asp Al
a Val Thr Gly Gly Arg
        1220
        1225
        1230

Arg Asp Asn Gly Met Tyr Ser Ala Ser Gln Al
a Ala Gln His Ala Ala
        1235
       1240
     1245

Leu Arg Pro Pro Leu Ala Thr Arg Gly Leu Th
r Ala Ala Asp Ser Leu
    1250
   1255
  1260

Val Ser Gly Leu Glu Ser Pro Ser Ile Val Th
r Ala Asp Lys Glu Asp
1265             1270
            1275
            1280

Pro (2) INFORMATION FOR SEQ ID NO:7:

(i) SEQUENCE CHARACTERISTICS:
        (A) LENGTH: 19 base
pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc
= "DNA"

(ix) FEATURE:
        (A) NAME/KEY: modified_
base
        (B) LOCATION: 6
        (D) OTHER INFORMATION:
/mod_base= OTHER
            /note=
"The residue at this position is deoxyinosine."

(ix) FEATURE:
        (A) NAME/KEY: modified_
base
        (B) LOCATION: 9
        (D) OTHER INFORMATION:
/mod_base= OTHER
            /note=
"The residue at this position is deoxyinosine."

(ix) FEATURE:
        (A) NAME/KEY: modified_
base
        (B) LOCATION: 12
        (D) OTHER INFORMATION:
/mod_base= OTHER
            /note=
"The residue at this position is deoxyinosine."

(ix) FEATURE:
        (A) NAME/KEY: modified_
base
        (B) LOCATION: 15
        (D) OTHER INFORMATION:
/mod_base= OTHER
            /note=
```

"The residue at this position is deoxyinosine."

(ix) FEATURE:
         (A) NAME/KEY: modified_base
         (B) LOCATION: 17
         (D) OTHER INFORMATION:
/mod_base= OTHER
         /note=
"The residue at this position is deoxyinosine."

(xi) SEQUENCE DESCRIPTION: SEQ ID NO:7:

CAYGANHTNM GNACNCNCC

19

(2) INFORMATION FOR SEQ ID NO:8:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(ix) FEATURE:
         (A) NAME/KEY: modified_base
         (B) LOCATION: 9
         (D) OTHER INFORMATION:
/mod_base= OTHER
         /note=
"The residue at this position is deoxyinosine."

(ix) FEATURE:
         (A) NAME/KEY: modified_base
         (B) LOCATION: 11..12
         (D) OTHER INFORMATION:
/mod_base= OTHER
         /note=
"The residue at this position is deoxyinosine."

(xi) SEQUENCE DESCRIPTION: SEQ ID NO:8:

GTRAAYTTNA NNGCRTT

17

(2) INFORMATION FOR SEQ ID NO:9:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(ix) FEATURE:
         (A) NAME/KEY: modified_base
         (B) LOCATION: 6
         (D) OTHER INFORMATION:
/mod_base= OTHER
         /note=
"The residue at this position is deoxyinosine."

```
    (ix) FEATURE:
         (A) NAME/KEY: modified_
base
         (B) LOCATION: 9
         (D) OTHER INFORMATION:
/mod_base= OTHER
              /note=
"The residue at this position is deoxyinosine."

(ix) FEATURE:
         (A) NAME/KEY: modified_
base
         (B) LOCATION: 12
         (D) OTHER INFORMATION:
/mod_base= OTHER
              /note=
"The residue at this position is deoxyinosine."

(xi) SEQUENCE DESCRIPTION: SEQ ID NO:9:

GCRTTNCYNA CNARRTT

17

(2) INFORMATION FOR SEQ ID NO:10:

(i) SEQUENCE CHARACTERISTICS:
         (A) LENGTH: 20 base
pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc
= "DNA"

(xi) SEQUENCE DESCRIPTION: SEQ ID NO:10:

GAGAGCTGGC TGATCTGTTG

20

(2) INFORMATION FOR SEQ ID NO:11:

(i) SEQUENCE CHARACTERISTICS:
         (A) LENGTH: 6 amino
acids
         (B) TYPE: amino acid
         (C) STRANDEDNESS: Not R
elevant
         (D) TOPOLOGY: linear (ii) MOLECULE TYPE: peptide (ix) FEATURE:
         (A) NAME/KEY: Modified-sit
e
         (B) LOCATION: 2
         (D) OTHER INFORMATION:
/product= "OTHER"
              /note=
"The amino acid at this position can be eith
er
              Glutamic
Acid or Aspartic Acid."

(ix) FEATURE:
         (A) NAME/KEY: Modified-sit
e
         (B) LOCATION: 3
         (D) OTHER INFORMATION:
/product= "OTHER"
              /note=
"The amino acid at this position can be eith
er
```

Methionine,
Isoleucine, Leucine or Phenylalanine."

(xi) SEQUENCE DESCRIPTION: SEQ ID NO:11:

His Xaa Xaa Arg Thr Pro
1               5

(2) INFORMATION FOR SEQ ID NO:12:

(i) SEQUENCE CHARACTERISTICS:
        (A) LENGTH: 10 amino
acids
        (B) TYPE: amino acid
        (C) STRANDEDNESS: Not R
elevant
        (D) TOPOLOGY: linear (ii) MOLECULE TYPE: peptide (ix) FEATURE:
        (A) NAME/KEY: Modified-sit
e
        (B) LOCATION: 4
        (D) OTHER INFORMATION:
/product= "OTHER"
            /note=
"The amino acid at this position can be eith
er
            Serine or
 Glycine."

(ix) FEATURE:
        (A) NAME/KEY: Modified-sit
e
        (B) LOCATION: 7
        (D) OTHER INFORMATION:
/product= "OTHER"
            /note=
"The amino acid at this position can be eith
er
            Isoleucine
or Valine."

(xi) SEQUENCE DESCRIPTION: SEQ ID NO:12:

Asn Leu Val Xaa Asn Ala Xaa Lys Phe Thr
1               5
                10

(2) INFORMATION FOR SEQ ID NO:13:

(i) SEQUENCE CHARACTERISTICS:
        (A) LENGTH: 48 base
pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc
= "DNA"

(xi) SEQUENCE DESCRIPTION: SEQ ID NO:13:

AGTCAGTCAG TCAGTCAGTC AGTCGATCGA TCGATCGATC GATCGATC
            48

(2) INFORMATION FOR SEQ ID NO:14:

(i) SEQUENCE CHARACTERISTICS:
        (A) LENGTH: 15 base
pairs
        (B) TYPE: nucleic acid
        (C) STRANDEDNESS: single
        (D) TOPOLOGY: linear

```
        (ii) MOLECULE TYPE: other nucleic acid
             (A) DESCRIPTION: /desc
= "DNA"

(xi) SEQUENCE DESCRIPTION: SEQ ID NO:14:

GCCCACAATC ATGAC

15

(2) INFORMATION FOR SEQ ID NO:15:

(i) SEQUENCE CHARACTERISTICS:
             (A) LENGTH: 17 base
pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc
= "DNA"

(xi) SEQUENCE DESCRIPTION: SEQ ID NO:15:

GTCCTCCAAG TACCCTG

17

(2) INFORMATION FOR SEQ ID NO:16:

(i) SEQUENCE CHARACTERISTICS:
             (A) LENGTH: 18 base
pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc
= "DNA"

(xi) SEQUENCE DESCRIPTION: SEQ ID NO:16:

GATCAGCTAC GGACTTTC

18

(2) INFORMATION FOR SEQ ID NO:17:

(i) SEQUENCE CHARACTERISTICS:
             (A) LENGTH: 4453 base
pairs
             (B) TYPE: nucleic acid
             (C) STRANDEDNESS: Not R
elevant
             (D) TOPOLOGY: Not Relev
ant (ii) MOLECULE TYPE: DNA (genomic)

(xi) SEQUENCE DESCRIPTION: SEQ ID NO:17:

GTGGAGGTGA TGGGTGGTTG ATGAAGAGGA AGAGGAGTTA TGAAAGTTGT GG
GCACACGC        60

GTTTTTTTTT TTTTTTTGCT TCTTCCTTTT TTTAGGTCGC GCACCAATTA CT
AATTAGAT        120

TATTTTTGCT ATTACTGGGC AAATTGGATG TGGCAGATAT CTGCAACACA GT
ATCCGGAT        180

ATTAGTCATG GGGCATGTCA GATACTAGTA GGGTATGGCA GTTGGATGCG TG
TAGGGGTA        240
```

-continued

```
CTGGGCAGGG CCCGGTAAAG GAAACTAAAC ATGTTAGCCA GGGAGTGAGG TC
CTACGGGG    300

GGGAGCATAG TACACCAGTA GTAGGACCTC CTTTGTTGGT CGTGTGTGGT GG
CAATATAC    360

AAAGCCCCCC CTTACATCAA CAAAAAATTT TTCCTCTCTG TTGTTTATCT CG
AGTTTCTC    420

CCTCTCTCTC CAATGAACCC CACTAAAAAA CCACGGTTAT CACCAATGCA GC
CCTCTGTT    480

TTTGAAATAC TCAACGACCC TGAGCTTTAT AGTCAGCACT GTCATAGCCT TA
GGGAAACA    540

CTTCTTGATC ATTTCAACCA TCAAGCTACA CTTATCGACA CTTATGAACA TG
AACTAGAA    600

AAATCCAAAA ATGCCAACAA AGCGTTCCAA CAAGCACTTA GTGAAATAGG TA
CAGTTGTT    660

ATATCTGTTG CCATGGGAGA CTTGTCCAAA AAGTTGAGA TTCACACAGT AG
AAAATGAC    720

CCTGAGATTT TAAAAGTCAA AATCACCATC AACACCATGA TGGATCAATT AC
AGACATTT    780

GCTAATGAGG TTACAAAAGT CGCCACCGAA GTCGCAAATG GTGAACTAGG TG
GACAAGCG    840

AAAAATGATG GATCTGTTGG TATTTGGAGA TCACTTACAG ACAATGTTAA TA
TTATGGCT    900

CTTAATTTAA CTAACCAAGT GCGAGAAATT GCTGATGTCA CACGTGCTGT TG
CCAAGGGG    960

GACTTGTCAC GTAAAATTAA TGTACACGCC CAGGGTGAAA TCCTTCAACT TC
AACGTACA    1020

ATAAACACCA TGGTGGATCA GTTACGAACG TTTGCATTCG AAGTATCTAA AG
TTGCTAGA    1080

GATGTTGGTG TGCTTGGTAT ATTAGGAGGA CAAGCGTTGA TTGAAAATGT TG
AAGGTATT    1140

TGGGAAGAGT TGACTGATAA TGTCAATGCT ATGGCTCTTA ATTTGACTAC AC
AAGTGAGA    1200

AATATTGCCA ATGTCACCAC TGCCGTTGCC AAGGGGATT TGTCGAAAAA AG
TCACTGCT    1260

GATTGTAAGG GAGAAATTCT TGATTTGAAA CTTACTATTA ATCAAATGGT GG
ACCGATTA    1320

CAGAATTTTG CTCTTGCGGT GACGACATTG TCGAGAGAGG TTGGTACTTT GG
GTATTTTG    1380

GGTGGACAAG CTAACGTACA GGATGTTGAA GGTGCTTGGA AACAGGTTAC AG
AAAATGTC    1440

AACCTAATGG CTACTAATTT AACTAACCAA GTGAGATCTA TTGCTACAGT TA
CTACTGCA    1500

GTTGCGCATG GTGATTTGTC GCAAAAGATT GATGTTCATG CCCAGGGAGA GA
TTTTACAA    1560

TTGAAAAATA CAATCAACAA GATGGTGGAC TCTTTGCAGT TGTTTGCATC AG
AAGTGTCG    1620

AAAGTGGCAC AAGATGTTGG TATTAATGGA AAATTAGGTA TTCAAGCACA AG
TTAGTGAT    1680

GTTGATGGAT TATGGAAGGA AATTACGTCT AATGTAAATA CCATGGCTTC AA
ATTTAACT    1740

TCGCAAGTGA GAGCTTTTGC ACAGATTACT GCTGCTGCTA CTGATGGGGA TT
TCACTAGA    1800

TTTATTACTG TTGAAGCACT GGGAGAGATG GATGCGTTGA AAACAAAGAT TA
```

-continued

```
ATCAAATG         1860

GTGTTTAACT TAAGGGAATC GCTTCAAAGG AATACTGCGG CTAGAGAAGC TG
CTGAGTTG         1920

GCCAATAGTG CGAAATCCGA GTTTTTAGCA AACATGTCGC ATGAGATTAG AA
CACCATTG         1980

AATGGGATTA TTGGTATGAC TCAGTTGTCG CTTGATACAG AGTTGACACA GT
ACCAACGA         2040

GAGATGTTGT CGATTGTGCA TAACTTGGCA AATTCCTTGT TGACCATTAT AG
ACGATATA         2100

TTGGATATTT CTAAGATTGA GGCGAATAGA ATGACGGTGG AACAGATTGA TT
TTTCATTA         2160

AGAGGGACAG TGTTTGGTGC ATTGAAAACG TTAGCCGTCA AAGCTATTGA AA
AAAACCTA         2220

GACTTGACCT ATCAATGTGA TTCATCGTTT CCAGATAATC TTATTGGAGA TA
GTTTTAGA         2280

TTACGACAAG TTATTCTTAA CTTGGCTGGT AATGCTATTA AGTTTACTAA AG
AGGGAAA          2340

GTTAGTGTTA GTGTGAAAAA GTCTGATAAA ATGGTGTTAG ATAGTAAGTT GT
TGTTAGAG         2400

GTTTGTGTTA GCGACACGGG AATAGGTATA GAGAAAGACA AATTGGGATT GA
TTTTCGAT         2460

ACCTTCTGTC AAGCTGATGG TTCTACTACA AGAAAGTTTG GTGGTACAGG TT
TAGGGTTG         2520

TCAATTTCCA AACAGTTGAT ACATTTAATG GGTGGAGAGA TATGGGTTAC CT
CGGAGTAT         2580

GGATCCGGGT CAAACTTTTA TTTTACGGTG TGCGTGTCGC CATCTAATAT TA
GATATACT         2640

CGACAAACCG AACAATTGTT ACCATTTAGT TCCCATTATG TGTTATTTGT AT
CGACTGAG         2700

CATACTCAAG AAGAACTTGA TGTGTTGAGA GATGGAATTA TAGAACTTGG AT
TGATACCT         2760

ATAATTGTGA GAAATATTGA AGATGCAACA TTGACTGAGC CGGTGAAATA TG
ATATAATT         2820

ATGATTGATT CGATAGAGAT TGCCAAAAAG TTGAGGTTGT TATCAGAGGT TA
AATATATT         2880

CCGTTGGTTT TGGTCCATCA TTCTATTCCA CAGTTGAATA TGAGAGTATG TA
TTGATTTG         2940

GGGATATCTT CCTATGCAAA TACGCCATGT TCGATCACGG ACTTGGCCAG TG
CGATTATA         3000

CCAGCGTTGG AGTCGAGATC TATATCACAG AACTCAGACG AGTCGGTGAG GT
ACAAAATA         3060

TTACTAGCAG AGGACAACCT CGTCAATCAG AAACTTGCAG TTAGGATATT AG
AAAAGCAA         3120

GGGCATCTGG TGGAAGTAGT TGAGAACGGA CTCGAGGCGT ACGAAGCGAT TA
AGAGGAAT         3180

AAATATGATG TGGTGTTGAT GGATGTGCAA ATGCCTGTAA TGGGTGGGTT TG
AAGCTACG         3240

GAGAAGATTC GACAATGGGA GAAAAGTCT AACCCAATTG ACTCGTTGAC GT
TTAGGACT         3300

CCAATTATTG CCCTCACTGC ACACGCCATG TTAGGTGATA GAGAAAGTC AT
TGGCCAAG         3360

GGGATGGACG ATTATGTGAG TAAGCCATTG AAGCCGAAAT TGTTAATGCA GA
CGATAAAC         3420
```

```
AAGTGTATTC ATAATATTAA CCAGTTGAAA GAATTGTCGA GAAATAGTAG AG
GTAGCGAT    3480

TTTGCAAAGA AGATGACCCG AAACACACCT GGAAGCACGA CCCGTCAGGG GA
GTGATGAG    3540

GGGAGTGTAG AGGACATGAT TGGGGACACT CCCCGTCAAG GGAGTGTTGA GG
GAGGGGGT    3600

ACAAGTAGTA GACCAGTACA GAGAAGGTCT GCCACAGAGG GGTCGATCAC TA
CAATTAGT    3660

GAACAAATCG ACCGTTAGCT AACGACTCAA GCGTCAGCTT GAGTCAAAGC TA
CAAATATT    3720

TAGCCAATTG TATACTTAGA TAAATAAAAT ACAAGTAAAC CATTGTTGTG TT
TAGATCAA    3780

TAATTGAAAA ATAAACAAGA TTACTAAAAA TATCAAGCCA AATTGTTGTG TA
GGAACTGG    3840

GGTTTTTTTT TTGGGGTAAA CTTTTTTACC AAAAAATGGA TAAAAAGGG GA
TGTGGTCC    3900

CAGTAGTAAC TTTAGTGACT GTTTAGGTTA CTTGAGCTAT CCAAGTAGAA TG
TCAGCCCC    3960

CGCAGTAAGT TTGGTCTTAT TGTTTACGGA AAAATAAGAA CCTTAGCCCT GA
ACTAGCCC    4020

CTACCTAGTT TTGATGTGAA AAATTTTTTT TTTTTTTTTA TTGACGTTCT CC
CCCCCTAG    4080

ACCAATCGAA AGCCGTGGTA TTATTCCGGG CTTTGAAGAA AAGTCTTTCT TT
TTTTCTTT    4140

TTTTTTGTAT GGGCGCCACA GTTTATGCAA CATCACGTGA CCTTCTCTCA GC
AAAAAAAA    4200

ACCATTTATA TATTCCTTCT CATCCTCGCA GATGAGAGAC AAAAAACAAA CA
AAAAAAAA    4260

AAAATCTTTT TTTTTCGCCA CGCACACTAC CATGTCGCAA CAACCACATT TA
CGTCTCGG    4320

ATCTACCGCA CCTGATTTCA AAGCTGATAC AACTAACGGG CCTATTCTGT TT
CACGAAAT    4380

ACATTGGTGA TAGCTGGGCT ATCTTGTTCT CACATCCCGC CGCTCGAACC AT
GTGTGTAC    4440

ACCGACCTTT CTG

4453

(2) INFORMATION FOR SEQ ID NO:18:

(i) SEQUENCE CHARACTERISTICS:
        (A) LENGTH: 1081 amino
acids
        (B) TYPE: amino acid
        (C) STRANDEDNESS: Not R
elevant
        (D) TOPOLOGY: Not Relev
ant (ii) MOLECULE TYPE: peptide (xi) SEQUENCE DESCRIPTION: SEQ ID NO:18:

Met Asn Pro Thr Lys Lys Pro Arg Leu Ser Pr
o Met Gln Pro Ser Val
1               5
                10
                15

Phe Glu Ile Leu Asn Asp Pro Glu Leu Tyr Se
r Gln His Cys His Ser
```

```
                    20
                    25
                    30

Leu Arg Glu Thr Leu Leu Asp His Phe Asn Hi
s Gln Ala Thr Leu Ile
        35
        40
        45

Asp Thr Tyr Glu His Glu Leu Glu Lys Ser Ly
s Asn Ala Asn Lys Ala
    50
    55
    60

Phe Gln Gln Ala Leu Ser Glu Ile Gly Thr Va
l Val Ile Ser Val Ala
65
70
75
80

Met Gly Asp Leu Ser Lys Lys Val Glu Ile Hi
s Thr Val Glu Asn Asp
            85
            90
            95

Pro Glu Ile Leu Lys Val Lys Ile Thr Ile As
n Thr Met Met Asp Gln
        100
        105
        110

Leu Gln Thr Phe Ala Asn Glu Val Thr Lys Va
l Ala Thr Glu Val Ala
    115
    120
    125

Asn Gly Glu Leu Gly Gly Gln Ala Lys Asn As
p Gly Ser Val Gly Ile
    130
    135
    140

Trp Arg Ser Leu Thr Asp Asn Val Asn Ile Me
t Ala Leu Asn Leu Thr
145                                       1
50                        1
55                                1
60

Asn Gln Val Arg Glu Ile Ala Asp Val Thr Ar
g Ala Val Ala Lys Gly
                165
                170
                175

Asp Leu Ser Arg Lys Ile Asn Val His Ala Gl
n Gly Glu Ile Leu Gln
        180
        185
        190

Leu Gln Arg Thr Ile Asn Thr Met Val Asp Gl
n Leu Arg Thr Phe Ala
        195
        200
        205

Phe Glu Val Ser Lys Val Ala Arg Asp Val Gl
y Val Leu Gly Ile Leu
    210
    215
    220

Gly Gly Gln Ala Leu Ile Glu Asn Val Glu Gl
y Ile Trp Glu Glu Leu
```

```
225             2
30              2
35              2
40
Thr Asp Asn Val Asn Ala Met Ala Leu Asn Le
u Thr Thr Gln Val Arg
             245
             250
             255

Asn Ile Ala Asn Val Thr Thr Ala Val Ala Ly
s Gly Asp Leu Ser Lys
             260
             265
             270

Lys Val Thr Ala Asp Cys Lys Gly Glu Ile Le
u Asp Leu Lys Leu Thr
             275
             280
             285

Ile Asn Gln Met Val Asp Arg Leu Gln Asn Ph
e Ala Leu Ala Val Thr
         290
         295
         300

Thr Leu Ser Arg Glu Val Gly Thr Leu Gly Il
e Leu Gly Gly Gln Ala
305             3
10              3
15              3
20

Asn Val Gln Asp Val Glu Gly Ala Trp Lys Gl
n Val Thr Glu Asn Val
             325
             330
             335

Asn Leu Met Ala Thr Asn Leu Thr Asn Gln Va
l Arg Ser Ile Ala Thr
             340
             345
             350

Val Thr Thr Ala Val Ala His Gly Asp Leu Se
r Gln Lys Ile Asp Val
         355
         360
         365

His Ala Gln Gly Glu Ile Leu Gln Leu Lys As
n Thr Ile Asn Lys Met
     370
     375
     380

Val Asp Ser Leu Gln Leu Phe Ala Ser Glu Va
l Ser Lys Val Ala Gln
385             3
90              3
95              4
00

Asp Val Gly Ile Asn Gly Lys Leu Gly Ile Gl
n Ala Gln Val Ser Asp
             405
             410
             415

Val Asp Gly Leu Trp Lys Glu Ile Thr Ser As
n Val Asn Thr Met Ala
             420
             425
             430

Ser Asn Leu Thr Ser Gln Val Arg Ala Phe Al
``` a Gln Ile Thr Ala Ala
       435
         440
             445

Ala Thr Asp Gly Asp Phe Thr Arg Phe Ile Th
r Val Glu Ala Leu Gly
     450
       455
           460

Glu Met Asp Ala Leu Lys Thr Lys Ile Asn Gl
n Met Val Phe Asn Leu
465            4
70           4
75         4
80

Arg Glu Ser Leu Gln Arg Asn Thr Ala Ala Ar
g Glu Ala Ala Glu Leu
           485
             490
               495

Ala Asn Ser Ala Lys Ser Glu Phe Leu Ala As
n Met Ser His Glu Ile
         500
           505
             510

Arg Thr Pro Leu Asn Gly Ile Ile Gly Met Th
r Gln Leu Ser Leu Asp
       515
         520
           525

Thr Glu Leu Thr Gln Tyr Gln Arg Glu Met Le
u Ser Ile Val His Asn
     530
       535
         540

Leu Ala Asn Ser Leu Leu Thr Ile Ile Asp As
p Ile Leu Asp Ile Ser
545              5
50           5
55             5
60

Lys Ile Glu Ala Asn Arg Met Thr Val Glu Gl
n Ile Asp Phe Ser Leu
           565
             570
               575

Arg Gly Thr Val Phe Gly Ala Leu Lys Thr Le
u Ala Val Lys Ala Ile
             580
               585
                 590

Glu Lys Asn Leu Asp Leu Thr Tyr Gln Cys As
p Ser Ser Phe Pro Asp
       595
         600
           605

Asn Leu Ile Gly Asp Ser Phe Arg Leu Arg Gl
n Val Ile Leu Asn Leu
     610
       615
         620

Ala Gly Asn Ala Ile Lys Phe Thr Lys Glu Gl
y Lys Val Ser Val Ser
625              6
30           6
35             6
40

Val Lys Lys Ser Asp Lys Met Val Leu Asp Ser Lys Leu Leu Leu Glu
                645                 650                 655

Val Cys Val Ser Asp Thr Gly Ile Gly Ile Glu Lys Asp Lys Leu Gly
            660                 665                 670

Leu Ile Phe Asp Thr Phe Cys Gln Ala Asp Gly Ser Thr Thr Arg Lys
        675                 680                 685

Phe Gly Gly Thr Gly Leu Gly Leu Ser Ile Ser Lys Gln Leu Ile His
    690                 695                 700

Leu Met Gly Gly Glu Ile Trp Val Thr Ser Glu Tyr Gly Ser Gly Ser
705                 710                 715                 720

Asn Phe Tyr Phe Thr Val Cys Val Ser Pro Ser Asn Ile Arg Tyr Thr
                725                 730                 735

Arg Gln Thr Glu Gln Leu Leu Pro Phe Ser Ser His Tyr Val Leu Phe
            740                 745                 750

Val Ser Thr Glu His Thr Gln Glu Glu Leu Asp Val Leu Arg Asp Gly
        755                 760                 765

Ile Ile Glu Leu Gly Leu Ile Pro Ile Ile Val Arg Asn Ile Glu Asp
    770                 775                 780

Ala Thr Leu Thr Glu Pro Val Lys Tyr Asp Ile Ile Met Ile Asp Ser
785                 790                 795                 800

Ile Glu Ile Ala Lys Lys Leu Arg Leu Leu Ser Glu Val Lys Tyr Ile
                805                 810                 815

Pro Leu Val Leu Val His His Ser Ile Pro Gln Leu Asn Met Arg Val
            820                 825                 830

Cys Ile Asp Leu Gly Ile Ser Ser Tyr Ala Asn Thr Pro Cys Ser Ile
        835                 840                 845

```
Thr Asp Leu Ala Ser Ala Ile Ile Pro Ala Le
u Glu Ser Arg Ser Ile
    850
    855
    860

Ser Gln Asn Ser Asp Glu Ser Val Arg Tyr Ly
s Ile Leu Leu Ala Glu
865                    8
70                     8
75                     8
80

Asp Asn Leu Val Asn Gln Lys Leu Ala Val Ar
g Ile Leu Glu Lys Gln
        885
        890
        895

Gly His Leu Val Glu Val Val Glu Asn Gly Le
u Glu Ala Tyr Glu Ala
        900
        905
        910

Ile Lys Arg Asn Lys Tyr Asp Val Val Leu Me
t Asp Val Gln Met Pro
        915
        920
        925

Val Met Gly Gly Phe Glu Ala Thr Glu Lys Il
e Arg Gln Trp Glu Lys
    930
    935
    940

Lys Ser Asn Pro Ile Asp Ser Leu Thr Phe Ar
g Thr Pro Ile Ile Ala
945                    9
50                     9
55                     9
60

Leu Thr Ala His Ala Met Leu Gly Asp Arg Gl
u Lys Ser Leu Ala Lys
        965
        970
        975

Gly Met Asp Asp Tyr Val Ser Lys Pro Leu Ly
s Pro Lys Leu Leu Met
        980
        985
        990

Gln Thr Ile Asn Lys Cys Ile His Asn Ile As
n Gln Leu Lys Glu Leu
        995
        1000
        1005

Ser Arg Asn Ser Arg Gly Ser Asp Phe Ala Ly
s Lys Met Thr Arg Asn
    1010
    1015
    1020

Thr Pro Gly Ser Thr Thr Arg Gln Gly Ser As
p Glu Gly Ser Val Glu
1025            1030
        1035
        1040

Asp Met Ile Gly Asp Thr Pro Arg Gln Gly Se
r Val Glu Gly Gly Gly
        1045
        1050
        1055
```

```
Thr Ser Ser Arg Pro Val Gln Arg Arg Ser Al
a Thr Glu Gly Ser Ile
            1060
                 1065
                      1070

Thr Thr Ile Ser Glu Gln Ile Asp Arg
         1075
              1080

(2) INFORMATION FOR SEQ ID NO:19:

(i) SEQUENCE CHARACTERISTICS:
         (A) LENGTH: 20 base
pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc
= "DNA"

(xi) SEQUENCE DESCRIPTION: SEQ ID NO:19:

CCACCATAAA TAGCAACGTC

20

(2) INFORMATION FOR SEQ ID NO:20:

(i) SEQUENCE CHARACTERISTICS:
         (A) LENGTH: 20 base
pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc
= "DNA"

(xi) SEQUENCE DESCRIPTION: SEQ ID NO:20:

GGACTCTAAA TTCTGGATGC

20

(2) INFORMATION FOR SEQ ID NO:21:

(i) SEQUENCE CHARACTERISTICS:
         (A) LENGTH: 368 base
pairs
         (B) TYPE: nucleic acid
         (C) STRANDEDNESS: single
         (D) TOPOLOGY: Not Relev
ant (ii) MOLECULE TYPE: other nucleic acid
         (A) DESCRIPTION: /desc
= "DNA"

(xi) SEQUENCE DESCRIPTION: SEQ ID NO:21:

CACGAGATGA GGACGCCATT GAATGGGATT ATTGGTATGA CTCAGTTGTC GC
TTGATACA      60

GAGTTGACAC AGTACCAACG AGAGATGTTG TCGATTGTGC ATAACTTGGC AA
ATTCCTTG     120

TTGACCATTA TAGACGATAT ATTGGATATT TCTAAGATTG AGGCGAATAG AA
TGACGGTG     180

GAACAGATTG ATTTTTCATT AAGAGGGACA GTGTTTGGTG CATTGAAAAC GT
TAGCCGTC     240
```

```
AAAGCTATTG AAAAAAACCT AGACTTGACC TATCAATGTG ATTCATCGTT TC
CAGATAAT       300

CTTATTGGAG ATAGTTTTAG ATTACGACAA GTTATTCTTA ACTTGGCTGG TA
ATGCCCTC       360

AAGTTCAC
              368
```

(2) INFORMATION FOR SEQ ID NO:22:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
His Glu Met Arg Thr Pro Leu Asn Gly Ile Ile Gly Met Thr Gln Leu
1               5                  10                  15

Ser Leu Asp Thr Glu Leu Thr Gln Tyr Gln Arg Glu Met Leu Ser Ile
            20                  25                  30

Val His Asn Leu Ala Asn Ser Leu Leu Thr Ile Ile Asp Asp Ile Leu
        35                  40                  45

Asp Ile Ser Lys Ile Glu Ala Asn Arg Met Thr Val Glu Gln Ile Asp
    50                  55                  60

Phe Ser Leu Arg Gly Thr Val Phe Gly Ala Leu Lys Thr Leu Ala Val
65                  70                  75                  80

Lys Ala Ile Glu Lys Asn Leu Asp Leu Thr Tyr Gln Cys Asp Ser Ser
                85                  90                  95

Phe Pro Asp Asn Leu Ile Gly Asp Ser Phe Arg Leu Arg Gln Val Ile
            100                 105                 110

Leu Asn Leu Ala Gly Asn Ala Leu Lys Phe
        115                 120
```

(2) INFORMATION FOR SEQ ID NO:23:

(i) SEQUENCE CHARACTERISTICS:
        (A) LENGTH: 144 base pairs
        (B) TYPE: nucleic acid (C) STRANDEDNESS: Not Relevant
        (D) TOPOLOGY: Not Relevant (ii) MOLECULE TYPE: other nucleic acid
        (A) DESCRIPTION: /desc = "DNA"

(xi) SEQUENCE DESCRIPTION: SEQ ID NO:23:

ATGACCATGA TTACGCCACT AGTCCGAGGC CTCGAGATCT ATCGATGCAT GCCATGGTAC    60

CCGGGAGCTC GAATTCGAAG CTTCTGCAGA CGCGTCGACG TCATATGGAT CCGATATCGC   120

CGTGGCGGCC GCTCTAGAAC TAGT                                         144

(2) INFORMATION FOR SEQ ID NO:24:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:24:

Arg Tyr Asp Leu Val Leu Met Asp Ile Val Met Pro Asn Leu Asp
 1               5                  10                  15

(2) INFORMATION FOR SEQ ID NO:25:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:25:

Lys Phe Asp Val Ile Leu Met Asp Val Gln Met Pro Ile Met Gly
 1               5                  10                  15

(2) INFORMATION FOR SEQ ID NO:26:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:26:

Asn Tyr Asn Met Phe Ile Met Asp Val Gln Me
t Pro Lys Val Asp
1               5
                10
                15

(2) INFORMATION FOR SEQ ID NO:27:

(i) SEQUENCE CHARACTERISTICS:
          (A) LENGTH: 15 amino
acids
          (B) TYPE: amino acid
          (C) STRANDEDNESS: Not R
elevant
          (D) TOPOLOGY: Not Relev
ant (ii) MOLECULE TYPE: peptide (xi) SEQUENCE DESCRIPTION: SEQ ID NO:27:

Pro Phe Asp Leu Ile Leu Met Asp Ile Gln Me
t Pro Asp Met Asp
1               5
                10
                15

(2) INFORMATION FOR SEQ ID NO:28:

(i) SEQUENCE CHARACTERISTICS:
          (A) LENGTH: 732 amino
acids
          (B) TYPE: amino acid
          (C) STRANDEDNESS: Not R
elevant
          (D) TOPOLOGY: Not Relev
ant (ii) MOLECULE TYPE: protein (xi) SEQUENCE DESCRIPTION: SEQ ID NO:28:

Met Thr Asp Gly Pro Thr Leu Ala Ala Ile Al
a Ala Leu Val Lys Ser
1               5
                10
                15

Leu Ala Val Asp Pro Ala Thr Thr Gln Thr Se
r Gly Leu Arg Pro Ser
          20
          25
          30

Thr His Val Arg Leu Pro Gly Pro Tyr Thr Ar
g Glu Lys Gly Asp Val
          35
          40
          45

Val Arg Ile Glu Gln Leu Glu Thr Ala Ala Il
e Ala Ala Ser Pro Pro
     50
     55
     60

Ala Met Pro Asp Thr Pro Asn Ala Pro Thr As
p Ala Leu Phe Ser Asn
65
70
75
80

Gly Thr Leu Ser Pro Ser Ser Glu Thr Pro As
p Ala Arg Tyr Phe Ile
          85
          90

```
                    95
Asp Glu Ala Leu Glu Gly Leu Arg Glu His Va
l Asp Asp Gln Ser Lys
        100
            105
                110

Leu Leu Asp Ser Gln Arg Gln Glu Leu Ala Gl
y Val Asn Ala Gln Leu
        115
            120
                125

Ile Glu Gln Lys Gln Leu Gln Glu Lys Ala Le
u Ala Ile Leu Glu Arg
        130
            135
                140

Glu Leu Trp Lys His Gln Lys Ala Asn Glu Al
a Phe Gln Lys Ala Leu
145                 1
50          1
55      1
60

Arg Glu Ile Gly Glu Ile Val Thr Ala Val Al
a Arg Gly Asp Leu Ser
            165
                170
                    175

Lys Lys Val Arg Met Asn Ser Val Glu Met As
p Pro Ile Asn Thr Met
        180
            185
                190

Met Asp Gln Leu Gln Val Phe Ser Ser Glu Va
l Ser Arg Val Ala Arg
        195
            200
                205

Glu Val Gly Thr Glu Gly Ile Leu Gly Gly Gl
n Ala Gln Ile Glu Gly
    210
        215
            220

Val Asp Gly Thr Trp Lys Glu Leu Thr Asp As
n Thr Asp Gln Val Arg
225                 2
30          2
35      2
40

Glu Ile Ala Ser Val Thr Thr Ala Val Ala Hi
s Gly Asp Leu Thr Lys
            245
                250
                    255

Lys Ile Glu Arg Pro Ala Lys Gly Glu Ile Le
u Gln Leu Gln Gln Thr
            260
                265
                    270

Ile Asn Thr Met Val Asp Gln Leu Arg Thr Al
a Arg Asp Val Gly Thr
        275
            280
                285

Glu Gly Ile Leu Gly Gly Gln Ala Asp Val Gl
u Gly Val Gln Gly Met
    290
        295
```

-continued

```
              300
Trp Asn Glu Leu Thr Val Asn Val Asn Ala Me
t Ala Asn Asn Leu Thr
305                 3
10                    3
15                      3
20

Thr Gln Val Arg Asp Ile Ile Lys Val Leu Th
r Gln Lys Val Gln Ala
            325
                330
                    335

Glu Cys Arg Gly Glu Ile Phe Glu Leu Lys Ly
s Thr Ile Asn Ser Met
            340
                345
                    350

Val Asp Gln Leu Gln Gln Phe Ala Arg Glu Va
l Thr Lys Ile Ala Arg
        355
            360
                365

Glu Val Gly Thr Glu Gly Arg Leu Val Gln Gl
y Thr Trp Arg Asp Leu
    370
        375
            380

Thr Glu Asn Val Asn Gly Met Ala Met Asn Le
u Thr Thr Gln Val Arg
385                 3
90                    3
95                      4
00

Glu Ile Ala Lys Val Thr Thr Ala Val Ala Ly
s Gly Asp Leu Thr Lys
                405
                    410
                        415

Lys Ile Gly Val Glu Val Gln Ile Glu Ala Ar
g Arg Met Val Ile Glu
            420
                425
                    430

Glu Ile Pro Tyr Thr Leu Arg Gly Thr Val Ph
e Asn Ala Leu Lys Thr
        435
            440
                445

Leu Ala Val Lys Ala Asn Glu Lys Phe Leu As
p Leu Thr Tyr Arg Val
    450
        455
            460

Asp His Ser Val Phe Arg Leu Arg Gln Ile Il
e Leu Asn Leu Val Gly
465                 4
70                    4
75                      4
80

Asn Ala Ile Lys Phe Thr Glu His Gly Glu Va
l Ser Leu Thr Ile Gln
                485
                    490
                        495

Lys Ala Ser Ser Val Gln Cys Ser Thr Glu Gl
u Tyr Ala Ile Glu Phe
            500
```

-continued

```
              505
              510

Val Val Ser Asp Thr Gly Ile Gly Ile Pro Al
a Asp Lys Leu Asp Leu
        515
          520
            525

Ile Phe Asp Thr Phe Gln Gln Ala Asp Gly Se
r Met Thr Arg Lys Phe
    530
      535
        540

Gly Gly Thr Gly Leu Gly Leu Leu Met Gly Gl
y Asp Val Trp Val Lys
545              5
50                5
55                 5
60

Ser Glu Tyr Gly Lys Gly Ser Lys Phe Phe Ph
e Thr Cys Val Val Arg
              565
                570
                  575

Leu Ala Asn Asp Asp Ile Ser Leu Ile Ala Ly
s Gln Leu Asn Pro Tyr
          580
            585
              590

Lys Ser His Gln Val Leu His Gly Pro Glu Il
e Ala Lys Met Leu His
        595
          600
            605

Gly Leu Gly Leu Val Pro Ile Val Val Asp Se
r Glu Arg Asn Pro Ala
      610
        615
          620

Leu Glu Lys Ala Arg Ala Ala Gly Gln Ala Pr
o Tyr Asp Val Ile Ile
625                6
30                  6
35                    6
40

Val Asp Ser Ile Ser Val Asp Asp Phe Lys Ty
r Leu Pro Ile Val Leu
              645
                650
                  655

Leu Ala Pro Val Val His Val Ser Leu Lys Se
r Cys Leu Asp Leu Gly
          660
            665
              670

Ile Thr Ser Tyr Met Thr Thr Pro Cys Gln Le
u Ile Asp Leu Gly Asn
        675
          680
            685

Gly Met Thr Pro Ser Leu Ala Asp Asn Thr Ly
s Ser Phe Glu Ile Leu
    690
      695
        700

Leu Ala Glu Asp Asn Thr Val Asn Gln Arg Le
u Ala Val Lys Ile Leu
705                7
```

```
              10              7
              15              7
              20

Glu Lys Tyr His His Val Val Thr Val Val Gl
y Asn
                725
                730

(2) INFORMATION FOR SEQ ID NO:29:

(i) SEQUENCE CHARACTERISTICS:
          (A) LENGTH: 335 amino
acids
          (B) TYPE: amino acid
          (C) STRANDEDNESS: Not R
elevant
          (D) TOPOLOGY: Not Relev
ant (ii) MOLECULE TYPE: protein (xi) SEQUENCE DESCRIPTION: SEQ ID NO:29:

Met Thr Asn Tyr Ser Leu Arg Ala Arg Met Me
t Ile Leu Ile Leu Ala
1               5
                10
                15

Pro Thr Val Leu Ile Gly Leu Leu Leu Ser Il
e Phe Phe Val Leu Glu
             20
             25
             30

Ala Gly Lys Leu Ile Leu Glu Ser Ile Pro Ph
e Pro Leu Arg Ser Thr
          35
          40
          45

Leu Asp Glu Val Val Thr Leu Leu Ala His Se
r Ser His Asp Lys Gly
       50
       55
       60

Leu Glu Leu Thr Leu Asn Ile Lys Ser Asp Va
l Leu Arg Leu Gln Gln
65
70
75
80

Ile Ile Thr Asn Leu Val Gly Asn Ala Ile Ly
s Phe Thr Glu Asn Gly
             85
             90
             95

Asn Ile Asp Ile Leu Val Glu Lys Arg Ala Le
u Ser Asn Thr Lys Val
          100
          105
          110

Gln Ile Glu Val Gln Ile Arg Asp Thr Gly Il
e Gly Ile Pro Glu Arg
       115
       120
       125

Asp Gln Ser Arg Leu Phe Gln Ala Phe Arg Gl
n Ala Asp Ala Ser Ile
    130
    135
    140
```

```
Ser Arg Arg His Gly Gly Thr Gly Leu Gly Leu Glu Met Gly Gly Asp
145                 150                 155                 160

Ile Ser Phe His Ser Gln Pro Asn Arg Gly Ser Thr Phe Trp Phe His
            165                 170                 175

Ile Asn Leu Asp Leu Asn Pro Asn Ile Ile Ile Glu Gly Pro Ser Thr
        180                 185                 190

Gln Cys Leu Ala Gly Lys Arg Leu Ala Ala Gln Cys Thr Leu Asp Ile
    195                 200                 205

Leu Ser Glu Thr Pro Leu Glu Val Val Tyr Ser Pro Thr Phe Ser Ala
210                 215                 220

Leu Pro Pro Ala His Tyr Asp Met Met Leu Leu Gly Ile Ala Val Thr
225                 230                 235                 240

Phe Arg Glu Pro Leu Lys Ala Val Ser Met Thr Asp Phe Leu Met Leu
            245                 250                 255

Ala Leu Pro Cys His Ala Gln Val Asn Ala Glu Lys Leu Lys Gln Asp
        260                 265                 270

Gly Ile Gly Ala Cys Leu Leu Lys Pro Leu Thr Pro Thr Arg Leu Leu
    275                 280                 285

Pro Ala Leu Thr Leu Leu Pro Val Thr Asp Glu Ser Lys Leu Ala Met
290                 295                 300

Thr Val Met Ala Val Asp Asp Asn Pro Ala Asn Leu Lys Leu Ile Gly
305                 310                 315                 320

Ala Leu Leu Glu Asp Met Val Gln His Val Glu Leu Cys Asp Ser
            325                 330                 335
```

(2) INFORMATION FOR SEQ ID NO:30:

(i) SEQUENCE CHARACTERISTICS:
        (A) LENGTH: 354 amino acids
          (B) TYPE: amino acid
          (C) STRANDEDNESS: Not Relevant
          (D) TOPOLOGY: Not Relevant (ii) MOLECULE TYPE: protein (xi) SEQUENCE DESCRIPTION: SEQ ID NO:30:

Asn Arg Arg Thr Asp Thr Gly Cys Trp Arg Lys Ser Val Leu Asn Lys
1               5                  10                  15

Leu Gly Ile Lys Gly Arg Val Leu Leu Leu Thr Ile Leu Pro Ala Ser
            20                  25                  30

Leu Met Ala Ala Val Leu Gly Gly Tyr Phe Ile Glu Ala Gly Lys Leu
        35                  40                  45

Val Leu Asp Asn Ile Pro Phe Asn Leu Arg Asp Leu Leu Gln Asp Thr
    50                  55                  60

Leu Thr Ile Leu Ala Pro Ala Ala His Ala Lys Gln Leu Glu Leu Val
65                  70                  75                  80

Ser Leu Val Tyr Arg Asp Thr Leu Arg Leu Arg Gln Ile Leu Thr Asn
                85                  90                  95

Leu Val Ser Asn Ala Ile Lys Phe Thr Arg Gln Gly Thr Ile Val Ala
            100                 105                 110

Arg Ala Met Leu Glu Asp Glu Thr Glu Glu His Ala Gln Leu Arg Ile
        115                 120                 125

Ser Val Gln Asp Thr Gly Ile Gly Leu Ser Ser Gln Asp Val Arg Ala
    130                 135                 140

Leu Phe Gln Ala Phe Ser Gln Ala Asp Asn Ser Ile Ser Arg Gln Pro
145                 150                 155                 160

Gly Gly Thr Gly Leu Gly Leu Gln Met Gly Gly Glu Ile Gly Val Asp
                165                 170                 175

Ser Thr Pro Gly Glu Gly Ser Glu Phe Trp Il

```
e Ser Leu Asn Leu Pro
        180
          185
            190

Lys Ala Arg Glu Asp Arg Glu Glu Thr Ala As
n Gln Ala Leu Glu Gly
     195
       200
         205

Leu Arg Ala Ala Val Leu Ala Leu Glu His Gl
n Leu Glu Asp Cys Gly
    210
      215
        220

Leu Gln Thr Val Val Phe Thr Asn Leu Glu As
n Leu Leu Asn Gly Val
225                   2
30                      2
35                        2
40

Thr Ala Ala His Glu Thr Pro Gln Ala Ile As
p Leu Val Val Leu Gly
          245
            250
              255

Val Thr Ala Leu His Ile Trp Asp Leu Glu As
n Leu Asn Cys Lys Val
         260
           265
             270

Met Val Leu Cys Pro Thr Thr Glu His Ala Le
u Phe Gln Met Ser Val
        275
          280
            285

His Asp Val Tyr Thr Gln Leu Gln Ala Lys Pr
o Ala Cys Asn Arg Lys
       290
         295
           300

Leu Gln Lys Arg Ala Val Arg Thr Asp Val Al
a Leu Pro Leu Ser Ser
305                   3
10                      3
15                        3
20

Arg Ala Pro Arg Val Leu Cys Val Asp Asp As
n Pro Ala Asn Leu Leu
           325
             330
               335

Leu Val Gln Thr Leu Leu Glu Asp Met Gly Al
a Glu Val Val Ala Val
          340
            345
              350

Asp Gly (2) INFORMATION FOR SEQ ID NO:31:

(i) SEQUENCE CHARACTERISTICS:
        (A) LENGTH: 351 amino
acids
        (B) TYPE: amino acid
        (C) STRANDEDNESS: Not R
elevant
        (D) TOPOLOGY: Not Relev
ant
```

(ii) MOLECULE TYPE: protein (xi) SEQUENCE DESCRIPTION: SEQ ID NO:31:

```
Met Leu Lys Lys Leu Gly Ile Lys Gly Arg Val Leu Leu Leu Thr Leu
 1               5                  10                  15

Leu Pro Thr Ser Leu Met Ala Leu Val Leu Gly Gly Tyr Phe Ile Glu
             20                  25                  30

Ala Gly Lys Leu Val Leu Asp Ser Ile Pro Phe Asn Leu Arg Asp Leu
         35                  40                  45

Leu Gln Asp Thr Leu Thr Ile Leu Ala Pro Ala Ala His Ala Lys Gln
     50                  55                  60

Leu Glu Leu Val Ser Leu Val Tyr Arg Asp Thr Pro Leu Ser Leu Val
 65                  70                  75                  80

Gly Asp Pro Leu Arg Leu Lys Gln Ile Leu Thr Asn Leu Val Ser Asn
                 85                  90                  95

Ala Ile Lys Phe Thr Arg Glu Gly Thr Ile Val Ala Arg Ala Met Leu
            100                 105                 110

Glu Glu Glu His Glu Asp Ser Val Gln Leu Arg Ile Ser Ile Gln Asp
        115                 120                 125

Thr Gly Ile Gly Leu Ser Asn Gln Asp Val Arg Ala Leu Phe Gln Ala
    130                 135                 140

Phe Ser Gln Ala Asp Asn Ser Leu Ser Arg Gln Pro Gly Gly Thr Gly
145                 150                 155                 160

Leu Gly Leu Gln Met Gly Gly Glu Ile Gly Val Asp Ser Thr Pro Gly
                165                 170                 175

Glu Gly Ser Glu Phe Trp Ile Ser Leu Asn Leu Pro Lys Thr Arg Asp
            180                 185                 190

Asp Ala Glu Asp Leu Pro Gly Pro Pro Leu Le
```

```
u Gly Arg Arg Val Ala
        195
    200
        205

Val Leu Ala Leu Gln His Gln Leu Glu Asp Cy
s Gly Leu Glu Val Thr
        210
    215
        220

Pro Phe Asn Thr Leu Glu Ala Leu Thr Asn Gl
y Ile Thr Gly Val His
225                 2
30              2
35          2
40

Gln Ser Glu Gln Ala Ile Asp Leu Ala Val Le
u Gly Ile Thr Thr Asn
            245
        250
            255

Asp His Ile Trp Asp Leu Glu His Leu Gly Cy
s Lys Val Leu Val Leu
            260
        265
            270

Cys Pro Thr Thr Glu Gln Thr Leu Phe His Le
u Ser Val Pro Asn Pro
        275
    280
        285

His Ser Gln Leu Gln Ala Lys Pro Ala Cys Th
r Arg Lys Leu Arg Arg
        290
    295
        300

Arg Arg Ala Arg Ser Glu Pro Glu Glu Thr Le
u Ser Ser Arg Ala Pro
305                 3
10              3
15          3
20

Arg Val Leu Cys Val Asp Asp Asn Pro Ala As
n Leu Leu Leu Ile Gln
            325
        330
            335

Thr Leu Leu Glu Asp Met Gly Ala Lys Val Le
u Ala Val Asp Asn
            340
        345
            350

(2) INFORMATION FOR SEQ ID NO:32:

(i) SEQUENCE CHARACTERISTICS:
        (A) LENGTH: 751 amino
acids
        (B) TYPE: amino acid
        (C) STRANDEDNESS: Not R
elevant
        (D) TOPOLOGY: Not Relev
ant (ii) MOLECULE TYPE: protein (xi) SEQUENCE DESCRIPTION: SEQ ID NO:32:

Met Arg Phe Gly Leu Pro Ser Lys Leu Glu Le
u Thr Pro Pro Phe Arg
1               5
```

```
            10
            15

Ile Gly Ile Arg Thr Gln Leu Thr Ala Leu Va
l Ser Ile Val Ala Leu
            20
            25
            30

Gly Ser Leu Ile Ile Leu Ala Val Thr Thr Gl
y Val Tyr Phe Thr Asp
            35
            40
            45

Arg Leu Tyr Ile Ala Ala Gln Leu Lys Ser Se
r Gln Ile Asp Gln Thr
       50
       55
       60

Leu Asn Tyr Leu Tyr Tyr Gln Ala Tyr Tyr Le
u Ala Ser Arg Asp Ala
65
70
75
80

Leu Gln Ser Ser Leu Thr Ser Tyr Val Ala Gl
y Asn Lys Ser Ser Val
            85
            90
            95

Ile Gln Lys Phe Leu Ser Ser Ser Asn Leu Ph
e Tyr Val Ala Lys Val
            100
            105
            110

Tyr Asp Ser Ser Phe Asn Ala Val Leu Asn Al
a Thr Asn Asn Gly Thr
       115
       120
       125

Gly Asp Leu Ile Pro Glu Asp Val Leu Asp Se
r Leu Phe Pro Ser Ser
      130
      135
      140

Leu Glu Thr Ile Gly Ile Leu Thr Asp Pro Va
l Leu Asn Ser Thr Asp
145                         1
50                          1
55                          1
60

Tyr Leu Met Ser Met Ser Leu Pro Ile Phe Al
a Asn Pro Ser Ile Ile
            165
            170
            175

Leu Thr Asp Ser Arg Val Tyr Gly Tyr Ile Th
r Ile Ser Val Phe Asn
            180
            185
            190

Asp Thr Thr Ala Leu Glu His Ser Thr Ile Al
a Ile Ile Ser Ala Val
       195
       200
       205

Tyr Asn Ser Gln Gly Lys Ala Ser Gly Tyr Hi
s Phe Val Phe Pro Pro
    210
```

-continued

```
          215
          220

Tyr Gly Ser Arg Ser Asp Leu Pro Gln Lys Va
l Ile Ser Ser Ala Phe
225                 2
30                  2
35                  2
40

Arg Asn Gly Lys Gly Gly Ser Leu Lys Gln Th
r Asn Ile Leu Ser Thr
              245
              250
              255

Arg Asn Thr Ala Leu Gly Tyr Ser Pro Cys Se
r Phe Asn Leu Val Asn
              260
              265
              270

Trp Val Ala Ile Val Ser Gln Pro Glu Ser Le
u Ala Lys Ile Ile Thr
              275
              280
              285

Gly Thr Val Ile Ala Ile Gly Val Phe Val Il
e Leu Leu Thr Leu Pro
          290
          295
          300

Leu Ala His Trp Ala Val Gln Pro Ile Val Ar
g Leu Gln Lys Ala Thr
305                 3
10                  3
15                  3
20

Glu Leu Ile Thr Glu Gly Arg Gly Leu Ser Ar
g Ala Ser Ser Phe Lys
              325
              330
              335

Arg Gly Phe Ser Ser Gly Phe Ala Val Pro Se
r Ser Leu Leu Gln Phe
              340
              345
              350

Asn Thr Ala Glu Ala Gly Ser Thr Thr Ser Va
l Ser Gly His Gly Gly
              355
              360
              365

Ser Gly His Gly Ser Gly Ala Ala Asn Val Le
u Gln Arg Thr Lys Leu
              370
              375
              380

Glu Lys Arg Asp Phe Cys Ile Thr Asp Val Al
a Leu Gln Ile Lys Ser
385                 3
90                  3
95                  4
00

Ile Phe Gly Lys Val Ala Lys Asp Gln Arg Va
l Arg Leu Ser Ile Ser
              405
              410
              415

Leu Phe Pro Asn Leu Ile Arg Asn Arg Ile Il
e Gln Ile Val Met Asn
```

```
                    420
                    425
                    430

Leu Val Ser Asn Ala Leu Lys Phe Thr Pro Va
l Asp Gly Thr Val Asp
        435
            440
                445

Val Arg Met Lys Leu Leu Gly Glu Tyr Asp Ly
s Glu Leu Ser Glu Lys
    450
        455
            460

Lys Gln Tyr Lys Glu Val Thr Glu Asn Leu Gl
u Thr Thr Asp Lys Tyr
465                 4
70              4
75          4
80

Asp Leu Pro Thr Leu Ser Asn His Arg Lys Se
r Val Asp Leu Glu Ser
            485
                490
                    495

Ser Ala Thr Ser Leu Gly Ser Asn Arg Asp Th
r Ser Thr Ile Gln Glu
            500
                505
                    510

Glu Ile Thr Lys Arg Tyr Lys Lys Val Asn As
p Arg Glu Lys Ala Ser
        515
            520
                525

Asn Asp Asp Val Ser Ser Ile Val Ser Thr Th
r Thr Ser Ser Tyr Asp
    530
        535
            540

Asn Ala Ile Phe Asn Ser Gln Phe Asn Lys Al
a Pro Gly Ser Asp Asp
545                 5
50              5
55          5
60

Glu Glu Gly Pro Lys Thr Trp Val Ile Ser Il
e Glu Val Glu Asp Thr
                565
                    570
                        575

Gly Pro Gly Ile Asp Pro Ser Leu Gln Glu Se
r Val Phe His Pro Phe
            580
                585
                    590

Val Gln Gly Asp Gln Thr Leu Ser Arg Gln Ty
r Gly Gly Thr Gly Leu
        595
            600
                605

Gly Leu Ser Met Met His Gly Thr Met Lys Le
u Glu Ser Lys Val Gly
    610
        615
            620

Val Gly Ser Lys Phe Thr Phe Thr Leu Pro Le
u Asn Gln Thr Lys Glu
```

```
            625           6
30                        6
35                        6
40

Ile Ser Phe Ala Asp Met Glu Phe Pro Phe Gl
u Asp Glu Phe Asn Pro
            645
                650
                    655

Glu Ser Ser Val Ala Lys Ser Ile Lys Ser Ar
g Gln Ser Thr Ser Ser
        660
            665
                670

Val Ala Thr Pro Ala Thr Asn Arg Ser Ser Le
u Thr Asn Asp Val Leu
        675
            680
                685

Pro Glu Val Arg Ser Lys Gly Lys His Glu Th
r Lys Asp Val Gly Asn
    690
        695
            700

Asp Asn Gly Gly Leu Glu Gln Leu Gln Glu Ly
s Asn Ile Lys Pro Ser
705                       7
10                        7
15                        7
20

Ile Cys Leu Thr Gly Ala Glu Val Asn Glu Gl
n Asn Ser Leu Ser Ser
            725
                730
                    735

Lys His Arg Ser Arg His Glu Gly Leu Gly Se
r Val Asn Leu Asp
            740
                745
                    750

(2) INFORMATION FOR SEQ ID NO:33:

(i) SEQUENCE CHARACTERISTICS:
        (A) LENGTH: 1117 amino
acids
        (B) TYPE: amino acid
        (C) STRANDEDNESS: Not R
elevant
        (D) TOPOLOGY: Not Relev
ant (ii) MOLECULE TYPE: protein (xi) SEQUENCE DESCRIPTION: SEQ ID NO:33:

Asp Leu Leu Cys Trp Ser Cys Val Val Ala Il
e Tyr Lys Ala Pro Pro
1           5
                10
                    15

Tyr Ile Asn Lys Lys Phe Phe Leu Ser Val Va
l Tyr Leu Glu Phe Leu
            20
                25
                    30

Pro Leu Ser Pro Met Asn Pro Thr Lys Lys Pr
o Arg Leu Ser Pro Met
        35
            40
```

45

Gln Pro Ser Val Phe Glu Ile Leu Asn Asp Pr
o Glu Leu Tyr Ser Gln
     50
        55
            60

His Cys His Ser Leu Arg Glu Thr Leu Leu As
p His Phe Asn His Gln
65
    70
        75
            80

Ala Thr Leu Ile Asp Thr Tyr Glu His Glu Le
u Glu Lys Ser Lys Asn
                85
                    90
                        95

Ala Asn Lys Ala Phe Gln Gln Ala Leu Ser Gl
u Ile Gly Thr Val Val
            100
                105
                    110

Ile Ser Val Ala Met Gly Asp Leu Ser Lys Ly
s Val Glu Ile His Thr
        115
            120
                125

Val Glu Asn Asp Pro Glu Ile Leu Lys Val Ly
s Ile Thr Ile Asn Thr
    130
        135
            140

Met Met Asp Gln Leu Gln Thr Phe Ala Asn Gl
u Val Thr Lys Val Ala
145                 1
50                  1
55                  1
60

Thr Glu Val Ala Asn Gly Glu Leu Gly Gly Gl
n Ala Lys Asn Asp Gly
                165
                    170
                        175

Ser Val Gly Ile Trp Arg Ser Leu Thr Asp As
n Val Asn Ile Met Ala
            180
                185
                    190

Leu Asn Leu Thr Asn Gln Val Arg Glu Ile Al
a Asp Val Thr Arg Ala
        195
            200
                205

Val Ala Lys Gly Asp Leu Ser Arg Lys Ile As
n Val His Ala Gln Gly
    210
        215
            220

Glu Ile Leu Gln Leu Gln Arg Thr Ile Asn Th
r Met Val Asp Gln Leu
225                 2
30                  2
35                  2
40

Arg Thr Phe Ala Phe Glu Val Ser Lys Val Al
a Arg Asp Val Gly Val
                245

-continued

```
                250
                   255

Leu Gly Ile Leu Gly Gly Gln Ala Leu Ile Gl
u Asn Val Glu Gly Ile
            260
               265
                   270

Trp Glu Glu Leu Thr Asp Asn Val Asn Ala Me
t Ala Leu Asn Leu Thr
        275
            280
                285

Thr Gln Val Arg Asn Ile Ala Asn Val Thr Th
r Ala Val Ala Lys Gly
    290
        295
            300

Asp Leu Ser Lys Lys Val Thr Ala Asp Cys Ly
s Gly Glu Ile Leu Asp
305                 3
10                      3
15                          3
20

Leu Lys Leu Thr Ile Asn Gln Met Val Asp Ar
g Leu Gln Asn Phe Ala
                325
                    330
                        335

Leu Ala Val Thr Thr Leu Ser Arg Glu Val Gl
y Thr Leu Gly Ile Leu
            340
                345
                    350

Gly Gly Gln Ala Asn Val Gln Asp Val Glu Gl
y Ala Trp Lys Gln Val
        355
            360
                365

Thr Glu Asn Val Asn Leu Met Ala Thr Asn Le
u Thr Asn Gln Val Arg
    370
        375
            380

Ser Ile Ala Thr Val Thr Thr Ala Val Ala Hi
s Gly Asp Leu Ser Gln
385                 3
90                      3
95                          4
00

Lys Ile Asp Val His Ala Gln Gly Glu Ile Le
u Gln Leu Lys Asn Thr
                405
                    410
                        415

Ile Asn Lys Met Val Asp Ser Leu Gln Leu Ph
e Ala Ser Glu Val Ser
            420
                425
                    430

Lys Val Ala Gln Asp Val Gly Ile Asn Gly Ly
s Leu Gly Ile Gln Ala
        435
            440
                445

Gln Val Ser Asp Val Asp Gly Leu Trp Lys Gl
u Ile Thr Ser Asn Val
    450
```

Asn Thr Met Ala Ser Asn Leu Thr Ser Gln Val Arg Ala Phe Ala Gln
465 470 475 480

Ile Thr Ala Ala Ala Thr Asp Gly Asp Phe Thr Arg Phe Ile Thr Val
485 490 495

Glu Ala Leu Gly Glu Met Asp Ala Leu Lys Thr Lys Ile Asn Gln Met
500 505 510

Val Phe Asn Leu Arg Glu Ser Leu Gln Arg Asn Thr Ala Ala Arg Glu
515 520 525

Ala Ala Glu Leu Ala Asn Ser Ala Lys Ser Glu Phe Leu Ala Asn Met
530 535 540

Ser His Glu Ile Arg Thr Pro Leu Asn Gly Ile Ile Gly Met Thr Gln
545 550 555 560

Leu Ser Leu Asp Thr Glu Leu Thr Gln Tyr Gln Arg Glu Met Leu Ser
565 570 575

Ile Val His Asn Leu Ala Asn Ser Leu Leu Thr Ile Ile Asp Asp Ile
580 585 590

Leu Asp Ile Ser Lys Ile Glu Ala Asn Arg Met Thr Val Glu Gln Ile
595 600 605

Asp Phe Ser Leu Arg Gly Thr Val Phe Gly Ala Leu Lys Thr Leu Ala
610 615 620

Val Lys Ala Ile Glu Lys Asn Leu Asp Leu Thr Tyr Gln Cys Asp Ser
625 630 635 640

Ser Phe Pro Asp Asn Leu Ile Gly Asp Ser Phe Arg Leu Arg Gln Val
645 650 655

Ile Leu Asn Leu Ala Gly Asn Ala Ile Lys Phe Thr Lys Glu Gly Lys

```
                         660
                         665
                         670
Val Ser Val Ser Val Lys Lys Ser Asp Lys Me
t Val Leu Asp Ser Lys
        675
            680
                685
Leu Leu Leu Glu Val Cys Val Ser Asp Thr Gl
y Ile Gly Ile Glu Lys
        690
            695
                700
Asp Lys Leu Gly Leu Ile Phe Asp Thr Phe Cy
s Gln Ala Asp Gly Ser
705             7
10                  7
15                      7
20
Thr Thr Arg Lys Phe Gly Gly Thr Gly Leu Gl
y Leu Ser Ile Ser Lys
            725
                730
                    735
Gln Leu Ile His Leu Met Gly Gly Glu Ile Tr
p Val Thr Ser Glu Tyr
            740
                745
                    750
Gly Ser Gly Ser Asn Phe Tyr Phe Thr Val Cy
s Val Ser Pro Ser Asn
        755
            760
                765
Ile Arg Tyr Thr Arg Gln Thr Glu Gln Leu Le
u Pro Phe Ser Ser His
    770
        775
            780
Tyr Val Leu Phe Val Ser Thr Glu His Thr Gl
n Glu Glu Leu Asp Val
785             7
90                  7
95                      8
00
Leu Arg Asp Gly Ile Ile Glu Leu Gly Leu Il
e Pro Ile Ile Val Arg
                805
                    810
                        815
Asn Ile Glu Asp Ala Thr Leu Thr Glu Pro Va
l Lys Tyr Asp Ile Ile
            820
                825
                    830
Met Ile Asp Ser Ile Glu Ile Ala Lys Lys Le
u Arg Leu Leu Ser Glu
        835
            840
                845
Val Lys Tyr Ile Pro Leu Val Leu Val His Hi
s Ser Ile Pro Gln Leu
        850
            855
                860
Asn Met Arg Val Cys Ile Asp Leu Gly Ile Se
r Ser Tyr Ala Asn Thr
```

```
865                 8
70                  8
75                  8
80

Pro Cys Ser Ile Thr Asp Leu Ala Ser Al
e Ile Pro Ala Leu Glu
            885
                890
                    895

Ser Arg Ser Ile Ser Gln Asn Ser Asp Glu Se
r Val Arg Tyr Lys Ile
         900
             905
                 910

Leu Leu Ala Glu Asp Asn Leu Val Asn Gln Ly
s Leu Ala Val Arg Ile
         915
             920
                 925

Leu Glu Lys Gln Gly His Leu Val Glu Val Va
l Glu Asn Gly Leu Glu
       930
           935
               940

Ala Tyr Glu Ala Ile Lys Arg Asn Lys Tyr As
p Val Val Leu Met Asp
945                 9
50                  9
55                  9
60

Val Gln Met Pro Val Met Gly Gly Phe Glu Al
a Thr Glu Lys Ile Arg
              965
                  970
                      975

Gln Trp Glu Lys Lys Ser Asn Pro Ile Asp Se
r Leu Thr Phe Arg Thr
           980
               985
                   990

Pro Ile Ile Ala Leu Thr Ala His Ala Met Le
u Gly Asp Arg Glu Lys
         995
            1000
            1005

Ser Leu Ala Lys Gly Met Asp Asp Tyr Val Se
r Lys Pro Leu Lys Pro
      1010
         1015
       1020

Lys Leu Leu Met Gln Thr Ile Asn Lys Cys Il
e His Asn Ile Asn Gln
1025            1030
             1035
                1040

Leu Lys Glu Leu Ser Arg Asn Ser Arg Gly Se
r Asp Phe Ala Lys Lys
              1045
                 1050
                    1055

Met Thr Arg Asn Thr Pro Gly Ser Thr Thr Ar
g Gln Gly Ser Asp Glu
             1060
                1065
                   1070

Gly Ser Val Glu Asp Met Ile Gly Asp Thr Pr
o Arg Gln Gly Ser Val
```

```
          1075
          1080
          1085

Glu Gly Gly Gly Thr Ser Ser Arg Pro Val Gl
n Arg Arg Ser Ala Thr
     1090
       1095
      1100

Glu Gly Ser Ile Thr Thr Ile Ser Glu Gln Il
e Asp Arg
1105              1110
             1115

(2) INFORMATION FOR SEQ ID NO:34:

(i) SEQUENCE CHARACTERISTICS:
        (A) LENGTH: 1298 amino
acids
        (B) TYPE: amino acid
        (C) STRANDEDNESS: Not R
elevant
        (D) TOPOLOGY: Not Relev
ant (ii) MOLECULE TYPE: protein (xi) SEQUENCE DESCRIPTION: SEQ ID NO:34:

Met Thr Asp Gly Pro Thr Leu Ala Ala Ile Al
a Ala Leu Val Lys Ser
1               5
              10
              15

Leu Ala Val Asp Pro Ala Thr Thr Gln Thr Se
r Gly Leu Arg Pro Ser
           20
             25
             30

Thr His Val Arg Leu Pro Gly Pro Tyr Thr Ar
g Glu Lys Gly Asp Leu
         35
           40
           45

Glu Arg Glu Leu Ser Ala Leu Val Val Arg Il
e Glu Gln Leu Glu Thr
       50
         55
         60

Ala Ala Ile Ala Ala Ser Pro Pro Ala Met Pr
o Asp Thr Pro Asn Ala
65
70
75
80

Pro Thr Asp Ala Leu Phe Ser Asn Gly Thr Le
u Ser Pro Ser Ser Glu
             85
             90
             95

Thr Pro Asp Ala Arg Tyr Pro Ala Pro Leu Pr
o Arg Asn Gly Phe Ile
           100
           105
           110

Asp Glu Ala Leu Glu Gly Leu Arg Glu His Va
l Asp Asp Gln Ser Lys
         115
         120
         125
```

```
Leu Leu Asp Ser Gln Arg Gln Glu Leu Ala Gl
y Val Asn Ala Gln Leu
    130
      135
        140

Ile Glu Gln Lys Gln Leu Gln Glu Lys Ala Le
u Ala Ile Ile Glu Gln
145                     1
  50                      1
    55                      1
      60

Glu Arg Val Ala Thr Leu Glu Arg Glu Leu Tr
p Lys His Gln Lys Ala
      165
        170
          175

Asn Glu Ala Phe Gln Lys Ala Leu Arg Glu Il
e Gly Glu Ile Val Thr
        180
          185
            190

Ala Val Ala Arg Gly Asp Leu Ser Lys Lys Va
l Arg Met Asn Ser Val
      195
        200
          205

Glu Met Asp Pro Glu Ile Thr Thr Phe Lys Ar
g Thr Ile Asn Thr Met
    210
      215
        220

Met Asp Gln Leu Gln Val Phe Ser Ser Glu Va
l Ser Arg Val Ala Arg
225                     2
  30                      2
    35                      2
      40

Glu Val Gly Thr Glu Gly Ile Leu Gly Gly Gl
n Ala Gln Ile Glu Gly
            245
              250
                255

Val Asp Gly Thr Trp Lys Glu Leu Thr Asp As
n Val Asn Val Met Ala
          260
            265
              270

Gln Asn Leu Thr Asp Gln Val Arg Glu Ile Al
a Ser Val Thr Thr Ala
        275
          280
            285

Val Ala His Gly Asp Leu Thr Lys Lys Ile Gl
u Arg Pro Ala Lys Gly
      290
        295
          300

Glu Ile Leu Gln Leu Gln Gln Thr Ile Asn Th
r Met Val Asp Gln Leu
305                     3
  10                      3
    15                      3
      20

Arg Thr Phe Ala Ser Glu Val Thr Arg Val Al
a Arg Asp Val Gly Thr
              325
                330
                  335
```

Glu Gly Ile Leu Gly Gly Gln Ala Asp Val Glu Gly Val Gln Gly Met
                340             345             350

Trp Asn Glu Leu Thr Val Asn Val Asn Ala Met Ala Asn Asn Leu Thr
            355             360             365

Thr Gln Val Arg Asp Ile Ile Lys Val Thr Thr Ala Val Ala Lys Gly
        370             375             380

Asp Leu Thr Gln Lys Val Gln Ala Glu Cys Arg Gly Glu Ile Phe Glu
385             390             395             400

Leu Lys Lys Thr Ile Asn Ser Met Val Asp Gln Leu Gln Gln Phe Ala
                405             410             415

Arg Glu Val Thr Lys Ile Ala Arg Glu Val Gly Thr Glu Gly Arg Leu
            420             425             430

Gly Gly Gln Ala Thr Val His Asp Val Gln Gly Thr Trp Arg Asp Leu
        435             440             445

Thr Glu Asn Val Asn Gly Met Ala Met Asn Leu Thr Thr Gln Val Arg
    450             455             460

Glu Ile Ala Lys Val Thr Thr Ala Val Ala Lys Gly Asp Leu Thr Lys
465             470             475             480

Lys Ile Gly Val Glu Val Gln Gly Glu Ile Leu Asp Leu Lys Asn Thr
                485             490             495

Ile Asn Thr Met Val Asp Arg Leu Gly Thr Phe Ala Phe Glu Val Ser
            500             505             510

Lys Val Ala Arg Glu Val Gly Thr Asp Gly Thr Leu Gly Gly Gln Ala
        515             520             525

Gln Val Asp Asn Val Glu Gly Lys Trp Lys Asp Leu Thr Glu Asn Val
    530             535             540

-continued

Asn Thr Met Ala Ser Asn Leu Thr Ser Gln Val Arg Gly Ile Ser Thr
545                 550                 555                 560

Val Thr Gln Ala Ile Ala Asn Gly Asp Met Ser Arg Lys Ile Glu Val
            565                 570                 575

Glu Ala Lys Gly Glu Ile Leu Ile Leu Lys Glu Thr Ile Asn Asn Met
        580                 585                 590

Val Asp Arg Leu Ser Ile Phe Cys Asn Glu Val Gln Arg Val Ala Lys
    595                 600                 605

Asp Val Gly Val Asp Gly Ile Met Gly Gly Gln Ala Asp Val Ala Gly
610                 615                 620

Leu Lys Gly Arg Trp Lys Glu Ile Thr Thr Asp Val Asn Thr Met Ala
625                 630                 635                 640

Asn Asn Leu Thr Ala Gln Val Arg Ala Phe Gly Asp Ile Thr Asn Ala
            645                 650                 655

Ala Thr Asp Gly Asp Phe Thr Lys Leu Val Glu Val Glu Ala Ser Gly
        660                 665                 670

Glu Met Asp Glu Leu Lys Lys Lys Ile Asn Gln Met Val Tyr Asn Leu
    675                 680                 685

Arg Asp Ser Ile Gln Arg Asn Thr Gln Ala Arg Glu Ala Ala Glu Leu
690                 695                 700

Ala Asn Lys Thr Lys Ser Glu Phe Leu Ala Asn Met Ser His Glu Ile
705                 710                 715                 720

Arg Thr Pro Met Asn Gly Ile Ile Gly Met Thr Gln Leu Thr Leu Asp
            725                 730                 735

Thr Asp Leu Thr Gln Tyr Gln Arg Glu Met Leu Asn Ile Val Asn Ser
        740                 745

```
                750
Leu Ala Asn Ser Leu Leu Thr Ile Ile Asp As
p Ile Leu Asp Leu Ser
        755
            760
                765

Lys Ile Glu Ala Arg Arg Met Val Ile Glu Gl
u Ile Pro Tyr Thr Leu
    770
        775
            780

Arg Gly Thr Val Phe Asn Ala Leu Lys Thr Le
u Ala Val Lys Ala Asn
785             7
90                  7
95                      8
00

Glu Lys Phe Leu Asp Leu Thr Tyr Arg Val As
p His Ser Val Pro Asp
        805
            810
                815

His Val Val Gly Asp Ser Phe Arg Leu Arg Gl
n Ile Ile Leu Asn Leu
            820
                825
                    830

Val Gly Asn Ala Ile Lys Phe Thr Glu His Gl
y Glu Val Ser Leu Thr
        835
            840
                845

Ile Gln Lys Ala Ser Ser Val Gln Cys Ser Th
r Glu Glu Tyr Ala Ile
    850
        855
            860

Glu Phe Val Val Ser Asp Thr Gly Ile Gly Il
e Pro Ala Asp Lys Leu
865             8
70                  8
75                      8
80

Asp Leu Ile Phe Asp Thr Phe Gln Gln Ala As
p Gly Ser Met Thr Arg
            885
                890
                    895

Lys Phe Gly Gly Thr Gly Leu Gly Leu Ser Il
e Ser Lys Arg Leu Val
        900
            905
                910

Asn Leu Met Gly Gly Asp Val Trp Val Lys Se
r Glu Tyr Gly Lys Gly
        915
            920
                925

Ser Lys Phe Phe Phe Thr Cys Val Val Arg Le
u Ala Asn Asp Asp Ile
    930
        935
            940

Ser Leu Ile Ala Lys Gln Leu Asn Pro Tyr Ly
s Ser His Gln Val Leu
945             9
50                  9
```

55          9
60

Phe Ile Asp Lys Gly Arg Thr Gly His Gly Pro Glu Ile Ala Lys Met
965
970
975

Leu His Gly Leu Gly Leu Val Pro Ile Val Val Asp Ser Glu Arg Asn
980
985
990

Pro Ala Leu Glu Lys Ala Arg Ala Ala Gly Gln Ala Pro Tyr Asp Val
995
1000
1005

Ile Ile Val Asp Ser Ile Glu Asp Ala Arg Arg Leu Arg Ser Val Asp
1010
1015
1020

Asp Phe Lys Tyr Leu Pro Ile Val Leu Leu Ala Pro Val Val His Val
1025          1030
1035
1040

Ser Leu Lys Ser Cys Leu Asp Leu Gly Ile Thr Ser Tyr Met Thr Thr
1045
1050
1055

Pro Cys Gln Leu Ile Asp Leu Gly Asn Gly Met Val Pro Ala Leu Glu
1060
1065
1070

Asn Arg Ala Thr Pro Ser Leu Ala Asp Asn Thr Lys Ser Phe Glu Ile
1075
1080
1085

Leu Leu Ala Glu Asp Asn Thr Val Asn Gln Arg Leu Ala Val Lys Ile
1090
1095
1100

Leu Glu Lys Tyr His His Val Val Thr Val Val Gly Asn Gly Glu Glu
1105          1110
1115
1120

Ala Val Glu Ala Val Lys Arg Lys Lys Phe Asp Val Ile Leu Met Asp
1125
1130
1135

Val Gln Met Pro Ile Met Gly Gly Phe Glu Ala Thr Ala Lys Ile Arg
1140
1145
1150

Glu Tyr Glu Arg Ser Leu Gly Ser Gln Arg Thr Pro Ile Ile Ala Leu
1155
1160
1165

Thr Ala His Ala Met Met Gly Asp Arg Glu Lys Cys Ile Gln Ala Gln
   1170            1175
       1180

Met Asp Glu Tyr Leu Ser Lys Pro Leu Gln Gln Asn His Leu Ile Gln
1185            1190
       1195
           1200

Thr Ile Leu Lys Cys Ala Thr Leu Gly Gly Gln Leu Leu Glu Lys Asn
               1205
           1210
       1215

Arg Glu Arg Glu Leu Thr Arg Ala Ala Asp Ala Val Thr Gly Gly Arg
           1220
       1225
           1230

Arg Asp Asn Gly Met Tyr Ser Ala Ser Gln Ala Ala Gln His Ala Ala
           1235
       1240
   1245

Leu Arg Pro Pro Leu Ala Thr Arg Gly Leu Thr Ala Ala Asp Ser Leu
   1250
   1255
   1260

Val Ser Gly Leu Glu Ser Pro Ser Ile Val Thr Ala Asp Lys Glu Asp
1265            1270
       1275
           1280

Pro Leu Ser Arg Ala Arg Ala Ser Leu Ser Glu Pro Asn Ile His Lys
               1285
           1290
       1295

Ala Ser (2) INFORMATION FOR SEQ ID NO:35:

(i) SEQUENCE CHARACTERISTICS:
        (A) LENGTH: 918 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:35:

Met Thr Asn Tyr Ser Leu Arg Ala Arg Met Met Ile Leu Ile Leu Ala
1               5
           10
               15

Pro Thr Val Leu Ile Gly Leu Leu Leu Ser Ile Phe Phe Val Val His
               20
           25
               30

Arg Tyr Asn Asp Leu Gln Arg Gln Leu Glu As

```
p Ala Gly Ala Ser Ile
        35
            40
                45

Ile Glu Pro Leu Ala Val Ser Thr Glu Tyr Gl
y Met Ser Leu Gln Asn
     50
         55
             60

Arg Glu Ser Ile Gly Gln Leu Ile Ser Val Le
u His Arg Arg His Ser
65
 70
  75
   80

Asp Ile Val Arg Ala Ile Ser Val Tyr Asp Gl
u Asn Asn Arg Leu Phe
                 85
                    90
                       95

Val Thr Ser Asn Phe His Leu Asp Pro Ser Se
r Met Gln Leu Gly Ser
         100
            105
               110

Asn Val Pro Phe Pro Arg Gln Leu Thr Val Th
r Arg Asp Gly Asp Ile
       115
          120
             125

Met Ile Leu Arg Thr Pro Ile Ile Ser Glu Se
r Tyr Ser Pro Asp Glu
     130
        135
           140

Ser Pro Ser Ser Asp Ala Lys Asn Ser Gln As
n Met Leu Gly Tyr Ile
145                 1
 50                  1
  55                  1
   60

Ala Leu Glu Leu Asp Leu Lys Ser Val Arg Le
u Gln Gln Tyr Lys Glu
               165
                  170
                     175

Ile Phe Ile Ser Ser Val Met Met Leu Phe Cy
s Ile Gly Ile Ala Leu
          180
             185
                190

Ile Phe Gly Trp Arg Leu Met Arg Asp Val Th
r Gly Pro Ile Arg Asn
       195
          200
             205

Met Val Asn Thr Val Asp Arg Ile Arg Arg Gl
y Gln Leu Asp Ser Arg
    210
       215
          220

Val Glu Gly Phe Met Leu Gly Glu Leu Asp Me
t Leu Lys Asn Gly Ile
225                 2
 30                  2
  35                  2
   40
```

-continued

Asn Ser Met Ala Met Ser Leu Ala Ala Tyr His Glu Glu Met Gln His
245 250 255

Asn Ile Asp Gln Ala Thr Ser Asp Leu Arg Glu Thr Leu Glu Gln Met
260 265 270

Glu Ile Gln Asn Val Glu Leu Asp Leu Ala Lys Lys Arg Ala Gln Glu
275 280 285

Ala Ala Arg Ile Lys Ser Glu Phe Leu Ala Asn Met Ser His Glu Leu
290 295 300

Arg Thr Pro Leu Asn Gly Val Ile Gly Phe Thr Arg Leu Thr Leu Lys
305 310 315 320

Thr Glu Leu Thr Pro Thr Gln Arg Asp His Leu Asn Thr Ile Glu Arg
325 330 335

Ser Ala Asn Asn Leu Leu Ala Ile Ile Asn Asp Val Leu Asp Phe Ser
340 345 350

Lys Leu Glu Ala Gly Lys Leu Ile Leu Glu Ser Ile Pro Phe Pro Leu
355 360 365

Arg Ser Thr Leu Asp Glu Val Val Thr Leu Leu Ala His Ser Ser His
370 375 380

Asp Lys Gly Leu Glu Leu Thr Leu Asn Ile Lys Ser Asp Val Pro Asp
385 390 395 400

Asn Val Ile Gly Asp Pro Leu Arg Leu Gln Gln Ile Ile Thr Asn Leu
405 410 415

Val Gly Asn Ala Ile Lys Phe Thr Glu Asn Gly Asn Ile Asp Ile Leu
420 425 430

Val Glu Lys Arg Ala Leu Ser Asn Thr Lys Val Gln Ile Glu Val Gln
435 440 445

-continued

```
Ile Arg Asp Thr Gly Ile Gly Ile Pro Glu Arg Asp Gln Ser Arg Leu
                450                 455                 460
Phe Gln Ala Phe Arg Gln Ala Asp Ala Ser Ile Ser Arg Arg His Gly
465                 470                 475                 480
Gly Thr Gly Leu Gly Leu Val Ile Thr Gln Lys Leu Val Asn Glu Met
                485                 490                 495
Gly Gly Asp Ile Ser Phe His Ser Gln Pro Asn Arg Gly Ser Thr Phe
                500                 505                 510
Trp Phe His Ile Asn Leu Asp Leu Asn Pro Asn Ile Ile Glu Gly
            515                 520                 525
Pro Ser Thr Gln Cys Leu Ala Gly Lys Arg Leu Ala Tyr Val Glu Pro
        530                 535                 540
Asn Ser Ala Ala Ala Gln Cys Thr Leu Asp Ile Leu Ser Glu Thr Pro
545                 550                 555                 560
Leu Glu Val Val Tyr Ser Pro Thr Phe Ser Ala Leu Pro Pro Ala His
                565                 570                 575
Tyr Asp Met Met Leu Leu Gly Ile Ala Val Thr Phe Arg Glu Pro Leu
                580                 585                 590
Thr Met Gln His Glu Arg Leu Ala Lys Ala Val Ser Met Thr Asp Phe
            595                 600                 605
Leu Met Leu Ala Leu Pro Cys His Ala Gln Val Asn Ala Glu Lys Leu
        610                 615                 620
Lys Gln Asp Gly Ile Gly Ala Cys Leu Leu Lys Pro Leu Thr Pro Thr
625                 630                 635                 640
Arg Leu Leu Pro Ala Leu Thr Glu Phe Cys His His Lys Gln Asn Thr
                645                 650                 655
```

Leu Leu Pro Val Thr Asp Glu Ser Lys Leu Ala Met Thr Val Met Ala
            660                 665                 670

Val Asp Asp Asn Pro Ala Asn Leu Lys Leu Ile Gly Ala Leu Leu Glu
        675                 680                 685

Asp Met Val Gln His Val Glu Leu Cys Asp Ser Gly His Gln Ala Val
    690                 695                 700

Glu Arg Ala Lys Gln Met Pro Phe Asp Leu Ile Leu Met Asp Ile Gln
705                 710                 715                 720

Met Pro Asp Met Asp Gly Ile Arg Ala Cys Glu Leu Ile His Gln Leu
                725                 730                 735

Pro His Gln Gln Gln Thr Pro Val Ile Ala Val Thr Ala His Ala Met
            740                 745                 750

Ala Gly Gln Lys Glu Lys Leu Leu Gly Ala Gly Met Ser Asp Tyr Leu
            755                 760                 765

Ala Lys Pro Ile Glu Glu Arg Leu His Asn Leu Leu Leu Arg Tyr
        770                 775                 780

Lys Pro Gly Ser Gly Ile Ser Ser Arg Val Val Thr Pro Glu Val Asn
785                 790                 795                 800

Glu Ile Val Val Asn Pro Asn Ala Thr Leu Asp Trp Gln Leu Ala Leu
                805                 810                 815

Arg Gln Ala Ala Gly Lys Thr Asp Leu Ala Arg Asp Met Leu Gln Met
                820                 825                 830

Leu Leu Asp Phe Leu Pro Glu Val Arg Asn Lys Val Glu Glu Gln Leu
        835                 840                 845

Val Gly Glu Asn Pro Glu Gly Leu Val Asp Leu Ile His Lys Leu His
    850                 855                 860

```
Gly Ser Cys Gly Tyr Ser Gly Val Pro Arg Me
t Lys Asn Leu Cys Gln
865              8
70               8
75               8
80

Leu Ile Glu Gln Gln Leu Arg Ser Gly Thr Ly
s Glu Glu Asp Leu Glu
            885
            890
            895

Pro Glu Leu Leu Glu Leu Leu Asp Glu Met As
p Asn Val Ala Arg Glu
            900
            905
            910

Ala Ser Lys Ile Leu Gly
        915

(2) INFORMATION FOR SEQ ID NO:36:

(i) SEQUENCE CHARACTERISTICS:
        (A) LENGTH: 1220 amino
acids
        (B) TYPE: amino acid
        (C) STRANDEDNESS: Not R
elevant
        (D) TOPOLOGY: Not Relev
ant (ii) MOLECULE TYPE: protein (xi) SEQUENCE DESCRIPTION: SEQ ID NO:36:

Met Arg Phe Gly Leu Pro Ser Lys Leu Glu Le
u Thr Pro Pro Phe Arg
1            5
            10
            15

Ile Gly Ile Arg Thr Gln Leu Thr Ala Leu Va
l Ser Ile Val Ala Leu
        20
        25
        30

Gly Ser Leu Ile Ile Leu Ala Val Thr Thr Gl
y Val Tyr Phe Thr Ser
        35
        40
        45

Asn Tyr Lys Asn Leu Arg Ser Asp Arg Leu Ty
r Ile Ala Ala Gln Leu
    50
    55
    60

Lys Ser Ser Gln Ile Asp Gln Thr Leu Asn Ty
r Leu Tyr Tyr Gln Ala
65
70
75
80

Tyr Tyr Leu Ala Ser Arg Asp Ala Leu Gln Se
r Ser Leu Thr Ser Tyr
            85
            90
            95

Val Ala Gly Asn Lys Ser Ala Asp Asn Trp Va
l Asp Ser Leu Ser Val
        100
        105
```

```
                    110
Ile Gln Lys Phe Leu Ser Ser Ser Asn Leu Ph
e Tyr Val Ala Lys Val
        115
                120
                        125

Tyr Asp Ser Ser Phe Asn Ala Val Leu Asn Al
a Thr Asn Asn Gly Thr
    130
            135
                    140

Gly Asp Leu Ile Pro Glu Asp Val Leu Asp Se
r Leu Phe Pro Leu Ser
145                 1
50                      1
55                          1
60

Thr Asp Thr Pro Leu Pro Ser Ser Leu Glu Th
r Ile Gly Ile Leu Thr
            165
                    170
                            175

Asp Pro Val Leu Asn Ser Thr Asp Tyr Leu Me
t Ser Met Ser Leu Pro
            180
                    185
                            190

Ile Phe Ala Asn Pro Ser Ile Ile Leu Thr As
p Ser Arg Val Tyr Gly
        195
                200
                        205

Tyr Ile Thr Ile Ile Met Ser Ala Glu Gly Le
u Lys Ser Val Phe Asn
    210
            215
                    220

Asp Thr Thr Ala Leu Glu His Ser Thr Ile Al
a Ile Ile Ser Ala Val
225                 2
30                      2
35                          2
40

Tyr Asn Ser Gln Gly Lys Ala Ser Gly Tyr Hi
s Phe Val Phe Pro Pro
                245
                        250
                                255

Tyr Gly Ser Arg Ser Asp Leu Pro Gln Lys Va
l Phe Ser Ile Lys Asn
            260
                    265
                            270

Asp Thr Phe Ile Ser Ser Ala Phe Arg Asn Gl
y Lys Gly Gly Ser Leu
        275
                280
                        285

Lys Gln Thr Asn Ile Leu Ser Thr Arg Asn Th
r Ala Leu Gly Tyr Ser
    290
            295
                    300

Pro Cys Ser Phe Asn Leu Val Asn Trp Val Al
a Ile Val Ser Gln Pro
305                 3
10                      3
```

```
15              3
20

Glu Ser Val Phe Leu Ser Pro Ala Thr Lys Le
u Ala Lys Ile Ile Thr
                325
                    330
                        335

Gly Thr Val Ile Ala Ile Gly Val Phe Val Il
e Leu Thr Leu Pro
            340
                345
                    350

Leu Ala His Trp Ala Val Gln Pro Ile Val Ar
g Leu Gln Lys Ala Thr
        355
            360
                365

Glu Leu Ile Thr Glu Gly Arg Gly Leu Arg Pr
o Ser Thr Pro Arg Thr
    370
        375
            380

Ile Ser Arg Ala Ser Ser Phe Lys Arg Gly Ph
e Ser Ser Gly Phe Ala
385                 3
90                      3
95                          4
00

Val Pro Ser Ser Leu Leu Gln Phe Asn Thr Al
a Glu Ala Gly Ser Thr
                405
                    410
                        415

Thr Ser Val Ser Gly His Gly Gly Ser Gly Hi
s Gly Ser Gly Ala Ala
            420
                425
                    430

Phe Ser Ala Asn Ser Ser Met Lys Ser Ala Il
e Asn Leu Gly Asn Glu
        435
            440
                445

Lys Met Ser Pro Pro Glu Glu Glu Asn Lys Il
e Pro Asn Asn His Thr
    450
        455
            460

Asp Ala Lys Ile Ser Met Asp Gly Ser Leu As
n His Asp Leu Leu Gly
465                 4
70                      4
75                          4
80

Pro His Ser Leu Arg His Asn Asp Thr Asp Ar
g Ser Ser Asn Arg Ser
                485
                    490
                        495

His Ile Leu Thr Thr Ser Ala Asn Leu Thr Gl
u Ala Arg Leu Pro Asp
            500
                505
                    510

Tyr Arg Arg Leu Phe Ser Asp Glu Leu Ser As
p Leu Thr Glu Thr Phe
        515
```

```
                    520
                525

Asn Thr Met Thr Asp Ala Leu Asp Gln His Ty
r Ala Leu Leu Glu Glu
    530
        535
            540

Arg Val Arg Ala Arg Thr Lys Gln Leu Glu Al
a Ala Lys Ile Glu Ala
545             5
50               5
55               5
60

Glu Ala Ala Asn Glu Ala Lys Thr Val Phe Il
e Ala Asn Ile Ser His
            565
                570
                    575

Glu Leu Arg Thr Pro Leu Asn Gly Ile Leu Gl
y Met Thr Ala Ile Ser
        580
            585
                590

Met Glu Glu Thr Asp Val Asn Lys Ile Arg As
n Ser Leu Lys Leu Ile
        595
            600
                605

Phe Arg Ser Gly Glu Leu Leu His Ile Le
u Thr Glu Leu Leu Thr
    610
        615
            620

Phe Ser Lys Asn Val Leu Gln Arg Thr Lys Le
u Glu Lys Arg Asp Phe
625                  6
30                   6
35                   6
40

Cys Ile Thr Asp Val Ala Leu Gln Ile Lys Se
r Ile Phe Gly Lys Val
            645
                650
                    655

Ala Lys Asp Gln Arg Val Arg Leu Ser Ile Se
r Leu Phe Pro Asn Leu
        660
            665
                670

Ile Arg Thr Met Val Leu Trp Gly Asp Ser As
n Arg Ile Ile Gln Ile
            675
                680
                    685

Val Met Asn Leu Val Ser Asn Ala Leu Lys Ph
e Thr Pro Val Asp Gly
    690
        695
            700

Thr Val Asp Val Arg Met Lys Leu Leu Gly Gl
u Tyr Asp Lys Glu Leu
705                  7
10                   7
15                   7
20

Ser Glu Lys Lys Gln Tyr Lys Glu Val Tyr Il
e Lys Lys Gly Thr Glu
```

Val Thr Glu Asn Leu Glu Thr Thr Asp Lys Tyr Asp Leu Pro Thr Leu
            725                 730                 735
                            740                 745                 750

Ser Asn His Arg Lys Ser Val Asp Leu Glu Ser Ser Ala Thr Ser Leu
            755                 760                 765

Gly Ser Asn Arg Asp Thr Ser Thr Ile Gln Glu Glu Ile Thr Lys Arg
            770                 775                 780

Asn Thr Val Ala Asn Glu Ser Ile Tyr Lys Lys Val Asn Asp Arg Glu
        785                 790                 795                 800

Lys Ala Ser Asn Asp Asp Val Ser Ser Ile Val Ser Thr Thr Thr Ser
            805                 810                 815

Ser Tyr Asp Asn Ala Ile Phe Asn Ser Gln Phe Asn Lys Ala Pro Gly
            820                 825                 830

Ser Asp Asp Glu Glu Gly Gly Asn Leu Gly Arg Pro Ile Glu Asn Pro
            835                 840                 845

Lys Thr Trp Val Ile Ser Ile Glu Val Glu Asp Thr Gly Pro Gly Ile
        850                 855                 860

Asp Pro Ser Leu Gln Glu Ser Val Phe His Pro Phe Val Gln Gly Asp
865                 870                 875                 880

Gln Thr Leu Ser Arg Gln Tyr Gly Gly Thr Gly Leu Gly Leu Ser Ile
            885                 890                 895

Cys Arg Gln Leu Ala Asn Met Met His Gly Thr Met Lys Leu Glu Ser
            900                 905                 910

Lys Val Gly Val Gly Ser Lys Phe Thr Phe Thr Leu Pro Leu Asn Gln
            915                 920                 925

Thr Lys Glu Ile Ser Phe Ala Asp Met Glu Phe Pro Phe Glu Asp Glu 930
              935
              940

Phe Asn Pro Glu Ser Arg Lys Asn Arg Va
l Lys Phe Ser Val Ala
945                 9
50           9
55           9
60

Lys Ser Ile Lys Ser Arg Gln Ser Thr Ser Se
r Val Ala Thr Pro Ala
              965
              970
              975

Thr Asn Arg Ser Ser Leu Thr Asn Asp Val Le
u Pro Glu Val Arg Ser
              980
              985
              990

Lys Gly Lys His Glu Thr Lys Asp Val Gly As
n Pro Asn Met Gly Arg
          995
          1000
          1005

Glu Glu Lys Asn Asp Asn Gly Gly Leu Glu Gl
n Leu Gln Glu Lys Asn
      1010
      1015
      1020

Ile Lys Pro Ser Ile Cys Leu Thr Gly Ala Gl
u Val Asn Glu Gln Asn
1025              1030
              1035
              1040

Ser Leu Ser Ser Lys His Arg Ser Arg His Gl
u Gly Leu Gly Ser Val
              1045
              1050
              1055

Asn Leu Asp Arg Pro Phe Leu Gln Ser Thr Gl
y Thr Ala Thr Ser Ser
              1060
              1065
              1070

Arg Asn Ile Pro Thr Val Lys Asp Asp Asp Ly
s Asn Glu Thr Ser Val
          1075
          1080
          1085

Lys Ile Leu Val Val Glu Asp Asn His Val As
n Gln Glu Val Ile Lys
      1090
   1095
1100

Arg Met Leu Asn Leu Glu Gly Ile Glu Asn Il
e Glu Leu Ala Cys Asp
1105              1110
              1115
              1120

Gly Gln Glu Ala Phe Asp Lys Val Lys Glu Le
u Thr Ser Lys Gly Glu
              1125
              1130
              1135

Asn Tyr Asn Met Ile Phe Met Asp Val Gln Me
t Pro Lys Val Asp Gly
              1140

```
                1145
                1150

Leu Leu Ser Thr Lys Met Ile Arg Arg Asp Le
u Gly Tyr Thr Ser Pro
            1155
        1160
      1165

Ile Val Ala Leu Thr Ala Phe Ala Asp Asp Se
r Asn Ile Lys Glu Cys
       1170
     1175
   1180

Leu Glu Ser Gly Met Asn Gly Phe Leu Ser Ly
s Pro Ile Lys Arg Pro
1185                 1190
              1195
              1200

Lys Leu Lys Thr Ile Leu Thr Glu Phe Cys Al
a Ala Tyr Gln Gly Lys
              1205
              1210
              1215

Lys Asn Asn Lys
            1220
```